US009011821B2

(12) United States Patent
Brummelkamp et al.

(10) Patent No.: US 9,011,821 B2
(45) Date of Patent: Apr. 21, 2015

(54) PLA2G16 AS A TARGET FOR ANTIVIRAL COMPOUNDS

(75) Inventors: Thijn R. Brummelkamp, Amsterdam (NL); Jan E. Carette, Palo Alto, CA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 0 days.

(21) Appl. No.: 13/805,201

(22) PCT Filed: Jun. 17, 2011

(86) PCT No.: PCT/US2011/040920
§ 371 (c)(1),
(2), (4) Date: Apr. 3, 2013

(87) PCT Pub. No.: WO2011/160043
PCT Pub. Date: Dec. 22, 2011

(65) Prior Publication Data
US 2013/0219533 A1     Aug. 22, 2013

Related U.S. Application Data

(60) Provisional application No. 61/356,426, filed on Jun. 18, 2010.

(51) Int. Cl.
| | | |
|---|---|---|
| *C12Q 1/00* | (2006.01) | |
| *C12Q 1/18* | (2006.01) | |
| *C12Q 1/44* | (2006.01) | |
| *A61B 5/00* | (2006.01) | |
| *A61B 5/103* | (2006.01) | |
| *A61B 5/11* | (2006.01) | |
| *A61K 38/00* | (2006.01) | |

(52) U.S. Cl.
CPC .. *C12Q 1/44* (2013.01); *C12Q 1/18* (2013.01); *A61B 5/0002* (2013.01); *A61B 5/1038* (2013.01); *A61B 5/112* (2013.01); *A61B 5/6807* (2013.01); *A61B 5/7225* (2013.01); *A61B 5/7278* (2013.01); *A61B 5/7285* (2013.01); *A61K 38/00* (2013.01); *G01N 2333/918* (2013.01)

(58) Field of Classification Search
USPC ................. 424/9.2, 93.3; 435/5, 18
See application file for complete search history.

(56) References Cited

U.S. PATENT DOCUMENTS

| | | |
|---|---|---|
| 2003/0144282 A1 | 7/2003 | Mckew et al. |
| 2007/0004719 A1 | 1/2007 | McKew et al. |
| 2008/0319065 A1 | 12/2008 | Dennis et al. |
| 2010/0022536 A1 | 1/2010 | McKew et al. |
| 2010/0029645 A1 | 2/2010 | McKew et al. |

FOREIGN PATENT DOCUMENTS

| | | |
|---|---|---|
| WO | WO 00/27824 | 5/2000 |
| WO | WO 01/60805 | 8/2001 |
| WO | WO 02/30904 | 4/2002 |
| WO | WO 02/30911 | 4/2002 |
| WO | WO 03/041712 | 5/2003 |
| WO | WO 03/042206 | 5/2003 |
| WO | WO 03/042218 | 5/2003 |
| WO | WO 03/048139 | 6/2003 |
| WO | WO 03/086400 | 10/2003 |
| WO | WO 03/087088 | 10/2003 |

OTHER PUBLICATIONS

Duncan et al, J. Biol. Chem. 283(37):25428-25436, 2008.*
Ghomashchi et al, Biochem. Biophys. Acta 1513:160-166, 2001.*
Zadori et al, Dev. Cell (1):291-302, 2001.*
Hughes et al, J. Gen. Virol. 81:201-207, 2000.*
Duncan, et al., "Identification and Functional Characterization of Adipose-specific Phospholipase A2 (AdPLA)", *The Journal of Biological Chemistry*, 283(37): 25428-25436 (2008).
Jaworski, et al., "AdPLA ablation increases lipolysis and prevents obesity induced by high-fat feeding or leptin deficiency", *Nature Medicine*, 15(2): 159-168 (2009).
Martin, et al. "Cannabinoid Properties of Methylfluorophosphonate Analogs", *The Journal of Pharmacology and Experimental Therapeutics*, 294(3): 1209-1218 (2000).
Street, et al., "Slow and tight-binding inhibitors of the 85-kDa human phospholipase A2", *Biochemistry*, 32(23): 5935-5940 (1993).
International Search Report for International Application PCT/US2011/040920, dated Apr. 18, 2012.
International Preliminary Report on Patentability for International Application PCT/US2011/040920, dated Jan. 3, 2013.
Nazarenko, et al., "H-REV107-1 Stimulates Growth in Non-Small Cell Lung Carcinomas via the Activation of Mitogenic Signaling" *The American Journal of Pathology*, 169(4): 1427-1439 (2006).

* cited by examiner

*Primary Examiner* — Kevin Hill
(74) *Attorney, Agent, or Firm* — Lisa M. Warren, Esq.; Morse, Barnes-Brown & Pendleton, P.C.

(57) ABSTRACT

In some aspects, the invention provides compositions and methods for inhibiting viral infection. In some aspects, the invention provides compositions and methods useful for identifying antiviral compounds.

13 Claims, 8 Drawing Sheets

Coxsackievirus B1

| | MOI | 0.00016 | 0.0008 | 0.004 | 0.02 | 0.1 |
|---|---|---|---|---|---|---|
| WT | | | | | | |
| PLA2G16$^{GT}$ | | | | | | |
| PLA2G16$^{GT}$ + PLA2G16 | | | | | | |
| PLA2G16$^{GT}$ + PLA2G16 MUT | | | | | | |

Fig. 5

PLA2G16 amino acid sequences from various mammalian species.

human (Homo sapiens)    SEQ ID NO: 1
mouse (Mus musculus)    SEQ ID NO: 2
rat (Rattus norvegicus) SEQ ID NO: 3

```
1    MRAPIPEPKP GDLIEIFRPF YRHWAIYVGD GYVVHLAPPS EVAGAGAASV MSALTDKAIV
61   KKELLYDVAG SDKYQVNNKH DDKYSPLPCS KIIQRAEELV GQEVLYKLTS ENCEHFVNEL
121  RYGVARSDQV RDVIIAASVA GMGLAAMSLI GVMFSRNKRQ KQ (SEQ ID NO: 1)

1    MLAPIPEPKP GDLIEIFRPM YRHWAIYVGD GYVIHLAPPS ETAGAGAAST MSALTDKAIV
61   KKELLCHVAG KDKYQVNNKH DEEYTPLPLS KIIQRAERLV GQEVLYRLTS ENCEHFVNEL
121  RYGVPRSDQV RDAVKAVGIA GVGLAALGLV GVMLSRNKKQ KQ (SEQ ID NO: 2)

1    MPIPEPKPGD LIEIFRPMYS HWAIYVGDGY VIHLAPPSEI PGAGAASIMS ALTDKAIVKK
61   ELLRDVAGKD KYQVNNKHDK EYTPLPLNKI IQRAEELVGQ EVLYRLTSEN CEHFVNELRY
121  GVPRSDQVRD AVKVATVTGV GLAALGLIGV MLSRNKKQKQ (SEQ ID NO: 3)
```

Figure 8

PLA2G16 AS A TARGET FOR ANTIVIRAL COMPOUNDS

CROSS-REFERENCE TO RELATED APPLICATIONS

This application is a national stage filing under 35 U.S.C. 371 of International Application No. PCT/US2011/40920, filed Jun. 17, 2011, which claims priority to and the benefit of U.S. Application No. 61/356,426, filed Jun. 18, 2010. The entire contents of these applications are incorporated herein by reference. International Application PCT/US2011/40920 was published under PCT Article 21(2) in English.

BACKGROUND OF THE INVENTION

Viruses are major causes of disease and death throughout the world. Although vaccines and public health measures have greatly reduced the incidence of certain viral infections, such approaches have been less successful in tackling many viruses of significant medical and/or veterinary importance. Even if a generally protective vaccine exists, it is challenging to achieve vaccination of all individuals. Furthermore, obstacles to effective immunization can arise due to factors such as immune senescence and treatment with immunosuppressive medications. Pharmacological therapies have been developed against some viruses, with human immunodeficiency virus (HIV) being a notable example. However, there are still relatively few viral diseases for which effective drugs are available. There is a need for new antiviral compounds and for new approaches to identifying such compounds.

SUMMARY OF THE INVENTION

The invention relates at least in part to identification of a target for antiviral drug discovery. In one aspect, the invention provides a method of inhibiting viral infection of a cell comprising contacting the cell with a PLA2G16 inhibitor. In some embodiments, the virus is a Picornavirus. In some embodiments, the cell is a vertebrate cell. In some embodiments the vertebrate cell is a mammalian cell, e.g., a human cell. In some embodiments, the PLA2G16 inhibitor inhibits expression of PLA2G16. In some embodiments, the PLA2G16 inhibitor inhibits enzymatic activity of PLA2G16.

In another aspect, the invention provides a method of treating a viral infection in a subject, the method comprising administering a PLA2G16 inhibitor to a subject in need of treatment for a viral infection. In some embodiments, the viral infection is a Picornavirus infection. In some embodiments, the subject is a vertebrate. In some embodiments, the subject is a mammal, e.g., a human. In some embodiments, the PLA2G16 inhibitor inhibits expression of PLA2G16. In some embodiments, the PLA2G16 inhibitor inhibits enzymatic activity of PLA2G16.

In another aspect, the invention provides a method of identifying a candidate antiviral compound comprising steps of: (a) providing a composition comprising a PLA2G16 polypeptide and a test compound; (b) determining whether the test compound inhibits the PLA2G16 polypeptide, wherein if the compound inhibits the PLA2G16 polypeptide, the compound is identified as a candidate antiviral compound. In some embodiments, step (b) comprises determining whether the test compound inhibits expression of the PLA2G16 polypeptide. In some embodiments, step (b) comprises determining whether the test compound inhibits an enzymatic activity of the PLA2G16 polypeptide. In some embodiments, the enzymatic activity is phospholipase A2 activity. In some embodiments, the composition of step (a) is a cell-free composition comprising purified PLA2G16; and step (b) comprises determining whether the test compound inhibits enzymatic activity of PLA2G16. In some embodiments, the composition of step (a) comprises a cell that expresses a PLA2G16 polypeptide, and wherein step (b) comprises determining whether the test compound inhibits expression or enzymatic activity of PLA2G16. In some embodiments, if the compounds inhibits the PLA2G16 polypeptide, the compound is identified as a candidate antiviral compound useful for inhibiting viral infection by a Picornavirus. In some embodiments, the method further comprises assessing the ability of the compound to inhibit viral infection of a cell or subject. In some embodiments, the method further comprises the step of contacting a cell with the compound and a virus, wherein the cell would be susceptible to the virus in the absence of the compound. In some embodiments, the method further comprises the step of administering the compound to a subject, wherein the subject would be susceptible to infection by the virus in the absence of the compound. In some embodiments, the method further comprises the step of contacting a cell that is infected by the virus with the compound. In some embodiments, the method further comprises the step of administering the compound to a subject, wherein the subject is infected by a virus.

In another aspect, the invention provides a method of validating a candidate antiviral compound comprising steps of: (a) providing a candidate antiviral compound identified according to a method that comprises identifying or selecting a compound that inhibits PLA2g16; and (b) determining whether the compound inhibits infection of a cell or organism by a virus, wherein if the compound inhibits infection of a cell or organism by the virus, the compound is validated as an antiviral compound. In some embodiments, the virus is a Picornavirus.

In another aspect, the invention provides a composition comprising: (a) a PLA2G16 inhibitor; (b) a virus; and (c) a population of cells. In some embodiments, the virus is present at a multiplicity of infection (MOI) of at least 0.01. In some embodiments, the virus is a Picornavirus. In some embodiments, the cells are in culture. In some embodiments, the cells are vertebrate cells. In some embodiments, the cells are mammalian cells, e.g., human cells. In some embodiments, the population of cells comprises at least $10^2$, $10^3$, $10^4$, $10^5$, $10^6$, $10^7$, or more cells. In some embodiments, the cells are human cells. In some embodiments, at least some of the cells are infected by the virus. In some embodiments, the PLA2G16 inhibitor binds to PLA2G16. In some embodiments, the PLA2G16 inhibitor inhibits expression of PLA2G16. In some embodiments, the PLA2G16 inhibitor inhibits an enzymatic activity of PLA2G16. In some embodiments, the PLA2G16 inhibitor is a small molecule. In some embodiments, the PLA2G16 inhibitor is present in an amount sufficient to detectably inhibit infection of the cells by the virus.

In another aspect, the invention provides a composition comprising a PLA2G16 inhibitor, wherein the composition is useful for treating a viral infection in a subject. In some embodiments, the PLA2G16 inhibitor binds to PLA2G16. In some embodiments, the PLA2G16 inhibitor inhibits expression of PLA2G16. In some embodiments, the PLA2G16 inhibitor inhibits an enzymatic activity of PLA2G16. In some embodiments, the PLA2G16 inhibitor is a small molecule. In some embodiments, the viral infection is a Picornavirus infection. In some embodiments, the subject is a vertebrate. In some embodiments, the subject is a mammal, e.g., a human.

In another aspect, the invention provides a mammalian cell that has a mutation in a gene that encodes PLA2G16. In some embodiments the cell is a near-haploid cell. In some embodiments, the cell expresses a mutant form of PLA2G16. In some embodiments, the cell expresses a mutant form of PLA2G16, wherein the mutant form has reduced catalytic activity as compared with the non-mutant form.

In another aspect, the invention provides a method of identifying a non-human multicellular organism, e.g., a vertebrate animal, that has increased resistance to viral infection, the method comprising identifying a multicellular organism that has reduced or absent functional PLA2G16. In some embodiments the invention provides a method of identifying a non-human multicellular organism with increased resistance to infection by a virus, the method comprising determining whether the organism has reduced PLA2G16 expression or activity, wherein if the organism has reduced PLA2G16 expression or activity, the organism has increased resistance to infection by a virus. In some embodiments, the method further comprises providing or using an organism with reduced or absent PLA2G16 in agriculture and/or animal husbandry. In some embodiments, a virus-resistant animal is of a non-domesticated species. Optionally the species is endangered. In some embodiments, the organism is a commercially important vertebrate animal. In some embodiments of the inventive methods, the organism is not genetically modified.

In another aspect, the invention provides a farm animal having reduced or absent functional PLA2G16, wherein the animal has increased resistance to infection by a virus. In some embodiments the animal is not genetically modified. In other embodiments the animal is genetically modified.

In certain embodiments of any of the aspects of the invention, the Picornavirus is an enterovirus (member of the Enterovirus genus). In certain embodiments the enterovirus is a human enterovirus, e.g., a virus classified within the Human enterovirus A, Human enterovirus B, Human enterovirus C, Human enterovirus D, Human rhinovirus A, Human rhinovirus B, or Human rhinovirus C species. In some embodiments, the human enterovirus is poliovirus 1, 2, or 3 or any of human enteroviruses 68-107, e.g., EV-71. In certain embodiments of any of the aspects of the invention, the Picornavirus is a hepatovirus, e.g., human hepatitis A virus. In certain embodiments of any of the aspects of the invention, the Picornavirus is a coxsackievirus. In certain embodiments the coxsackievirus is a human coxsackievirus, e.g., any coxsackieviruses A1-A22, A24, or B1-B5. In certain embodiments of any of the aspects of the invention, the Picornavirus is a rhinovirus (member of Human rhinovirus A, Human rhinovirus B, or Human rhinovirus C species), e.g., any of human rhinoviruses 1-100. In certain embodiments of any of the aspects of the invention, the Picornavirus is an echovirus. In certain embodiments of any of the various aspects of the invention, the virus is a foot-and-mouth disease virus, e.g., one of the seven foot-and-mouth disease virus serotypes: O, A, C, SAT-1, SAT-2, SAT-3, and Asia-1.

The practice of the present invention will typically employ, unless otherwise indicated, conventional techniques of cell biology, cell culture, molecular biology, transgenic biology, microbiology, recombinant nucleic acid (e.g., DNA) technology, immunology, and RNA interference (RNAi) which are within the skill of the art. Non-limiting descriptions of certain of these techniques are found in the following publications: Ausubel, F., et al., (eds.), *Current Protocols in Molecular Biology, Current Protocols in Immunology, Current Protocols in Protein Science*, and *Current Protocols in Cell Biology*, all John Wiley & Sons, N.Y., edition as of December 2008; Sambrook, Russell, and Sambrook, *Molecular Cloning: A Laboratory Manual*, 3$^{rd}$ ed., Cold Spring Harbor Laboratory Press, Cold Spring Harbor, 2001; Harlow, E. and Lane, D., Antibodies—A Laboratory Manual, Cold Spring Harbor Laboratory Press, Cold Spring Harbor, 1988; Freshney, R. I., "Culture of Animal Cells, A Manual of Basic Technique", 5th ed., John Wiley & Sons, Hoboken, N.J., 2005. Non-limiting information regarding viruses is found in, e.g., Knipe, D M and Howley, P M (eds.) *Fields Virology*, Volumes I and II. 5$^{th}$ ed. Lippincott Williams and Wilkins, 2007; Büchen-Osmond, C. (Ed), (2006) Index to ICTVdB virus descriptions. In: ICTVdB—The Universal Virus Database, version 4. ICTVdB Management, Mailman School of Public Health, Columbia University, New York, N.Y., USA; and "ICTVdB—The Universal Virus Database", version 4, April 2006 (available on the World Wide Web) and ICTVdb Virus Descriptions (available on the World Wide Web). (It is noted that the online database is currently being rewritten.) The most recent report of the International Committee on the Taxonomy of Viruses (ICTV) of the International Union of Microbiological Societies: "Virus Taxonomy: VIIIth Report of the International Committee on Taxonomy of Viruses", 2005, C. M. Fauquet, M. A. Mayo, J. Maniloff, U. Desselberger, and L. A. Ball (Eds), Elsevier Academic Press, is considered the standard and definitive reference for virus taxonomy (classification and nomenclature), as supplemented by taxonomic proposals subsequently approved by the ICTV (available as updates on the ICTV website) (See also Carstens, E B and Ball, L. Ratification vote on taxonomic proposals to the International Committee on Taxonomy of Viruses. Archives of Virology, Volume 154, Number 7, 2008, and Carstens, E. Ratification vote on taxonomic proposals to the International Committee on Taxonomy of Viruses (2009) Archives of Virology, Volume 155, Number 1, 2009). The Virus Taxonomy: 2009 Release v4 (Mar. 20, 2010) (available on the ICTV website) represents the most recent taxonomy.

Non-limiting information regarding therapeutic agents and human diseases is found in Goodman and Gilman's The Pharmacological Basis of Therapeutics, 11th Ed., McGraw Hill, 2005, Katzung, B. (ed.) Basic and Clinical Pharmacology, McGraw-Hill/Appleton & Lange; 10$^{th}$ ed. (2006) or 11th edition (July 2009), All patents, patent applications, and other publications (e.g., scientific articles, books, websites, and databases) mentioned herein are incorporated by reference in their entirety. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 5. Cells containing a PLA2G16 gene trap insertion are resistant to coxsackievirus B1. Cells were plated in 24-well wells and monolayers were virus was added at the indicated MOIs. Four days after infection viable, adherent cells were stained using crystal violet. Cells mutant for PLA2G16 were unaffected by high concentrations of coxsackievirus B1. Complementation of PLA2G16 by retroviral overexpression restores sensitivity of these cells to coxsackievirus B1. This requires the catalytic activity of PLA2G16 because complementation with a catalytic site mutant (C113A) does not restore sensitivity.

PLA2G16: HAP1 cells containing gene trap insertion into PLA2G16 gene (PLA2G16$^{GT}$)

PLA2G16+PM2G16WT: HAP1 PLA2G16$^{GT}$ cells infected with retrovirus encoding wild type PLA2G16

PLA2G16+PM2G16MUT: HAP1 PLA2G16$^{GT}$ cells infected with retrovirus encoding catalytically inactive mutant PLA2G16 (with C113A mutation)

PVR: HAP1 cells with gene trap insertion into poliovirus receptor.

Figure 7:
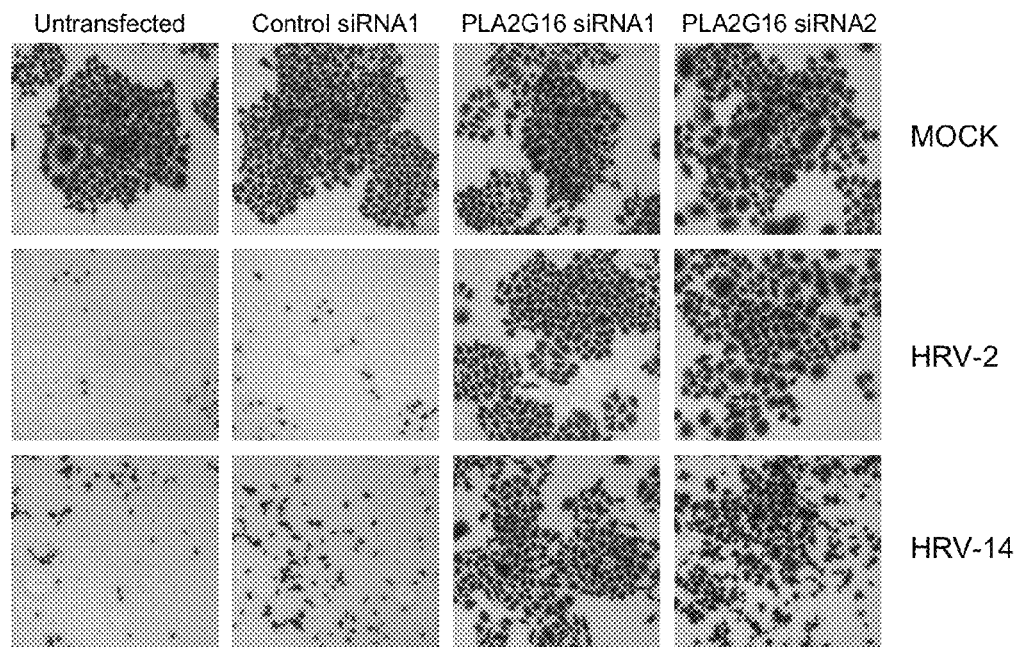

FIG. 7. Knock down of PLA2G16 in Hela cells results in increased resistance to the human rhinoviruses HRV-2 and HRV-14.

FIG. 8. Exemplary PLA2G16 sequences. Predicted transmembrane domain is shown in bold in the human sequence.

DETAILED DESCRIPTION OF CERTAIN
EMBODIMENTS OF THE INVENTION

I. Definitions

The term "antibody" encompasses immunoglobulins and derivatives thereof containing an immunoglobulin domain capable of binding to an antigen. An antibody can originate from a mammalian or avian species, e.g., human, rodent (e.g., mouse, rabbit), goat, chicken, etc., or can be generated ex vivo using a technique such as phage display. Antibodies include members of the various immunoglobulin classes, e.g., IgG, IgM, IgA, IgD, IgE, or subclasses thereof such as IgG1, IgG2, etc. In various embodiments of the invention "antibody" refers to an antibody fragment or molecule such as an Fab', F(ab')2, scFv (single-chain variable) that retains an antigen binding site and encompasses recombinant molecules comprising one or more variable domains (VH or VL). An antibody can be monovalent, bivalent or multivalent in various embodiments. The antibody may be a chimeric or "humanized" antibody. An antibody may be polyclonal or monoclonal, though monoclonal antibodies may be preferred. In some aspects, an antibody is an intrabody, which may be expressed intracellularly. In some embodiments a compound comprises a single-chain antibody and a protein transduction domain (e.g., as a fusion polypeptide).

An "effective amount" or "effective dose" of a compound or other agent (or composition containing such compound or agent) refers to the amount sufficient to achieve a desired biological and/or pharmacological effect, e.g., when delivered to a cell or organism according to a selected administration form, route, and/or schedule. As will be appreciated by those of ordinary skill in this art, the absolute amount of a particular compound, agent, or composition that is effective may vary depending on such factors as the desired biological or pharmacological endpoint, the agent to be delivered, the target tissue, etc. Those of ordinary skill in the art will further understand that an "effective amount" may be contacted with cells or administered in a single dose, or the desired effect may be achieved by use of multiple doses. An effective amount of an antiviral compound may be an amount sufficient to achieve one or more of the following: (i) reduce virus replication (e.g., reduce production of progeny virus) in cell culture and/or in vivo; (ii) reduce the severity of or prevent one or more symptoms or signs of a viral infection; (iii) significantly reduce the risk of recurrence of a viral infection (e.g., reduce the risk of relapse); (iv) significantly reduce the risk of a clinically significant infection in a subject who has been exposed to an infectious agent, etc.

"Identity" or "percent identity" is a measure of the extent to which the sequence of two or more nucleic acids or polypeptides is the same. The percent identity between a sequence of interest A and a second sequence B may be computed by aligning the sequences, allowing the introduction of gaps to maximize identity, determining the number of residues (nucleotides or amino acids) that are opposite an identical residue, dividing by the minimum of $TG_A$ and $TG_B$ (here $TG_A$ and $TG_B$ are the sum of the number of residues and internal gap positions in sequences A and B in the alignment), and multiplying by 100. When computing the number of identical residues needed to achieve a particular percent identity, fractions are to be rounded to the nearest whole number. Sequences can be aligned with the use of a variety of computer programs known in the art. For example, computer programs such as BLAST2, BLASTN, BLASTP, Gapped BLAST, etc., generate alignments. The algorithm of Karlin and Altschul (Karlin and Altschul, Proc. Natl. Acad. Sci. USA 87:22264-2268, 1990) modified as in Karlin and Altschul, Proc. Natl. Acad Sci. USA 90:5873-5877, 1993 is incorporated into the NBLAST and XBLAST programs of Altschul et al. (Altschul, et al., J. Mol. Biol. 215:403-410, 1990). In some embodiments, to obtain gapped alignments for comparison purposes, Gapped BLAST is utilized as described in Altschul et al. (Altschul, et al. Nucleic Acids Res. 25: 3389-3402, 1997). When utilizing BLAST and Gapped BLAST programs, the default parameters of the respective programs may be used. See the Web site having URL www.ncbi.nlm.nih.gov. Other suitable programs include CLUSTALW (Thompson J D, Higgins D G, Gibson T J, Nuc Ac Res, 22:4673-4680, 1994) and GAP (GCG Version 9.1; which implements the Needleman & Wunsch, 1970 algorithm (Needleman S B, Wunsch C D, J Mol Biol, 48:443-453, 1970.)

"Infection" refers to the (often detrimental) colonization of a cell (sometimes referred to as a "host cell" or "host") or multicellular organism (sometimes referred to as a "host"), by a microorganism such as a virus. The process of infection encompasses entry of the virus into one or more cell(s) (invasion) and, if the infection proceeds, subsequent steps in the viral life cycle, typically resulting in multiplication of the virus and, frequently in the case of viruses of medical or veterinary importance, detrimental effects of the virus on the host. A viral infection can be any situation in which the presence of one or more virus population(s) is damaging to a host cell or organism. The term "infection" encompasses excessive replication of viruses that are normally present in or on the body of a vertebrate, e.g., mammal, or other organism, or the presence and, optionally, replication, of viruses that are not normally present in or on the body of a vertebrate, e.g., a mammal, or other organism.

"Inhibit" may be used interchangeably with terms such as "suppress", "decrease", and the like, as appropriate in the context. It will be understood that the extent of inhibition can vary. For example, inhibition can refer to a reduction by at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99%.

"Isolated" refers to a substance that is separated from at least some other substances with which it is normally found in nature, usually by a process involving the hand of man, or is artificially produced, e.g., chemically synthesized, or present in an artificial environment.

"Nucleic acid" is used interchangeably with "polynucleotide" and encompasses naturally occurring polymers of nucleosides, such as DNA and RNA, usually linked by phosphodiester bonds, and non-naturally occurring polymers of nucleosides or nucleoside analogs. In some embodiments a nucleic acid comprises standard nucleotides (abbreviated A, G, C, T, U). In other embodiments a nucleic acid comprises one or more non-standard nucleotides. In some embodiments, one or more nucleotides are non-naturally occurring nucleotides or nucleotide analogs. A nucleic acid can comprise chemically or biologically modified bases (for example, methylated bases), modified sugars (2'-fluororibose, arabinose, or hexose), modified phosphate groups (for example, phosphorothioates or 5'-N-phosphoramidite linkages), locked nucleic acids, or morpholinos. In some embodiments, a nucleic acid comprises nucleosides that are linked by phosphodiester bonds. In some embodiments, at least some nucleosides are linked by a non-phosphodiester bond. A nucleic acid can be single-stranded, double-stranded, or partially double-stranded. An at least partially double-stranded nucleic acid can have one or more overhangs, e.g., 5' and/or 3' overhang(s). Nucleic acid modifications (e.g., nucleoside and/or backbone modifications), non-standard nucleotides, delivery vehicles and approaches, etc., known in the art as being useful in the context of RNA interference (RNAi), aptamer, or antisense-based molecules for research or therapeutic purposes are contemplated for use in various embodiments of the instant invention. See, e.g., Crooke, S T (ed.) Antisense drug technology: principles, strategies, and applications, Boca Raton: CRC Press, 2008; Kurreck, J. (ed.) Therapeutic oligonucleotides, RSC biomolecular sciences. Cambridge: Royal Society of Chemistry, 2008. A nucleic acid may comprise a detectable label, e.g., a fluorescent dye, radioactive atom, etc. "Oligonucleotide" refers to a relatively short nucleic acid, e.g., typically between about 4 and about 60 nucleotides long.

A "polypeptide" refers to a polymer of amino acids linked by peptide bonds. A protein is a molecule comprising one or more polypeptides. A peptide is a relatively short polypeptide, typically between about 2 and 60 amino acids in length. The terms "protein", "polypeptide", and "peptide" may be used interchangeably. Polypeptides of interest herein often contain standard amino acids (the 20 L-amino acids that are most commonly found in nature in proteins). However, other amino acids and/or amino acid analogs known in the art can be used in certain embodiments of the invention. One or more of the amino acids in a polypeptide (e.g., at the N- or C-terminus or in a side chain) may be modified, for example, by addition, e.g., covalent linkage, of a moiety such as an alkyl group, carbohydrate group, a phosphate group, a halogen, a linker for conjugation, etc. A polypeptide sequence presented herein is presented in an N-terminal to C-terminal direction unless otherwise indicated. "Polypeptide domain" refers to a segment of amino acids within a longer polypeptide. A polypeptide domain may exhibit one or more discrete binding or functional properties, e.g., a catalytic activity. Often a domain is recognizable by its conservation among polypeptides found in multiple different species.

As used herein, the term "purified" refers to agents or entities (e.g., compounds) that have been separated from most of the components with which they are associated in nature or when originally generated. In general, such purification involves action of the hand of man. Purified agents or entities may be partially purified, substantially purified, or pure. Such agents or entities may be, for example, at least 50%, 60%, 70%, 75%, 80%, 85%, 90%, 95%, 96%, 97%, 98%, 99%, or more than 99% pure. In some embodiments, a nucleic acid or polypeptide is purified such that it constitutes at least 75%, 80%, 855%, 90%, 95%, 96%, 97%, 98%, 99%, or more, of the total nucleic acid or polypeptide material, respectively, present in a preparation. Purity can be based on, e.g., dry weight, size of peaks on a chromatography tracing, molecular abundance, intensity of bands on a gel, or intensity of any signal that correlates with molecular abundance, or any art-accepted quantification method. In some embodiments, water, buffers, ions, and/or small molecules (e.g., precursors such as nucleotides or amino acids), can optionally be present in a purified preparation. A purified molecule may be prepared by separating it from other substances (e.g., other cellular materials), or by producing it in such a manner to achieve a desired degree of purity. In some embodiments, a purified molecule or composition refers to a molecule or composition that is prepared using any art-accepted method of purification. In some embodiments "partially purified" means that a molecule produced by a cell is no longer present within the cell, e.g., the cell has been lysed and, optionally, at least some of the cellular material (e.g., cell wall, cell membrane(s), cell organelle(s)) has been removed.

"RNA interference" (RNAi) encompasses processes in which an endogenous molecular complex known as an RNA-induced silencing complex (RISC) silences gene expression in a sequence-specific manner. The RISC contains a short RNA strand that directs or "guides" sequence-specific degradation or translational repression of mRNA to which it has complementarity. The complementarity between the short RNA and mRNA need not be perfect (100%). For example, the degree of complementarity and/or the characteristics of the structure formed by hybridization of the mRNA and the short RNA strand can be such that the strand can (i) guide cleavage of the mRNA in the RNA-induced silencing complex (RISC) and/or (ii) cause translational repression of the mRNA by RISC. It will be appreciated that one or more mismatches between the guide strand and the target mRNA can be tolerated, especially outside the seed region (the nucleotides in positions 2-7 or 2-8) of the guide strand. A short RNA that guides silencing often initially becomes associated with RISC components (in a complex sometimes termed the RISC loading complex) as part of a short double-stranded RNA (dsRNA). RNAi is often used to knockdown a target gene. "Knockdown" typically refers to a reduction in expression, which may occur, e.g., at the level of transcription, mRNA stability, translation, or protein stability. Reduction can be complete (e.g., the amount of gene product is reduced to background levels) or less than complete. For example, mRNA and/or protein level can be reduced by 50%, 60%, 70%, 75%, 80%, 85%, 90%, or more.

RNAi may be employed to inhibit expression in eukaryotic cells, e.g., vertebrate cells, in a variety of ways as known in the art. In some embodiments, a short double-stranded nucleic acid is introduced into cells. In some embodiments, a nucleic acid that is processed intracellularly (e.g., by one or more RNase III family enzymes Dicer) to yield short dsRNA is introduced into or expressed in cells. As used herein, the term "RNAi agent" encompasses nucleic acids that can be used to achieve RNAi in eukaryotic cells. Exemplary RNAi agents are short interfering RNA (siRNA) and short hairpin RNA (shRNA). As known in the art, siRNAs typically comprise two separate nucleic acid strands that are hybridized to each other to form a duplex. They can be synthesized in vitro, e.g., using standard nucleic acid synthesis techniques or by cleavage of a longer dsRNA, e.g., by an RNase III or RNase III-like enzyme such as Dicer. In certain embodiments an siRNA or shRNA comprises a duplex portion about 15-29 nucleotides (nt) long, e.g., between 17-25 nt long, e.g., between 19-23 nt long, wherein either or both strands optionally has a 3' overhang of 1-5 nucleotides long (e.g., 2 nucleotides), which may be composed of deoxyribonucleotides. In some embodiments, the strands are perfectly complementary within the duplex portion, while in other embodiments, the duplex portion could contain one or more mismatched nucleotide pairs or bulges. In some embodiments, each strand of an siRNA is between 15-29 nucleotides in length, e.g., between 19-25 nt long, e.g., 21-23 nt long. shRNA comprise a single nucleic acid strand that contains two complementary portions separated by a predominantly non-self-complementary region. The complementary portions hybridize to form a duplex structure and the non-self-complementary region forms a loop connecting the 3' end of one strand of the duplex and the 5' end of the other strand. shRNAs can undergo intracellular processing to generate siRNAs.

RNAi agents also include microRNA (miRNA) and miRNA precursors. The terms "miRNA" and "miRNA precursor" are often used in the art to refer to endogenously encoded RNAs. As used herein, "miRNA" and "miRNA precursor" encompasses artificially designed nucleic acids that function in an analogous manner to endogenous miRNAs.

In certain embodiments an RNAi agent is a vector that comprises a template for transcription of an siRNA (e.g., as two separate strands that can hybridize to each other), shRNA, or microRNA precursor. Such vectors can be used to introduce the template into vertebrate cells, e.g., mammalian cells, and result in transient or stable expression of the siRNA, shRNA, or miRNA precursor.

A "small molecule" as used herein, is an organic molecule that is less than about 2 kilodaltons (KDa) in mass. In some embodiments, the small molecule is less than about 1.5 KDa, or less than about 1 KDa. In some embodiments, the small molecule is less than about 800 daltons (Da), 600 Da, 500 Da, 400 Da, 300 Da, 200 Da, or 100 Da. Often, a small molecule has a mass of at least 50 Da. In some embodiments, a small molecule is non-polymeric. In some embodiments, a small molecule is not an amino acid. In some embodiments, a small molecule is not a nucleotide. In some embodiments, a small molecule is not a saccharide. In some embodiments, a small molecule contains multiple carbon-carbon bonds and can comprise one or more heteroatoms and/or one or more functional groups important for structural interaction with proteins (e.g., hydrogen bonding), e.g., an amine, carbonyl, hydroxyl, or carboxyl group, and in some embodiments at least two functional groups. Small molecules often comprise one or more cyclic carbon or heterocyclic structures and/or aromatic or polyaromatic structures, optionally substituted with one or more of the above functional groups.

A "subject" can be any multicellular organism, e.g., a multicellular organism that is susceptible to infection by a virus or is or may be infected by a virus. Often at least some of the cells of the subject express detectable amounts of PLA2G16. In some embodiments a subject is an animal, e.g., a vertebrate, e.g., a mammal or avian. Exemplary mammals include, e.g., humans, non-human primates, rodents (e.g., mouse, rat, rabbit), ungulates (e.g., ovine, bovine, equine, caprine species), canines, and felines. In some embodiments, the animal is a mammal of economic importance, such as a cow, horse, pig, goat, or sheep. Often, a subject is an individual to whom a compound is to be delivered, e.g., for experimental, diagnostic, and/or therapeutic purposes or from whom a sample is obtained or on whom a diagnostic procedure is performed (e.g., a sample or procedure that will be used to determine whether the subject has a viral infection or is at risk of a viral infection).

"Treat", "treating" and similar terms refer to providing medical and/or surgical management of a subject. Treatment can include, but is not limited to, administering a compound or composition (e.g., a pharmaceutical composition) to a subject. Treatment is typically undertaken in an effort to alter the course of a disease, disorder, or undesirable condition in a manner beneficial to the subject. The effect of treatment can generally include reversing, alleviating, reducing severity of, delaying the onset of, curing, inhibiting the progression of, and/or reducing the likelihood of occurrence or reoccurrence of the disease, disorder, or condition to which such term applies, or one or more symptoms or manifestations of such disease, disorder or condition. A composition of this invention can be administered to a subject who has developed an infection or is at increased risk of developing an infection relative to a member of the general population. A composition of this invention can be administered prophylactically, before development of any symptom or manifestation of a condition. Typically in this case the subject will be at risk of developing the condition. For example, an inventive composition can be administered prior to exposure of the subject to an infectious agent or prior to the occurrence of a pathogenic event, "Preventing" can refer to administering a compound or composition (e.g., a pharmaceutical composition) to a subject who has not developed a disease or condition, so as to reduce the likelihood that the disease or condition will occur or so as to reduce the severity of the disease or condition should it occur. The subject may be identified as at risk of developing the disease or condition (e.g., at increased risk relative to many most other members of the population or as having a risk factor that increases likelihood of developing the disease).

II. Overview

The present invention relates in part to the identification of phospholipase A2, group XVI (PLA2G16) as a new molecular target of use for identification and/or characterization of antiviral compounds. PLA2G16 is a phospholipase that is widely or ubiquitously expressed in mammalian tissues. It has now been discovered that PLA2G16 polypeptide is a host cell factor that plays an important role in infection of vertebrate cells, e.g., mammalian cells, by viruses of the Picornavirus family. The invention encompasses the recognition that inhibiting PLA2G16 inhibits viral infection. As described in more detail in the Examples, using a gene trap mutagenesis strategy in a near-haploid mammalian cell line (the HAP1 cell line), it was shown that insertions into the PLA2G16 gene (located on chromosome 11 in human cells) rendered the cells resistant to infection by poliovirus and Coxsackie virus B1. Restoring wild type PLA2G16 function by expressing wild type PLA2G16 in the cells restored susceptibility to infection, while expressing a catalytically inactive mutant version of PLA2G16 did not. Furthermore, knockdown of endogenous PLA2G16 expression in a rhinovirus-sensitive cell line (HeLa cells) using short interfering RNA (siRNA) rendered these cells resistant to rhinovirus infection. The discoveries described herein indicate that PLA2G16 is required for infection of vertebrate cells by a wide range of viruses.

The invention provides compositions and methods for inhibiting viral infection. The invention further provides compositions and methods useful for identifying candidate compounds for inhibiting viral infection. In some aspects, the compositions and methods relate to the use of the PLA2G16 gene and/or PLA2G16 polypeptide as targets for identification of antiviral compounds (i.e., compounds that inhibit viral infection). Certain of the inventive methods comprise identifying or providing a compound that inhibits PLA2G16. In accordance with certain embodiments of the invention, a compound that inhibits PLA2G16 is a candidate antiviral compound. Certain of the inventive methods comprise (i) identifying or providing a compound that inhibits PLA2G16; and (ii) determining whether the compound inhibits viral infection of a cell or multicellular organism, wherein if the compound inhibits viral infection of a cell or multicellular organism, the compound is an antiviral compound. In some embodiments, a compound that inhibits PLA2G16 inhibits PLA2G16 expression. In some embodiments, a compound that inhibits PLA2G16 inhibits a PLA2G16 molecular function, e.g., the compound inhibits PLA2G16 catalytic activity.

Inhibiting viral infection can comprise interventions that inhibit one or more steps of the viral life cycle so that, for example, there is reduced entry of virus into cells, reduced production of viral gene product(s) (viral RNAs and/or proteins), reduced production of progeny virus, reduced release of progeny virus, and/or reduced spread of virus within a population of cells (e.g., in cell culture or in a multicellular organism) as compared with an appropriate reference level, e.g., the level that would exist in the absence of the intervention. Inhibition of viral infection can be assessed based on any of a variety of suitable indicators. In some embodiments, inhibition of an indicator of viral infection is complete or substantially complete, e.g., an indicator of viral infection such as production of a viral gene product, production of progeny virus, infection of additional cells, is reduced to background or undetectable level, e.g., a level that would be expected in the absence of the virus. In some embodiments, inhibition is not complete. In some embodiments, inhibition of viral infection can refer to a reduction by about a factor of at least 10, at least $10^2$, at least $10^3$, at least $10^4$, or more, e.g., in production of progeny virus or of a viral gene product.

In some aspects, the invention provides methods of inhibiting viral infection of a cell. In some aspects, the methods comprise inhibiting PLA2G16 in a cell, thereby inhibiting viral infection of the cell. In some embodiments, the methods comprise contacting a cell with a compound that inhibits PLA2G16, so that viral infection of the cell is inhibited. In some embodiments, the cell is an animal cell, e.g., a vertebrate cell. In some embodiments, the vertebrate cell is a mammalian cell. In some aspects, the invention provides methods of inhibiting viral infection of a subject. In some embodiments, the subject is a vertebrate. In some aspects, the methods comprise inhibiting PLA2G16 in at least some cells of the organism, e.g., at least some cells that are infected by a virus or are susceptible to infection by a virus. In some embodiments, the methods comprise administering a compound that inhibits PLA2G16 to the subject. In some embodiments, the subject is an animal, e.g., a vertebrate. In some embodiments, the vertebrate is a mammal.

In some aspects, the invention provides methods of decreasing the susceptibility (or increasing the resistance) of a cell or subject to a virus, the methods comprising inhibiting PLA2G16 in a cell or in at least some cells of the subject. Thus the invention provides methods of reducing the vulnerability or propensity of a cell or subject to become infected and/or to experience adverse effects due to a virus. "Resistance" to a virus typically refers to the ability to defend against infection. For purposes of description, the invention will mainly be described in terms of inhibiting virus infection. However, it will be understood that, unless otherwise indicated, the inventive methods of inhibiting virus infection of a cell or subject could be described as inhibiting susceptibility of the cell or subject to virus infection or increasing resistance of the cell or subject to virus infection.

In some aspects, the invention provides methods of selecting a therapeutic agent for a subject, the method comprising (a) determining whether the subject is infected by a virus for which PLA2G16 is a host cell factor; and (b) selecting a compound that inhibits PLA2G16 as a therapeutic agent for the subject if the subject is infected by a virus for which PLA2S16 is a host cell factor. In some embodiments, the method further comprises administering a compound that inhibits PLA2G16 to the subject.

In some aspects, the invention provides methods of determining whether a subject is a candidate for treatment with a compound that inhibits PLA2G16. In some embodiments, the method comprises determining whether the subject is infected by, or at risk of infection by, a virus for which PLA2G16 is a host cell factor, wherein if the subject is infected by a virus for which PLA2G16 is a host cell factor, the subject is a candidate for treatment with a compound that inhibits PLA2G16. In some embodiments, the method comprises determining whether the subject is infected by, or at risk of infection by, a picornavirus, wherein if the subject is infected with a picornavirus, the subject is a candidate for treatment with a compound that inhibits PLA2G16. In some embodiments, the method further comprises administering a compound that inhibits PLA2G16 to the subject.

In some aspects, the invention provides methods of treating a subject in need of treatment for a viral infection. In some embodiments, the methods comprise selecting a compound that inhibits PLA2G16 as a therapeutic agent for the subject. In some embodiments, the methods comprise administering a compound that inhibits PLA2G16 to the subject. In some embodiments, the methods of treatment comprise providing a subject in need of treatment for a viral infection. In some embodiments, the methods of treatment comprise diagnosing a subject as being infected with a virus. The subject may have one or more symptoms or signs of a viral infection, e.g., one or more symptoms or signs associated with a pathological state resulting from infection by a virus. In some embodiments, the method comprises administering a pharmaceutical composition comprising the compound to the subject. "Administration" can comprise direct administration or indirect administration. "Indirect" administration comprises activities such as providing, prescribing, directing another individual to administer, or in any way making a compound available to a subject.

III. Viruses and Viral Diseases

In some aspects, the invention relates to inhibiting infection of a cell or subject by a virus, wherein PLA2G16 promotes or plays a role in one or more steps of the life cycle of the virus. In some embodiments, the virus is capable of infecting cells of one or more animal species, e.g., one or more vertebrate species, e.g., mammalian or avian species, wherein the cells express PLA2G16. In various embodiments, the invention may be applied to any virus whose capacity to infect a cell, e.g., an animal cell, is reduced if PLA2G16 is inhibited. While the invention is described herein mainly in reference to certain viruses of interest, embodiments of the invention can be applied to any virus wherein expression of a PLA2G16 polypeptide in the cell promotes or plays a role in one or more steps of the viral life cycle. In some embodiments, the virus is of medical importance, e.g., it is recognized in the medical art as a causative agent of one or more diseases that affect humans. In some embodiments, the virus is of veterinary importance, e.g., it is recognized in the veterinary art as a causative agent of one or more diseases that affect non-human animals. See, e.g., Knipe & Howley, supra; Büchen-Osmond, C. supra, and Virus Descriptions in "ICTVdB—The Universal Virus Database", supra for discussion of various virus families, including viruses of medical and/or veterinary importance.

In some embodiments, the virus has a single-stranded RNA (ssRNA) genome. In some embodiments, the ssRNA genome virus is positive stranded. In some embodiments, the virus is a non-enveloped virus and/or has an icosahedral virion or nucleocapsid morphology. In some embodiments, the virus is a member of the picornavirus-like superfamily (such viruses are also termed "picorna-like viruses" herein). Viruses of the picornavirus-like superfamily are positive-sense ssRNA viruses that are characterized by a partially conserved set of genes that consists of an RNA dependent RNA polymerase (RdRp), a chymotrypsin-like protease (3CPro), a superfamily 3 helicase (S3H) and a genome-linked protein (viral protein, genome linked, VPg). The picornavirus-like superfamily encompasses the proposed order Picornavirales (discussed below) as well as various virus genera and families falling outside the proposed order, including, e.g., Caliciviridae and Astroviridae. See, e.g., Koonin, E V, et al., Nature Reviews Microbiology, 6:925-939, 2008.

In some embodiments, the virus is a member of the proposed order Picornavirales. This order includes viruses that infect eukaryotes and that share the following properties: (i) a positive-sense RNA genome, usually with a 5'-bound VPg and 3'-polyadenylated, (ii) genome translation into autoproteolytically processed polyprotein(s), (iii) capsid proteins organized in a module containing three related jelly-roll domains which form small icosahedral, non-enveloped particles with a pseudo-T=3 symmetry, and (iv) a three-domain module containing a superfamily iii helicase, a (cysteine) proteinase with a chymotrypsin-like fold and an RNA-dependent RNA polymerase. According to these criteria, the order Picornavirales includes the families Picornaviridae, Comoviridae, Dicistroviridae, Marnaviridae, Sequiviridae and the genera Cheravirus, Iflavirus and Sadwavirus. Other taxa of "picorna-like" viruses, e.g. Potyviridae, Caliciviridae, Hypoviridae, do not conform to several of the above criteria and are more remotely related. The family Caliciviridae is composed of small (27-40 nm), nonenveloped, icosahedral viruses and include the four genera Norovirus, Sapovirus, Vesivirus, and Lagovirus. The major pathogens of medical importance are the noroviruses, which are a major cause of acute gastroenteritis. Important veterinary pathogens include vesirivurses such as feline calicivirus (FCV) and rabbit hemorrhagic disease virus (RHDV). The family Astroviridae includes human and animal astroviruses that have icosahedral morphology and a characteristic starlike surface structure when viewed by electron microscopy. They are important agents of gastroenteritis and diarrhea in humans as well as various animals, including mammals (e.g., pigs) and avians.

In some embodiments of particular interest, the invention relates to inhibiting infection by viruses that are members of the Picornaviridae family (also termed "picornaviruses" or "Picornaviruses" herein). Picornaviruses (like other members of the picornavirus-like superfamily) are nonenveloped viruses with a single-stranded genome of positive polarity. They share a common genomic organization with a long 5' untranslated region (UTR) (e.g., at least about 500 nucleotides (nt) up to about 1200 nt long) containing an internal ribosome entry site (IRES), a single open reading frame (ORF) encoding a polyprotein that is proteolytically processed, and a short 3' UTR followed by a polyA tail (Knipe & Howley, supra). Major distinguishing features among different picornaviruses include, among others, the secondary structure of the 5' UTR and IRES.

The picornavirus family includes twelve genera: Aphthovirus, Avihepatovirus, Cardiovirus, Enterovirus, Erbovirus, Hepatovirus, Kobovirus, Parechovirus, Sapelovirus, Senecavirus, Teschovirus, and Tremovirus (see, "ICTVdB—The Universal Virus Database", Virus Taxonomy: 2009 Release v4, supra). A virus that is a members of one of these genera may be referred to as anaphthovirus, avihepatovirus, cardiovirus, enterovirus, erbovirus, hepatovirus, kobovirus, parechovirus, rhinoviruses, sapelovirus, senecavirus, teschovirus, or tremovirus, respectively These genera include numerous viruses that infect vertebrates, and a number of them contain members that are important causes of disease in humans and/or in non-human animals. For example, aphthoviruses include foot-and-mouth disease viruses, which infect cloven-footed animals such as cattle, goats, pigs, and sheep. Cardioviruses include two distinct clusters, the first of which includes encephalomyocarditisvirus and the second of which includes Theiler's murine encephalomyelitis virus and related viruses, including some that infect humans.

Human enteroviruses are common causes of mild upper respiratory symptoms and flu-like illnesses, among others. Less commonly, they can result in more serious conditions such as viral meningitis, myocarditis, or central nervous system conditions such as encephalitis. The Enterovirus genus includes the following 10 species, as set forth by the ICTV in its 2009 release (available on the World Wide Web): Human enterovirus A, Human enterovirus B, Human enterovirus C, Human enterovirus D, Simian enterovirus A, Bovine enterovirus, Porcine enterovirus B, Human rhinovirus A, Human rhinovirus B and Human rhinovirus C. Many of these species encompass multiple serotypes, which can in turn include multiple strains. The Human enterovirus species collectively encompass polioviruses, coxsackievirus, echoviruses, and numerous other enteroviruses that infect humans. The Enterovirus genus also encompasses numerous nonhuman enteric viruses. The poliovirus serotypes poliovirus (PV)-1, PV-2, and PV-3 are included within the Human enterovirus C species. Although poliovirus has been largely eradicated through widespread use of effective vaccines, other viruses within the Enterovirus genus are frequent causes of acute and chronic human diseases.

Coxsackieviruses are divided into group A and group B viruses based on early observations of their pathogenicity in mice. Coxsackieviruses are associated with a range of diseases in human including aseptic meningitis, hand-foot-mouth disease, herpangina, myocarditis (sometimes leading to cardiomyopathy), and pancreatitis, and may be an etiologic factor in type I diabetes (See, e.g., articles in Curr Top Microbiol Immunol. Vol. 323, 2008). Coxsackieviruses are classified among the Human enterovirus A, Human enterovirus B, and Human enterovirus C species. Exemplary coxsackieviruses include serotypes CV-A2, CV-A3, CV-A4, CV-A5, CV-A6, CV-A7, CV-A8, CV-A10, CV-A12, CV-A14, CV-A16, CV-B1, CV-B2, CV-B3, CV-B4, CV-B5, CV-B6, CV-A9, CV-A1, CV-A11, CV-A13, CV-A17, CV-A19, CV-A20, CV-A21, CV-A22, CV-A24.

Human enterovirus A, Human enterovirus B, Human enterovirus C, and Human enterovirus D species include additional enteroviruses such as serotypes EV-71, EV-76, EV-89, EV-90, EV-91, EV-92, EV-69, EV-73, EV-74, EV-75, EV-77, EV-78, EV-79, EV-80, EV-81, EV-82, EV-83, EV-84, EV-85, EV-86, EV-87, EV-88, EV-93, EV-97, EV-98, EV-100, EV-101, EV-106, EV-107, EV-95, EV-96, EV-99, EV-102, EV-104, EV-105, EV-109, EV-68, EV-70, and EV-94. For example, enterovirus 71 (EV-71) is a pathogenic enterovirus serotype that causes recurrent outbreaks in different parts of the world. It can infect the central nervous system and may cause death and long-term neurological sequelae in humans, especially infants and young children (Lin, Y-W., et al., Journal of Virology, 83(13): 6477-6483, 2009, and references therein). EV-71 may also cause diarrhea, rashes, and hand, foot and mouth disease.

Member of Human rhinovirus A and Human rhinovirus B species ("rhinoviruses") replicate in the nasopharynx and sometimes in the lower respiratory tract. These viruses (of which more than 100 serotypes exist) are important etiologic agents of the common cold in humans and can cause more severe disease as well, particularly in susceptible individuals.

The Teschovirus genus includes porcine teschovirus, which causes polioencephalitis in pigs. Hepatoviruses include human hepatitis A virus (HAV), which causes hepatitis A, an acute liver infection.

Additional picornaviruses continue to be discovered. See, e.g., Kapoor, A., et al., A highly prevalent and genetically diversified Picornaviridae genus in South Asian children. Proc Natl Acad Sci USA. 105(51):20482-7, 2008, describing members of the proposed cosavirus genus. More recently, a novel virus which has been designated as klassevirus was discovered using high throughput sequencing (see, e.g., Greninger, A L, et al., The complete genome of klassevirus—a novel picornavirus in pediatric stool, Virol J., 6:82-2009).

Those of skill in the art will appreciate that virus taxonomy and classification continue to evolve and that viruses can be reclassified, e.g., as additional viruses are discovered or studied, e.g., as viral genes are sequenced, and/or as relationships between viruses become evident. Thus certain viruses may have been reclassified by the ICTV subsequent to publication of certain references cited herein and/or may be reclassified in the future. Furthermore, those of skill in the art will appreciate that many publications and references relating to viruses do not adhere to conventions established by the ICTV, may have preceded the establishment of these conventions, and/or may employ formal and/or informal vernacular nomenclature. Identifying characteristics of viruses (and strains and variants thereof) are well established and known in the art. Characterized reference samples of numerous viruses are deposited in and typically available from various internationally recognized biological resource centers or culture collections such as the American Type Culture Collection (ATCC) (Manassas, Va.), National Collection of Pathogenic Viruses (NCPV) of the Health Protection Agency Culture Collections of the Health Protection Agency of the United Kingdom (Porton Down Salisbury UK; available on the World Wide Web) and/or internationally recognized specialty groups, as are reagents of use to identify and/or characterize viruses. Characterization and/or classification can be based on properties such as nucleic acid and/or polypeptide sequences, reactivity with immunological reagents (e.g., antisera), etc. Genome sequences of numerous enteroviruses, including those of numerous human enteroviruses, are publicly available, e.g., on the website of the European Bioinformatics Institute, National Center for Biotechnology Information, and in the scientific literature.

Picornavirus structure and life cycle have been extensively studied (see, e.g., Knipe & Howley, supra). Briefly, the picornavirus capsid is typically composed of four structural proteins: VP1, VP2, VP3 and VP4. (Parechoviruses contain only VP1, VP2, and VP0, the uncleaved precursor of VP2+VP4). The basic building block of the picornavirus capsid, termed the protomer, contains one copy of VP1, VP2, VP3, and VP4. VP1, VP2, and VP3 form a shell with VP4 on its inner surface. Differences in the amino acid sequences of certain portions of VP1, VP2, and VP3 give different picornaviruses distinct morphologies and antigenicities.

Replication of picornaviruses occurs in the cell cytoplasm. Picornaviruses initiate infection by attaching to a receptor on the host cell membrane, which is followed by uncoating and entry of the viral genome into the cytoplasm. The poliovirus receptor (PVR, CD155) and the major group rhinovirus (ICAM-1) were identified in 1989, and since that time receptors for a number of other picornaviruses have been identified. Some picornaviruses typically require co-receptors for infection. For example, many enteroviruses bind to decay-accelerating factor (DAF; CD55) but infection typically requires presence of an additional molecule, e.g., ICAM-1 or an integrin family member. The RNA genome is translated on entry into the cytoplasm to a single polyprotein that is cleaved during translation by virus-encoded proteases (mainly 2Apro and C3pro or 3CDpro) to produce all the viral proteins needed for viral replication. Some of the uncleaved precursors also have functions during viral replication. Among the viral proteins synthesized are the viral RNA-dependent RNA polymerase and accessory proteins required for genome replication and mRNA synthesis. The first step of genome replication is copying of the positive-stranded RNA to generate a negative-stranded intermediate, which is used as a template for synthesis of additional positive strands. Encapsidation begins once sufficient capsid proteins have accumulated.

Many picornaviruses produce characteristic morphologic changes termed "cytopathic effects" in infected cells. Cytopathic effects can include chromatin condensation, nuclear blebbing, proliferation of membranous vesicles, leakage of intracellular contents, and shriveling of the entire cell. In the case of many picornavirus species, virions are released from infected cells as a consequence of cell lysis. Other picornaviruses (e.g., hepatitis A virus) are released from cells in the absence of cell lysis. In some embodiments of the invention, cytopathic effect(s) and/or virion release is assessed to determine whether a cell or subject is infected with a virus. In some embodiments, cytopathic effect(s) and/or virion release is assessed to determine whether a compound inhibits a virus infection.

IV. PLA2G16 Polypeptides

PLA2G16 is an ~18 kilodalton protein that is highly expressed in vertebrate adipose tissue (especially white adipose tissue) and is also expressed at lower levels in a wide variety of vertebrate tissues and cultured cell lines. PLA2G16 is also known as adipose-specific phospholipase A2 (AdPLA), HRAS-like suppressor 3 (HRASLA3), and by several other names. One of skill in the art will readily be able to obtain PLA2G16 genomic and mRNA sequences and the PLA2G16 protein from publicly available databases. The human gene encoding PLA2G16 has been assigned GeneID: 11145 in the Gene database of the National Center for Biotechnology Information (NCBI; www.ncbi.nlm.nih.gov). Genes encoding PLA2G16 from mouse and rat have been assigned the following Gene IDs: Gene ID: 225845 (*Mus musculus*); Gene ID: 24913 (*Rattus norvegicus*). One of skill in the art will readily be able to obtain the sequences of PLA2G16 mRNA and protein from these and other species. For example, accession numbers for the human PLA2G16 mRNA and protein Reference Sequences available at the NCBI are as follows: NM_001128203 (transcript variant 2) and NP_001121675 (protein). NM_007069.3 (transcript variant 1) and NP_009000.2 (protein). Transcript variant 1 represents the longer transcript. Variants 1 and 2 encode the same isoform but differ in the 5' untranslated region (UTR).

PLA2G16 has phospholipase activity and significantly lower but detectable lysophospholipase activity (Duncan, R E, et al., J Biol Chem., 283(37):25428-36, 2008). $PLA_2$ proteins are enzymes that catalyze hydrolysis of the sn-2 bond of phospholipids (Schaloske, R H and Dennis, E A, *Biochim. Biophys. Acta* 1761, 1246-1259, 2006). PLA2G16 was shown to generate free fatty acid and lysophospholipid from phosphatidylcholine with a preference for hydrolysis at the sn-2 position, suggesting that the protein is a $PLA_2$ (Duncan, supra). PLA2G16 was found in association with intracellular membranes and has a C-terminal presumed membrane spanning domain whose deletion caused a loss of activity. Mutational analysis showed that certain highly conserved amino acids, including His-23, Cys-113, Gln-129 and Asn-112, were essential for catalysis, but that mutation of Asp-30 or His-80 to alanine had no effect. Thus PLA2G16 appears to contain His and Cys active catalytic residues rather than a His/Asp catalytic diad or a Ser/His/Asp catalytic triad as found in some other $PLA_2$s. Calcium was found to activate PLA2G16 but is not essential for activity. Since PLA2G16 does not fit clearly into any of the previously identified 15 major groups of $PLA_2$ it was proposed to be the first member of a distinct group of calcium-dependent phospholipase $A_2$s (Group XVI) (Duncan, supra).

PLA2G16 is also known in the art as adipocyte phospholipase A2 (AdPLA) (Jaworski, K., et al. Nat Med., 15(2):159-68, 2009). It is the major $PLA_2$ in adipose tissue and plays an important role in regulating adipocyte lipolysis. PLA2G16 null mice were viable and had normal weight at weaning but gained weight more slowly than wild-type littermates despite having equivalent food intakes (Jaworski, K., supra). By standard pathology analysis PLA2G16 null mice showed no evidence of any gross, microscopic, or functional abnormalities, aside from reduced adiposity. Blood cell profile and immunological parameters in serum and adipose tissue were not changed in these mice compared to wild-type mice. These results suggest that methods of the present invention that comprise inhibiting PLA2G16 in order to inhibit viral infection are likely to be well tolerated in isolated cells and in subjects of interest, e.g., humans and other vertebrates.

In some embodiments, a "PLA2G16 polypeptide" is a polypeptide whose sequence comprises or consists of the sequence of a PLA2G16 polypeptide of a multicellular organism (e.g., a vertebrate, e.g., a mammal, such as a human, mouse, rat, bovine, etc.). A naturally occurring PLA2G16 polypeptide or a polypeptide identical in sequence to a naturally occurring PLA2G16 polypeptide is referred to as a "native PLA2G16 polypeptide" or simply "PLA2G16" herein. Exemplary native PLA2G16 polypeptides are depicted in FIG. 8 and under the accession numbers mentioned above. In some embodiments, a PLA2G16 polypeptide is a variant of PLA2G16 ("PLA2G16 variant"). PLA2G16 variants include polypeptides that differ by one or more amino acid substitutions, additions, or deletions, relative to PLA2G16. An addition can be an insertion within the polypeptide or an addition at the N- or C-terminus. In some embodiments, the number of amino acids substituted, deleted, or added can be for example, about 1 to 30, e.g., about 1 to 20, e.g., about 1 to 10, e.g., about 1 to 5, e.g., 1, 2, 3, 4, or 5. In some embodiments, a PLA2G16 variant comprises a polypeptide whose sequence is homologous to the sequence of PLA2G16 over at least 50 amino acids, at least 100 amino acids, at least 150 amino acids, or over the full length of PLA2G16 (but is not identical in sequence to native PLA2G16). In some embodiments, a PLA2G16 variant comprises a polypeptide at least 70%, 75%, 80%, 85%, 90%, 95%, 96%, 97%, 98%, 99%, or more identical to PLA2G16 (e.g., from human, mouse, rat, dog, cow) over at least 50%, 60%, 70%, 80%, 85%, 90%, 95%, 96%, 97%, 98%, 99%, or 100% of PLA2G16. In some embodiments, a PLA2G16 variant comprises a polypeptide at least 80%, 85%, 90%, 95%, 96%, 97%, 98%, 99%, or more identical to at least amino acids 23-113 of human or mouse PLA2G16. In some embodiments, a PLA2G16 polypeptide comprises a polypeptide at least 80%, 85%, 90%, 95%, 96%, 97%, 98%, 99%, or more identical to at least amino acids 23-129 of human or mouse PLA2G16.

In some embodiments, a PLA2G16 polypeptide comprises or consists of a PLA2G16 fragment. A PLA2G16 fragment is a polypeptide that is shorter than PLA2G16 and is identical to PLA2G16 over the length of the shorter polypeptide. In some embodiments, a PLA2G16 fragment is at least 50%, 60%, 70%, 80%, 85%, 90%, 95%, 96%, 97%, 98%, or 99% as long as native PLA2G16. In some embodiments, a fragment consists of amino acids 23-113 or 23-129 of human or mouse PLA2G16. In some embodiments, one or more amino acids at the C-terminus are deleted. For example, in some embodiments at least the membrane spanning domain at the C-terminus is deleted. For example, in some embodiments, at least the C-terminal 30 amino acids are deleted. In some embodiments, one or more amino acids at the N-terminus are deleted.

In some embodiments, a PLA2G16 polypeptide comprises a heterologous polypeptide portion. The heterologous portion often has a sequence that is not present in or homologous to native PLA2G16. A heterologous portion may be, e.g., between 5 and about 5,000 amino acids long, or longer. Often it is between 5 and about 1,000 amino acids long. In some embodiments, a heterologous portion comprises a sequence that is found in a different polypeptide, e.g., a functional domain. In some embodiments, a heterologous portion comprises a sequence useful for purifying, expressing, solubilizing, and/or detecting the polypeptide. In some embodiments, a heterologous portion comprises a polypeptide "tag", e.g., an affinity tag or epitope tag. For example, the tag can be an affinity tag (e.g., HA, TAP, Myc, 6× His, Flag, GST), fluorescent or luminescent protein (e.g., EGFP, ECFP, EYFP, Cerulean, DsRed, mCherry), solubility-enhancing tag (e.g., a SUMO tag, NUS A tag, SNUT tag, or a monomeric mutant of the Ocr protein of bacteriophage T7). See, e.g., Esposito D and Chatterjee D K. Curr Opin Biotechnol.; 17(4):353-8 (2006). In some embodiments, a tag can serve multiple functions. A tag is often relatively small, e.g., ranging from a few amino acids up to about 100 amino acids long. In some embodiments a tag is more than 100 amino acids long, e.g., up to about 500 amino acids long, or more. In some embodiments, a PLA2G16 polypeptide has a tag located at the N- or C-terminus, e.g., as an N- or C-terminal fusion. The polypeptide could comprise multiple tags. In some embodiments, a 6× His tag and a NUS tag are present, e.g., at the N-terminus. In some embodiments, a tag is cleavable, so that it can be removed from the polypeptide, e.g., by a protease. In some embodiments, this is achieved by including a sequence encoding a protease cleavage site between the sequence encoding the portion homologous to PLA2G16 and the tag. Exemplary proteases include, e.g., thrombin, TEV protease, Factor Xa, PreScission protease, etc. In some embodiments, a "self-cleaving" tag is used. See, e.g., PCT/US05/05763. Sequences encoding a tag can be located 5' or 3' with respect to a polynucleotide encoding the polypeptide (or both). In some embodiments a tag or other heterologous sequence is separated from the rest of the polypeptide by a polypeptide linker. For example, a linker can be a short polypeptide (e.g., 15-25 amino acids). Often a linker is composed of small amino acid residues such as serine, glycine, and/or alanine. A heterologous domain could comprise a transmembrane domain, a secretion signal domain, etc.

In some embodiments, a PLA2G16 variant is a functional variant, i.e., the variant at least in part retains at least one biological activity of PLA2G16. In some embodiments, a functional variant retains sufficient activity to be distinguishable from a non-homologous protein or catalytically inactive PLA2G16 polypeptide (e.g., a PLA2G16 polypeptide having a C113A substitution) when used in an assay of the present invention. In some embodiments, the activity is phospholipase A2 activity, e.g., as measured by ability to catalyze hydrolysis of the sn-2 bond of phospholipids. In some embodiments, the activity is lysophospholipase activity. In some embodiments, a PLA2G16 variant retains the ability of native PLA2G16 to serve as a host cell factor for a virus. For example, the PLA2G16 variant has sufficient activity so that expressing it in a vertebrate cell that is resistant to viral infection because the cell's PLA2G16 gene is disabled (e.g., by a gene trap insertion) renders the cell sensitive to viral infection. In some embodiments, a functional PLA2G16 variant retains at least 10%, 20%, 30%, 40%, 50%, 60%, 70%, 80%, 90%, 95%, 96%, 97%, 98%, 99%, or more of the activity of PLA2G16, e.g., about equal activity. In some embodiments, a functional variant may have greater activity than PLA2G16.

One of skill in the art can readily generate functional PLA2G16 variants or fragments. As discussed above, considerable information is available regarding PLA2G16, including identification of various residues important for activity and various residues that may be altered without significantly decreasing activity, as well as alignments with other PLA2 polypeptides (see, e.g., Duncan, et al, supra). In some embodiments, a PLA2G16 variant comprises one or more conservative amino acid substitutions relative to PLA2G16. Conservative substitutions may be made on the basis of similarity in side chain size, polarity, charge, solubility, hydrophobicity, hydrophilicity and/or the amphipathic nature of the residues involved. As known in the art, such substitutions are, in general, more likely to result in a variant that retains activity as compared with non-conservative substitutions. In one embodiment, amino acids are classified as follows:
Special: C
Neutral and small: A, G, P, S, T
Polar and relatively small: N, D, Q, E
Polar and relatively large: R, H, K
Nonpolar and relatively small: I, L, M, V
Nonpolar and relatively large: F, W, Y
Special: C See, e.g., Zhang, J. J. Mol. Evol. 50:56-68, 2000). In some embodiments, proline (P) is considered to be in its own group as a second special amino acid. Within a particular group, certain substitutions may be of particular interest, e.g., replacements of leucine by isoleucine (or vice versa), serine by threonine (or vice versa), or alanine by glycine (or vice versa). Of course non-conservative substitutions are often compatible with retaining function as well. In some embodiments, a substitution or deletion does not alter or delete an amino acid important for activity, e.g., amino acid His-23, Cys-113, Gln-129 or Asn-112. In some embodiments, a deletion does not remove all or a substantial portion of the C-terminal 36 amino acids. For example, in some embodiments, a deletion does not remove the transmembrane domain. In some embodiments, an alteration is at an amino acid that differs among PLA2G16 of different species. In some embodiments, a substitution alters an amino acid to that present at a corresponding position in a different species. In some embodiments, a functional PLA2G16 variant comprises a polypeptide at least 95%, 96%, 97%, 98%, 99% or 100% identical to PLA2G16, e.g., over at least 70%, 75%, 80%, 85%, 90%, 95%, 96%, 97%, 98%, or 99% or 100% of the full length of PLA2G16. In some embodiments, a functional PLA2G16 variant comprises a polypeptide at least 95%, 96%, 97%, 98%, 99% or 100% identical to PLA2G16 e.g., over at least 70%, 75%, 80%, 85%, 90%, 95%, 96%, 97%, 98%, or 99% or 100% of the full length of PLA2G16, and comprises a tag at the N- and/or C-terminus. PLA2G16 variants could be tested in cell-free and/or cell-based assays to assess their activity.

In some embodiments, a variant or fragment of PLA2G16 that has substantially reduced activity as compared with the activity of native PLA2G16 (e.g., less than 10% of the activity of native PLA2G16) is useful as a PLA2G16 inhibitor or antiviral compound. For example, such polypeptide could interfere with the function of native PLA2G16 in viral infection, e.g., by competing with native PLA2G16. In some embodiments, a variant or fragment of PLA2G16 that has substantially reduced activity as compared with the activity of native PLA2G16 is useful a control or as an immunogen or for crystallization or binding studies.

A PLA2G16 polypeptide, e.g., a native PLA2G16 polypeptide or a PLA2G16 variant can be produced using standard recombinant DNA techniques. A nucleic acid encoding PLA2G16 can readily be obtained, e.g., from cells that express PLA2G16 (e.g., by PCR or other amplification methods or by cloning) or by synthesis based on a known PLA2G16 cDNA or polypeptide sequence. One of skill in the art would know that due to the degeneracy of the genetic code, numerous different nucleic acid sequences would encode the desired polypeptide. Optionally, a sequence is codon-optimized for expression in a host cell of choice. A nucleic that encodes a PLA2G16 variant can readily be generated, e.g., by modifying native PLA2G16 using, e.g., site-directed mutagenesis, or by other standard methods.

A nucleic acid encoding the desired polypeptide, operably linked to appropriate expression control elements, usually in a vector such as a plasmid or virus (e.g., as part of the viral genome), is introduced into prokaryotic or eukaryotic cells. In other embodiments, a PLA2G16 polypeptide is produced using in vitro translation. Exemplary cells include, e.g., bacterial cells (e.g., E. coli), insect cells, mammalian cells, plant cells, fungal cells (e.g., yeast). One of skill in the art will be aware of suitable expression control elements (e.g., promoters). Promoters may be constitutive or regulatable, e.g., inducible or repressible. Exemplary promoters suitable for use in bacterial cells include, e.g., Lac, Trp, Tac, araBAD (e.g., in a pBAD vectors), phage promoters such as T7 or T3. Exemplary expression control sequences useful for directing expression in mammalian cells include, e.g., the early and late promoters of SV40, adenovirus or cytomegalovirus immediate early promoter, or viral promoter/enhancer sequences, retroviral LTRs, promoters or promoter/enhancers from mammalian genes, e.g., actin, EF-1 alpha, metallothionein, etc. The polyhedrin promoter of the baculovirus system is of use to express proteins in insect cells. One of skill in the art will be aware of numerous expression vectors that contain appropriate expression control element(s), selectable markers, cloning sites, etc., and can be conveniently used to express a polypeptide of interest. Optionally, such vectors include sequences encoding a tag, to allow convenient production of a polypeptide comprising a tag. Suitable methods for introducing vectors into bacteria, yeast, plant, or animal cells (e.g., transformation, transfection, infection, electroporation, etc.), and, if desired, selecting cells that have taken up the vector and deriving stable cell lines. Transgenic animals or plants that express the polypeptide could be produced using methods known in the art.

To produce a PLA2G16 polypeptide, cells are maintained in culture for a suitable time period, and the polypeptide is isolated and optionally further purified. (Of course a PLA2G16 polypeptide could also be isolated from cells or tissues obtained directly from an organism that expresses it.) Standard protein isolation/purification techniques can be used. In some embodiments, affinity-based methods are used. For example, an antibody to PLA2G16 can be employed. In the case of tagged PLA2G16 polypeptides, an appropriate isolation method can be selected depending on the particular tag used.

V. Compositions and Methods for Inhibiting PLA2G16

The term "PLA2G16 inhibitor" refers to a compound that inhibits PLA2G16 expression and/or inhibits one or more activities of PLA2G16. For example, a compound is "PLA2G16 inhibitor" if one or more PLA2G16 activities is reduced in the presence of the compound as compared with its absence and/or if the level or amount of PLA2G16 protein or gene product is reduced in the presence of the compound as compared with its absence. In certain embodiments, PLA2G16 inhibitors act directly on PLA2G16 in the sense that they physically interact with PLA2G16. In other embodiments, inhibitors act indirectly on PLA2G16. A PLA2G16 inhibitor can be, e.g., a small molecule, nucleic acid, oligonucleotide, polypeptide, peptide, lipid, phospholipid, etc. In some embodiments, a PLA2G16 inhibitor is an RNAi agent, antisense oligonucleotide, aptamer, or antibody. In some embodiments, a PLA2G16 inhibitor is a small molecule.

The invention provides a number of different methods of inhibiting PLA2G16. As used herein, methods of inhibiting PLA2G16 encompass methods that result in a decreased amount of PLA2G16 polypeptide and methods that interfere with PLA2G16 molecular function. In some embodiments, PLA2G16 is inhibited by inhibiting or interfering with PLA2G16 expression, so that a decreased amount of PLA2G16 polypeptide is produced. As used herein, "expression" encompasses the cellular processes involved in producing a polypeptide and include transcription, mRNA processing and transport (in the case of eukaryotic cells), and mRNA translation. A variety of methods useful for inhibiting or interfering with expression can be applied in embodiments of the present invention. In general, such methods result in decreased synthesis of PLA2G16 polypeptide and as a result, a reduction in the total level of PLA2G16 molecular functional activity present.

In some embodiments, PLA2G16 expression is inhibited using RNA interference (RNAi). Exemplary sequences for RNAi agents (e.g., siRNAs) that inhibit PLA2G16 expression are provided in the Examples. Additional sequences can be selected using various approaches known in the art including. If desired, such sequences can be selected to minimize "off-target" effects. In some embodiments, position-specific chemical modification is used to reduce potential off-target effects. In some embodiments, at least two different siRNAs targeted to the PLA2G16 gene are used (e.g., in combination). RNAi is use of herein for a variety of purposes. For example, an RNAi agent can be used as a PLA2G16 inhibitor, e.g., for therapeutic or research purposes. An RNAi agent that inhibits PLA2G16 can be useful to confirm that the effect of a second compound, e.g., a small molecule, is due to an effect on PLA2G16 (rather than on another protein). For example, a small molecule that is a putative specific inhibitor of PLA2G16 may be expected not to have an effect in a cell in which PLA2G16 expression is inhibited by RNAi. In other aspects, RNAi is used to inhibit expression of a PLA2 other than PLA2G16, which may be expressed by a cell. Inhibiting other PLA2 enzymes may facilitate identification of compounds that inhibit PLA2G16.

In some embodiments of the invention, PLA2G16 expression is inhibited using an antisense approach in which one or more oligonucleotides complementary to mRNA encoding PLA2G16 is delivered to cells and hybridizes to the PLA2G16 mRNA resulting in, e.g., degradation of the mRNA by RNase H or blockage of translation by steric hindrance.

In some embodiments of the invention, a PLA2G16 inhibitor inhibits at least one molecular function of PLA2G16. In some embodiments, the molecular function is a catalytic activity, e.g., phospholipase activity and/or lysophospholipase activity. For example, the activity may be phospholipase A2 activity, i.e., ability to catalyze hydrolysis of the sn-2 bond of phospholipids. In some embodiments, a compound directly inhibits a molecular function of PLA2G16. "Direct inhibition" refers to a physical interaction (binding) with a target that inhibits a molecular function of the target. For example, binding of a PLA2G16 inhibitor to PLA2G16 can interfere with the enzyme's ability to catalyze a reaction and/or prevent a substrate from entering the active site. A variety of compounds can be used to directly inhibit PLA2G16 molecular function. Exemplary compounds that directly inhibit PLA2G16 can be, e.g., small molecules, antibodies, or aptamers. In some embodiments, a direct inhibitor is a substrate analog (e.g., a phospholipid analog) or a transition state analog.

In some embodiments, an inhibitor is an irreversible inhibitor. Most irreversible enzyme inhibitors react with the enzyme and change it chemically, such as by modifying amino acid residue(s) that are needed for enzymatic activity. For example, an irreversible inhibitor can comprise one or more reactive functional groups such as an aldehyde, haloalkane, alkene, fluorophosphonate (e.g., alkyl fluorophosphonate), Michael acceptor, phenyl sulfonate, methylketone, e.g., a halogenated methylketone or diazomethylketone, fluorophosphonate, vinyl ester, vinyl sulfone, or vinyl sulfonamide. In some embodiments, an irreversible PLA2G16 inhibitor comprises an electrophilic group that reacts with an amino acid side chain of PLA2G16. For example, the electrophilic group may react with an amino acid side chain containing a nucleophile such as a hydroxyl or sulfhydryl group. For example, the amino acid may be cysteine, serine, or threonine. In another embodiment, an irreversible inhibitor reacts with a histidine. Moieties sometimes referred to in the art as "cysteine traps" may be used in various embodiments. In some embodiments a cysteine-reactive moiety is a maleimide, isothiazolinone, tetrazole, lactam, or carbamate. A reactive functional group can be incorporated into a substrate analog or other molecule compatible with binding to the enzyme, e.g., in or near the active site.

In other embodiments, a PLA2G16 inhibitor is a reversible inhibitor. Reversible inhibitors bind non-covalently and may bind to the enzyme, the enzyme-substrate complex, or both. Inhibition by a reversible inhibitor may be classified as competitive inhibition, uncompetitive inhibition, mixed inhibition, non-competitive inhibition. See, e.g., Berg J. M, et al., Biochemistry, 6$^{th}$ ed., W. H. Freeman and Company, 2007. In some embodiments, a reversible inhibitor binds to the PLA2G16 active site and/or competes with substrate(s) for access to the PLA2G16 active site. In some embodiments a reversible inhibitor is a non-hydrolyzable substrate analog.

In some embodiments, the PLA2G16 inhibitor is an analog of a fatty acid, wherein the analog comprises an alkyl chain between 4 and about 30 carbons long, e.g., between 12 and 20 carbons long. In some embodiments, the alkyl group is saturated. In some embodiments, the alkyl group is unsaturated. In some embodiments, the alkyl group is unbranched. In some embodiments, the alkyl group has the structure of an alkyl group naturally found in a fatty acid present in vertebrate cells. Exemplary fatty acids include, e.g., myristoleic acid, palmitoleic acid, sapienic acid, oleic acid, linoleic acid, linolenic acid, arachidonic acid, eicosapentaenoic acid, erucic acid, docosahexaenoic acid, lauric acid, myristic acid, palmitic acid, stearic acid, and eicosanoic acid. In some embodiments, the PLA2G16 inhibitor is an analog of arachidonic acid or linoleic acid. In some embodiments, the analog is a methylated fatty acid. In some embodiments, the arachidonic acid analog is an eicosadienoic acid, such as 7,7-dimethyl-5,8-eicosadienoic acid.

In some embodiments, the inhibitor comprises an analog of a fatty acid, wherein the analog comprises a reactive functional group. In some embodiments, the fatty acid analog comprises a halogenated methyl ketone group instead of a carboxyl group. For example, the halogen can be chlorine, fluorine, bromine, or iodine in various embodiments. In some embodiments, the halogenated methyl ketone group is fluoromethyl ketone, trifluoromethyl ketone, or chloromethyl ketone. In some embodiments, the fatty acid is arachidonic acid. In one embodiment, the inhibitor is a trifluoromethyl ketone analog of arachidonic acid in which the COOH group is replaced with COCF3, i.e., the compound arachidonyl trifluoromethyl ketone (AACOCF3). AACOCF3 inhibits PLA2G16 and also inhibits cPLA$_2$ and sPLA$_2$ (Duncan, supra). It is believed that AACOCF3 binds in a hydrophobic pocket of cPLA$_2$, and that the carbonyl group of AACOCF3 forms a covalent bond with serine 228 in the active site (Street et al., 1993; Trimble et al., 1993). Without wishing to be bound by theory, AACOCF3 may react with the active site serine of PLA2G16. In another embodiment, the PLA2G16 inhibitor is methyl arachidonyl fluorophosphate (MAFP) or an analog thereof (see, e.g., Martin, B R, et al., J. Pharm. Exp. Ther., 294 (3), 294:1209-1218, 2000). MAFP is believed to inhibit serine and cysteine hydrolases by covalently binding to the enzyme. It inhibits PLA2G16 as well as iPLA2 and cPLA2, but not sPLA2 (Duncan, supra). Without wishing to be bound by theory, PLA2G16 may require an active cysteine residue (i.e. Cys-113) that is inactivated by MAFP.

A variety of other compounds that inhibit one or more Group I-XV PLA2s have been identified. For example, U.S. Pat. Pub. No. 20080319065 discloses compounds that contain a 2-oxoamide with a hydrocarbon tail and a four carbon tether and are reported to inhibit PLA2 Group IVA c PLA2 and/or Group VIA iPLA2 and/or Group V sPLA2. U.S. Pat. Pub. Nos. 20030144282 and 20100029645 disclose inhibitors of various PLA2 enzymes. Other compounds that inhibit one or more PLA2 enzymes include piperazines (see, e.g., WO2003048139); pyrimidone, pyridone, pyridinone, and pyrimidinone compounds (see, e.g., WO2002030904; WO 2001060805; WO 2000027824; WO 2003087088; WO 2003086400; WO 2003/042218; WO2003042206; WO2002030911; WO2003041712), pyrrolidine derivatives (see, e.g., WO1998033797). Without wishing to be bound by any theory, at least some of the compounds that inhibit one or more Group I-XV PLA2 enzymes may also inhibit PLA2G16. In some embodiments, the main mechanism of action against such other Group I-XV PLA$_2$ does not involve specifically binding to a sequence motif that is present in such other PLA2 but is absent in PLA2G16. For example, in some embodiments the compound is not whose main mechanism of action involves binding to a GXSXG consensus motif or a CCXXHDXC motif (SEQ ID NO: 4).

In some embodiments, a PLA2G16 inhibitor comprises a peptide, e.g., a peptide identified using a display technique, such as phage display or ribosome display. In some embodiments, a peptide comprises one or more non-standard amino acids. In some embodiments, a peptide is cyclic. For example, the peptide can be cyclized via a disulfide bond or covalent linkage, e.g., between the N- and C-terminal amino acids, between the N- or C-terminal amino acid an internal amino acid, or between two internal amino acids.

In some embodiments, a PLA2G16 inhibitor comprises an aptamer. In general, an aptamer is an often single-stranded oligonucleotide (e.g., DNA or RNA, optionally containing one or more non-standard nucleotides or modifications such as 2'-fluoro, 2'-amino, and/or 2'-methoxy nucleotides) that binds to a particular molecule of interest. Aptamers are typically derived from an in vitro evolution and selection process such as SELEX. Methods for obtaining aptamers specific for a protein of interest are known in the art. See, e.g., Brody E N, Gold L. *J Biotechnol.*, 74(1):5-13, 2000.

In some embodiments, a PLA2G16 inhibitor comprises an antibody or portion thereof. In some embodiments, the antibody is a single-chain antibody, diabody, triabody, or minibody. Standard methods of antibody production known in the art can be used to produce an antibody, e.g., a monoclonal antibody, that binds to PLA2G16. In some embodiments, an animal, e.g., a mouse or rabbit is immunized with PLA2G16 or a portion thereof, antibody producing cells are isolated, and a monoclonal antibody is identified using hybridoma technology. In some embodiments, the mouse is a transgenic mouse comprising at least some unrearranged human immunoglobulin gene sequences and that preferably have a targeted disruption of endogenous heavy and light chain murine sequences. In some embodiments, an antibody is identified or produced using recombinant nucleic acid technology (e.g., phage or yeast display). See, e.g., Lonberg N. Fully human antibodies from transgenic mouse and phage display platforms. Curr Opin Immunol. 20(4):450-9, 2008.

In some embodiments of the invention, a compound indirectly inhibits PLA2G16. "Indirect inhibition" refers to inhibition of a target (e.g., PLA2G16) by a mechanism that does not require physical interaction between the compound and the target. For example, the compound could inhibit expression or activity of a polypeptide that is involved in localization or post-translational modification of PLA2G16, wherein such localization or post-translational modification is important for PLA2G16 molecular function.

In some embodiments, a PLA2G16 inhibitor is not a compound that is known or suggested in the art to have antiviral activity and/or to be useful in treating a subject in need of treatment for a viral infection. In some embodiments, a PLA2G16 inhibitor is a compound that is known or suggested in the art to have antiviral activity and/or to be useful in treating a subject in need of treatment for a viral infection but, optionally, may be administered or otherwise used in the present invention (i) to inhibit infection by a different virus, e.g., a virus against which the compound is not known or suggested to have antiviral activity; (ii) in a different (e.g., more highly purified) form, in a different amount or composition, or in combination with one or more different substances; (iii) by a different route or to a subject of a different species; and/or (iv) explicitly excluded from any one or more of the inventive compositions and/or methods.

VI. Compositions and Methods for Identifying and/or Testing Compounds

The invention provides methods of identifying compounds useful for inhibiting viral infection and assay systems for performing the inventive methods. In some aspects, the invention provides a method of determining whether a test compound is a candidate antiviral compound, the method comprising the step determining whether the test compound inhibits PLA2G16 polypeptide, wherein if the compound inhibits PLA2G16, the compound is a candidate antiviral compound. In a related aspect, the invention provides a method of identifying a candidate antiviral compound comprising steps of: (a) providing a test compound; (b) determining whether the test compound inhibits PLA2G16, wherein if the compound inhibits PLA2G16, the compound is a candidate antiviral compound.

In some embodiments, the method comprises determining whether the test compound inhibits expression of PLA2G16, wherein if the compound inhibits PLA2G16 expression the compound is a candidate antiviral compound. In some embodiments, the method comprises determining whether the compound inhibits a molecular function of PLA2G16, wherein if the compound inhibits a molecular function of PLA2G16 the compound is a candidate antiviral compound. In some embodiments, the molecular function is an enzymatic activity, e.g., phospholipase A2 activity or lysophospholipase activity.

In some embodiments, a method is performed using a PLA2G16 polypeptide identical in sequence to PLA2G16 that is naturally expressed by a multicellular organism, i.e., a native PLA2G16. In some embodiments, a method is performed using a functional PLA2G16 variant. In some embodiments, the functional variant used in an inventive assay retains at least 20%, 30%, 40%, 50%, 60%, 70%, 80%, 90%, 95%, 96%, 97%, 98%, 99%, or more of the phospholipase A2 activity of PLA2G16. In some embodiments, a functional variant retains at least 20%, 30%, 40%, 50%, 60%, 70%, 80%, 90%, 95%, 96%, 97%, 98%, 99%, or more of the lysophospholipase activity of PLA2G16. In some embodiments, the functional variant retains at least 50% or at least 75% or has about the same phospholipase A2 activity and/or lysophospholipase activity as native PLA2G16. A PLA2G16 variant may have properties that make it convenient to use in an inventive screening method, such as the presence of a tag that facilitates production or purification of the protein. A compound identified as an inhibitor using a PLA2G16 variant can be further tested using native PLA2G16 to confirm its ability to inhibit the native polypeptide.

A wide variety of test compounds can be used in the inventive methods. For example, a test compound can be a small molecule, polypeptide, peptide, nucleic acid, oligonucleotide, lipid, carbohydrate, or hybrid molecule. Compounds can be obtained from natural sources or produced synthetically. Compounds can be at least partially pure or may be present in extracts or other types of mixtures. Extracts or fractions thereof can be produced from, e.g., plants, animals, microorganisms, marine organisms, fermentation broths (e.g., soil, bacterial or fungal fermentation broths), etc. In some embodiments, a compound collection ("library") is tested. The library may comprise, e.g., between 100 and 500,000 compounds, or more. Compounds are often arrayed in multiwell plates. They can be dissolved in a solvent (e.g., DMSO) or provided in dry form, e.g., as a powder or solid. Collections of synthetic, semi-synthetic, and/or naturally occurring compounds can be tested. Compound libraries can comprise structurally related, structurally diverse, or structurally unrelated compounds. Compounds may be artificial (having a structure invented by man and not found in nature) or naturally occurring. In some embodiments, a library comprises at least some compounds that have been identified as "hits" or "leads" in other drug discovery programs and/or derivatives thereof. A compound library can comprise natural products and/or compounds generated using non-directed or directed synthetic organic chemistry. Often a compound library is a small molecule library. Other libraries of interest include peptide or peptoid libraries, cDNA libraries, and oligonucleotide libraries.

A library can be focused (e.g., composed primarily of compounds having the same core structure, derived from the same precursor, or having at least one biochemical activity in common). In some embodiments, compounds that have been identified as inhibitors of one or more Group I-XV PLA2 enzymes are tested. In some embodiments, the IC50 of a compound identified as a PLA2G16 inhibitor may be about 2, 5, 10, 20, 50, 100, 250, 500, or 1000-fold lower for PLA2G16 versus one or more other PLA2 enzymes (e.g., one, more than one, or all other PLA2 enzymes present in humans and known to date).

Compound libraries are available from a number of commercial vendors such as Tocris BioScience, Nanosyn, BioFocus, and from government entities. For example, the Molecular Libraries Small Molecule Repository (MLSMR), a component of the U.S. National Institutes of Health (NIH) Molecular Libraries Program is designed to identify, acquire, maintain, and distribute a collection of >300,000 chemically diverse compounds with known and unknown biological activities for use, e.g., in high-throughput screening (HTS) assays. The NIH Clinical Collection (NCC) is a plated array of approximately 450 small molecules that have a history of use in human clinical trials. These compounds are highly drug-like with known safety profiles. The NCC collection is arrayed in six 96-well plates. 50 µl of each compound is supplied, as an approximately 10 mM solution in 100% DMSO. In some embodiments, a collection of compounds comprising "approved human drugs" is tested. An "approved human drug" is a compound that has been approved for use in treating humans by a government regulatory agency such as the US Food and Drug Administration, European Medicines Evaluation Agency, or a similar agency responsible for evaluating at least the safety of therapeutic agents prior to allowing them to be marketed. The test compound may be, e.g., an antineoplastic, antibacterial, antiviral, antifungal, antiprotozoal, antiparasitic, antidepressant, antipsychotic, anesthetic, antianginal, antihypertensive, antiarrhythmic, antiinflammatory, analgesic, antithrombotic, antiemetic, immunomodulator, antidiabetic, lipid- or cholesterol-lowering (e.g., statin), anticonvulsant, anticoagulant, antianxiety, hypnotic (sleep-inducing), hormonal, or anti-hormonal drug, etc. In some embodiments, a compound is one that has undergone at least some preclinical or clinical development or has been determined or predicted to have "drug-like" properties. For example, the test compound may have completed a Phase I trial or at least a preclinical study in non-human animals and shown evidence of safety and tolerability. In some embodiments, a test compound is substantially non-toxic to cells of an organism to which the compound may be administered or cells in which the compound may be tested, at the concentration to be used or, in some embodiments, at concentrations up to 10-fold, 100-fold, or 1,000-fold higher than the concentration to be used. For example, there may be no statistically significant effect on cell viability and/or proliferation, or the reduction in viability or proliferation can be no more than 1%, 5%, or 10% in various embodiments. Cytotoxicity and/or effect on cell proliferation can be assessed using any of a variety of assays (some of which are mentioned above). In some embodiments, a test compound is not a compound that is found in a cell culture medium known or used in the art, e.g., culture medium suitable for culturing vertebrate, e.g., mammalian cells or, if the test compound is a compound that is found in a cell culture medium known or used in the art, the test compound is used at a different, e.g., higher, concentration when used in a method of the present invention.

In some embodiments, a test compound is a compound that is recognized in the art as having antiviral activity against one or more viruses, but that is not known to be useful to inhibit infection by a virus of interest, e.g., a picornavirus. In some embodiments, a test compound is not a compound that is recognized in the art as having antiviral activity.

In some embodiments, one or more compounds or mixtures thereof having known antiviral activity is tested, wherein the molecular target of the compound or mixture and/or mechanism of antiviral activity is unknown. Testing of such compounds or mixtures according to the present invention to determine whether they inhibit PLA2G16 may lead to discovering that PLA2G16 is the molecular target. Such discovery may facilitate purification of an active component from a mixture, development of more highly active derivatives of the compound, and/or otherwise permit further development of the compound or mixture as a therapeutic agent.

The step of determining whether a test compound inhibits PLA2G16 expression can be carried out in a variety ways. Compounds that inhibit PLA2G16 expression can be identified by contacting cells with a test compound, maintaining the cells in culture for a suitable period of time (e.g., sufficient time to allow degradation of existing PLA2G16 mRNA and/or protein), and then measuring the level of PLA2G16 mRNA or protein. Methods known in the art can be used for measuring mRNA or protein. A variety of different hybridization-based or amplification-based methods are available to measure RNA. Examples include Northern blots, microarray (e.g., oligonucleotide or cDNA microarray), reverse transcription (RT)-PCR (e.g., quantitative RT-PCR), or reverse transcription followed by sequencing. The TaqMan® assay and the SYBR® Green PCR assay are commonly used real-time PCR techniques. Other assays include the Standardized (Sta) RT-PCR™ (Gene Express, Inc., Toledo, Ohio) and QuantiGene® (Panomics, Inc., Fremont, Calif.). In some embodiments the level of PLA2G16 mRNA is measured. In other embodiments, a reporter-based system is used. In some embodiments, a reporter-based system comprises a nucleic acid in which expression control elements of the PLA2G16 gene are operably linked to a sequence that encodes a reporter molecule ("reporter"). Reporters are often proteins but could be nucleic acids. Reporters are often readily detectable molecules, such as proteins that produce a fluorescent, luminescent, or colorimetric signal or are capable of absorbing light of a particular wavelength. In some embodiments, a reporter molecule comprises an enzyme that acts on a substrate to produce a fluorescent, luminescent, or colorimetric signal. Exemplary reporter molecules include, e.g., green, blue, sapphire, yellow, red, orange, and cyan fluorescent proteins and derivatives thereof; monomeric red fluorescent protein and derivatives such as those known as "mFruits", e.g., mCherry, mStrawberry, mTomato; luciferase; beta-galactosidase; horseradish peroxidase; alkaline phosphatase; etc. In some embodiments, a reporter is a secreted protein. In some embodiments, a reporter is encoded by a sequence that is codon-optimized for expression in a cell from an organism of interest. Methods for assessing the efficacy of an RNAi agent to silence expression of a target gene can involve use of a sequence in which the mRNA target of an shRNA or siRNA (or a portion of the target) is cloned downstream of a sequence that encodes a reporter, so that a bicistronic mRNA transcript encoding both the target sequence and the reporter is produced. Target gene knockdown results in the degradation (or translational inhibition) of the mRNA transcript, which causes a proportional decrease in the expression of the reporter protein.

Compounds that inhibit PLAG16 molecular function can be identified using a variety of different cell-free or cell-based assays. A cell-free assay typically involves an isolated target molecule. For example, the target molecule could be present in a cell or tissue lysate or fraction thereof (e.g., a lysate made from cells that express the target molecule) or could be an at least partially purified or synthesized target molecule. A tissue lysate could be made from any tissue containing cells that express PLA2G16. In some embodiments, a tissue lysate is obtained from adipose tissue, e.g., white adipose tissue. Various cells from which a cell lysate could be prepared or from which a PLA2G16 polypeptide could be purified are mentioned below in the discussion of cell-based assays. In some embodiments, an isolated polypeptide is a polypeptide that has been synthesized using recombinant nucleic acid techniques or in vitro translation. In order to perform the assay, a test compound is contacted with the target molecule, e.g., by preparing a composition comprising the test compound and the target molecule. One or more parameters are measured, e.g., binding, enzymatic activity, etc. The composition can comprise other component(s) necessary or helpful for identifying a compound of interest. In some embodiments, a composition for use in a binding assay or activity assay comprises cell membranes or cell membrane components. Such membranes or components may be naturally occurring (e.g., components present in animal cell membranes), artificial, or combination thereof in various embodiments. For example, the composition can contain a lipid membrane bilayer, lipid vesicles, etc. Optionally, a lipid bilayer is immobilized on a surface. In some embodiments the lipids comprise phospholipids.

A variety of cell-free assays may be performed to identify compounds that inhibit a PLA2G16 polypeptide. In some embodiments, an assay detects whether a test compound binds to a PLA2G16 polypeptide and/or quantifies one or more characteristics of such binding. Numerous binding assay formats are known in the art. In some embodiments, a label-free assay is used, while in other embodiments either the PLA2G16 polypeptide or test compound is detectably labeled. In some embodiments, a PLA2G16 polypeptide or a compound to be tested for ability to bind to and/or inhibit activity of a PLA2G16 polypeptide is attached to a solid support. In some embodiments, a solid support is an article having a rigid or semi-rigid surface. In some embodiments, at least one surface of the support is substantially flat. In other embodiments, a support is approximately spherical. A support can be composed of an inorganic or organic material or combination thereof. In some embodiments, a support is composed at least in part of a metal, ceramic, glass, plastic, gel, or other matrix. Such articles may, for example, take the form of plates (e.g., multiwell plates), slides, particles (e.g., "beads", e.g., magnetic beads), pellets, bars, rods, pins, disks, chips, filters, or other suitable forms. In some embodiments, a support comprises a sensor, e.g., a sensor capable of detecting changes in binding. For example, the sensor could detect a change in weight or a signal such as fluorescence. In some embodiments, the support comprises an electrode. In some embodiments, compounds are arranged as a small molecule microarray. Compounds could be present in multiple locations on a surface, in individual wells or vessels, etc. See, e.g., Vegas A J, et al., Chem Soc Rev. 37(7):1385-94, 2008. In some embodiments, a PLA2G16 polypeptide or compound is noncovalently attachment or covalently linked to the support. Noncovalent attachment could be, e.g., by adsorption of the polypeptide or compound to the surface (which may be coated with a substance to facilitate such adsorption), via an affinity-based mechanism, or other means of immobilizing the PLA2G16 polypeptide or test compound so that it remains physically associated with the support. In some embodiments, an antibody is used to attach a PLA2G16 polypeptide or test compound to a support. In some embodiments, a PLA2G16 polypeptide or test compound is attached to a support via a biotin-avidin interaction or other strong binding interaction, wherein one of two binding partners is attached directly or indirectly to the support and the other binding partner is attached to the molecule to be immobilized.

In some embodiments, test compounds are immobilized in multiple locations (e.g., in an array format. PLA2G16 polypeptide is added and the composition is maintained for a suitable time period to allow binding to occur. In some embodiments, unbound material is removed by washing, and PLA2G16 polypeptide is detected using an antibody or, if the polypeptide is detectably labeled, by detecting a signal. In other embodiments, a washing step is not necessary. For example, binding may be detected by measuring a change in fluorescence polarization, fluorescence resonance energy transfer, or electrochemiluminescence. In other embodiments, PLA2G16 polypeptide is immobilized, test compounds are added, and binding is measured using similar approaches.

In some embodiments, surface plasmon resonance (SPR) is used to measure kinetics (on and/or off rates) and/or binding strength (affinity) between a test compound and a PLA2G16 polypeptide. For example, using SPR technology (e.g., systems such as those available from Biacore, Life Sciences, GE Healthcare) the binding and dissociation of a test compound to a protein immobilized on a chip can be measured, and the measured values compared with those obtained when a solution not containing the test compound is loaded on the chip. A test compound capable of binding to the protein can be selected on the basis of the binding and dissociation rate and/or binding level. Other useful methods for detecting and/or quantifying binding include use of a quartz crystal microbalance, optical cantilever, microchannel resonator, dual polarisation interferometer, coupled waveguide plasmon resonance, immunoprecipitation or other antibody-based detection methods, isothermal titration and differential scanning calorimetry, capillary electrophoresis, resonance energy transfer, electrochemiluninesce, and fluorescent correlation analysis.

In some embodiments, an aptamer, peptide, non-hydrolyzable substrate analog, or small molecule that is known to bind to a PLA2G16 polypeptide is labeled and used as a tool for screening test compounds (e.g., small molecules) for ability to bind to and/or inhibit activity of the polypeptide. The label can comprise, e.g., a radioactive, fluorescent, luminescent, or other readily detectable moiety. The ability of a test compound to compete with the labeled aptamer, peptide, non-hydrolyzable substrate analog, or small molecule can be detected and serves as an indicator of the binding of the test compound to the PLA2G16 polypeptide. For example, a scintillation proximity assay (SPA) can be used. In some embodiments of an SPA for identifying compounds that bind to a PLA2G16 polypeptide, the PLA2G16 polypeptide is attached to beads containing a scintillant material. The beads are typically located in wells or other vessels. In another embodiment, a PLA2G16 polypeptide is attached to scintillant material is embedded directly into wells. A radiolabelled compound capable of binding to the PLA2G16 polypeptide and a test compound are added to the well. Binding of the radiolabelled compound to the PLA2G16 polypeptide results in a signal. The signal is reduced in the presence of a test compound that competes with the radiolabelled compound for binding. See, e.g., J. Fraser Glickman, et al., Scintillation Proximity Assays in High-Throughput Screening. Assay and Drug Development Technologies. 6(3): 433-455, 2008, for review of SPA. Similar assays can be performed using filters.

In some embodiments, a compound is selected that binds to PLA2G16 polypeptide with a Kd equal to or less than approximately 1 mM, 500 µM, 100 µM, 50 µM, 10 µM, 5 µM, or 1 µM. In some embodiments, a compound binds to a PLA2G16 polypeptide with a Kd equal to or less than approximately 500 nM, 100 nM, 50 nM, or 10 nM. In some embodiments, a compound binds to a PLA2G16 polypeptide with a Kd between 0.1-10 nM. Compounds that bind to a PLA2G16 polypeptide may be further tested, e.g., in cell-free or cell-based assays, to determine the extent to which they inhibit PLA2G16 activity (e.g., catalytic activity), e.g., as described below.

A variety of different assays can be employed to identify and/or characterize compounds that inhibit PLA2G16 activity. In some embodiments, the ability of a compound to inhibit catalysis of a chemical reaction by PLA2G16 polypeptide is assessed. In some embodiments, the chemical reaction is hydrolysis of the sn-2 bond of a phospholipid. A composition comprising a PLA2G16 polypeptide, one or more PLA2G16 substrate(s), and a test compound is provided. The PLA2G16 polypeptide, one or more PLA2G16 substrate(s), and test compound are usually in a suitable liquid medium. In some embodiments, the liquid medium is an aqueous medium that comprises at least 50%, 60%, 70%, 80%, 90%, 95%, 96%, 97%, 98%, 99% or more water (v/v). In some embodiments, the liquid medium may comprise an organic solvent such as DMSO, e.g., in an amount that does not significantly affect the activity of the PLA2G16 polypeptide as compared with the activity in the absence of the organic solvent. A "substrate" in this context is a molecule on which PLA2G16 acts, i.e., a molecule that undergoes a chemical reaction that is catalyzed by PLA2G16. Exemplary substrates are discussed below. The concentration of the substrate and PLA2G16 polypeptide can vary. In some embodiments, the substrate is present at between about 1 µM and 500 µM, e.g., between about 10 µM and about 50 µM, 100 µM, or 200 µM. In some embodiments, the PLA2G16 polypeptide is present at between 1 µg/ml and about 100 µg/ml. It will be understood that the selection of concentrations and amounts can depend at least in part on the particular assay and is within the skill in the art. The composition is maintained for a suitable time period under conditions that would otherwise (i.e., in the absence of a compound that is a potential PLA2G16 inhibitor) be appropriate for the PLA2G16 polypeptide to catalyze a reaction in which the substrate(s) is/are converted to one or more product(s). The reaction may be stopped after a desired time period, e.g., by addition of (2:1) methanol:chloroform. The conditions and other component(s) present in the composition can vary depending, e.g., on the particular assay. Suitable conditions for a PLA2G16 polypeptide to act on a substrate can include, e.g., a pH of between about 6.5 and about 9.5, e.g., between about 7.0 and about 9.0, e.g., between about 7.5 and about 8.5, e.g., about 8.0. In some embodiments, the temperature is between 10° C. and 40° C., e.g., between 20° C. and 30° C., e.g., about 25° C. Other components may be present in the composition. In some embodiments, the composition comprises a buffer substance such as Tris-HCl or sodium borate, to help regulate the pH. Other buffer substances include, e.g., HEPES, MOPS, etc. In some embodiments, the composition comprises a divalent cation, e.g., calcium ($Ca^{2+}$). For example, in some embodiments, the composition comprises up to about 5 mM calcium, e.g., between about 0.5 mM and about 2.5 mM calcium. In exemplary embodiments, the composition comprises about 1 mM calcium or about 2 mM calcium. In some embodiments, the composition does not comprise a calcium chelator such as EDTA. In some embodiments, the composition comprises a calcium chelator in an amount that does not reduce the free calcium concentration below about 1.0 mM. In some embodiments, the composition comprises a detergent, e.g., deoxycholate, e.g., at between 1-5 mM, e.g., about 2 mM or about 3 mM.

In some embodiments, the amount of product produced and/or the rate of product formation is determined. The effect of the test compound on the amount of product produced and/or the rate at which the product is produced is assessed, e.g., by comparison with a suitable reference value. If the amount of product or rate of product production is decreased in the presence of the test compound as compared with a suitable reference value, the test compound inhibits the ability of the PLA2G16 polypeptide to catalyze a reaction in which the substrate is converted to one or more product(s), i.e., the test compound is an inhibitor of the PLA2G16 polypeptide. In some embodiments, the rate of substrate consumption or the amount of substrate consumed is determined. Equivalently, the amount of substrate remaining can be determined. If the amount of substrate consumed or the rate of substrate consumption is decreased in the presence of the test compound as compared with a suitable reference value, the test compound inhibits the ability of the PLA2G16 polypeptide to catalyze a reaction in which the substrate is converted to one or more product(s), i.e., the test compound is an inhibitor of the PLA2G16 polypeptide. A reference value in any of these assays can be a value measured under similar or identical conditions in the absence of the test compound.

In some embodiments, a PLA2G16 substrate is useful to measure phospholipase activity, e.g., phospholipase A2 activity. For example, a PLA2G16 substrate can be a naturally occurring or artificial phospholipid. As known in the art, most phospholipids are composed of 1,2-diacylglycerol and a phosphate group, and an organic molecule (often a nitrogenous base). A phosophodiester bridge links the glycerol backbone to the base, which is sometimes termed a "head group". Exemplary head groups are choline, ethanolamine, inositol, and serine. For example, a substrate can be a phosphatidylcholine or phosphatidylethanolamine. The hydrocarbon chains of the acyl groups of a phospholipid molecule are often different, e.g., they are derived from fatty acid molecules with different hydrocarbon chains. In some embodiments, the hydrocarbon chains are between 12 and 30 carbons in length. In some embodiments, a PLA2G16 substrate has the structure of a naturally occurring phospholipid, e.g., a phospholipid found in vertebrate cells, e.g., mammalian cells. Exemplary PLA2G16 substrates include, e.g., 1-palmitoyl-2-linoleoyl-PC, dilinoleoyl-PC, 1-palmitoyl-2-linoleoyl-PS, 1-palmitoyl-2-linoleoyl-PC, phosphatidylinositol, 1-palmitoyl-2-arachidonyl-PC (abbreviations: PC: phosphatidylcholine PE: phosphatidylethanolamine; PS: phosphatidylserine). In some embodiments, the substrate comprises choline as a head group. In some embodiments, a phospholipid analog containing a thio ester bond instead of the sn-2 ester is used. In some embodiments, a PLA2G16 substrate is useful for measuring lysophospholipase activity. For example, the substrate can be a lysophosphatidylcholine, e.g., 1-palmitoyl-2-hydroxy-sn-glycerol-3-phosphocholine.

In some embodiments, a substrate comprises a moiety that facilitates detection of a product of a biochemical reaction catalyzed by a PLA2G16 polypeptide. For example, the substrate can comprise one or more radioactive atoms, fluorescent labels, and/or fluorescence quenchers. In some embodiments, the label comprises 14C, 3H, or 32P. In some embodiments, the substrate comprises a moiety that emits a signal upon cleavage of the substrate. In some embodiments, the substrate comprises a moiety that can be readily detected upon release from the substrate. For example, the moiety may react with another compound to produce a colorimetric, fluorescent, or luminescent signal. Labels include, e.g., organic materials (including "traditional" dye fluorophores, quenchers, and polymers); inorganic materials such as metal chelates, metal and semiconductor nanocrystals (e.g., "quantum dots", and fluorophores of biological origin such as certain amino acids (e.g., tryptophan, tyrosine); and compounds that exhibit luminescence upon enzymatic catalysis such as naturally occurring or synthetic luciferins (e.g., firefly or *Renilla* luciferin, coelenterazine). Fluorescent dyes include, e.g., acridine dyes; Alexa dyes; BODIPY, cyanine dyes; fluorescein dyes, rhodamine dyes, and derivatives of any of the foregoing. See, e.g., The Handbook—A Guide to Fluorescent Probes and Labeling Technologies, 10th edition (Invitrogen Corp.), which describes numerous fluorescent and otherwise detectable molecules and methods for their use and modification. In another embodiment, a phospholipid analogue containing a thio ester bond instead of the sn-2 ester is used, and hydrolysis of the thioester bond at the sn-2 position by PLA2 releases free thiol which can be detected by DTNB (5,5'-dithiobis(2-nitrobenzoic acid)).

In some embodiments, a substrate is present in a vesicle or micelle. For example, lipid-detergent micelles can be used. In some embodiments, an ionic detergent such as deoxycholate is used. Other detergents include, e.g., Triton X-100. In some embodiments, a composition containing about 100 μM 1-palmitoyl-2-linoleoyl-PC with 2 mM deoxycholate and 2 mM $CaCl_2$ is used. A test compound can be incorporated into the vesicle or micelle.

A variety of assays can be used to measure PLA2 catalytic activity. In some embodiments, an assays that has been used in the art to measure activity of a Group I-XV PLA2 (e.g., a cytosolic or secreted PLA2) is used or modified for use to measure catalytic activity of PLA2G16. In some embodiments, a radiometric assay is used, with a substrate of phospholipid (e.g., phosphatidylcholine or phosphatidylethanolamine) containing a 14C- or 3H-labeled fatty acid at the sn-2 position. The fatty acids released are separated from the unreacted substrate and quantified by liquid scintillation counting. In other embodiments, a fluorescence displacement assay, is used. A fluorescent molecule can be detected using, e.g., a spectrophotometer. An exemplary assay involves the displacement of a fluorescent fatty acid probe from albumin or rat liver fatty acid-binding protein by the decanoic acid released as a result of the phospholipase A2-catalyzed hydrolysis of didecanoyl-phosphatidylcholine A. R. Kinkaid & D. C. Wilton, A continuous fluorescence displacement assay for phospholipase a2 using albumin and medium chain phospholipid substrates. Anal. Biochem. 212: 65-70, 1993; D. C. Wilton, A continuous fluorescence displacement assay for the measurement of phospholipase A2 and other lipases that release long-chain fatty acids. Biochem. J. 266: 435-439, 1990). See also, Huang, Z., et al., Anal. Biochem. 222: 110-115, 1994, which describes an assay for cPLA2 activity based on hydrolysis of fatty acid esters of 7-hydroxycoumarin by cPLA2, producing the free fatty acid and highly fluorescent 7-hydroxycoumarin. Another assay is a fluorometric phospholipase assay based on polymerized liposome substrates (Chu, W., et al., Fluorometric phospholipase assays based on polymerised liposome substrates. Methods Mol. Biol. 109: 7-17, 1999). In another embodiment, a phospholipid analogue containing a thio ester bond instead of the sn-2 ester is used as a substrate to measure phospholipase activity (Yu, L, et al. Carbonothioate phospholipids as substrate for a spectrophotometric assay of phospholipase A2. Anal. Biochem. 265: 35-41, 1998).

In another embodiment, a coupled spectrophotometric assay using dilinoleoyl phosphatidylcholine (DL-PC) as PLA2 substrate and lipoxygenase as the coupling enzyme is used. See, e.g., Jiménez, M., et al. A continuous spectrophotometric assay for phospholipase A(2) activity Anal Biochem., 319(1):131-7, 2003, and references therein, and Duncan, supra. In this assay, lipoxygenase (linoleate:oxygen oxidoreductase, EC 1.13.11.12) catalyzes the addition of molecular oxygen to fatty acids containing at least one (Z,Z)-pentadiene system to give the corresponding hydroperoxides. Lipoxygenase oxidizes the linoleic acid released by the action of phospholipase, the activity of which can then be followed spectrophotometrically by recording the increase in absorbance at 234 nm due to the formation of the corresponding hydroperoxide from the linoleic acid by the action of lipoxygenase. This method provides a continuous record of phospholipid hydrolysis.

In some embodiments, a scintillation proximity assay (SPA) is used. For example, a radiolabelled PLA2G16 substrate can be attached to beads containing a scintillant material. The beads are typically located in wells or other vessels. In another embodiment, scintillant material is embedded directly into wells. A PLA2G16 polypeptide is added to the well in a suitable composition (optionally containing calcium and/or a buffer). Hydrolysis of the substrate releases the radioactive moiety, resulting in a decreased signal. See, e.g., J. Fraser Glickman, supra for discussion of SPA.

In some embodiments, an assay readout is based on resonance energy transfer (RET), e.g., fluorescence resonance energy transfer (FRET), luminescence resonance energy transfer (LRET), or bioluminescence resonance energy transfer (BRET). A wide variety of RET-based assays can be implemented. In general, such assays make use of a distance-dependent interaction involving energy transfer between two moieties (sometimes termed a donor and acceptor). If both moieties are present as part of a PLA2G16 substrate and positioned so that cleavage of the substrate releases one of the moieties, a signal (e.g., an increase or decrease in a signal) can be detected. FRET is a distance-dependent interaction between the electronic excited states of two moieties in which excitation is transferred from a donor moiety to an acceptor moiety without emission of a photon, resulting in emission from the FRET acceptor. LRET has similarities to FRET but uses a luminescent moiety, e.g. a lanthanide as the energy-transfer donor. BRET is analogous to FRET but uses a luminescent or luminescence-generating biomolecule such as luciferase, aequorin, or a derivative thereof as an energy donor and a fluorescent moiety, e.g., a biomolecule such as green fluorescent protein (GFP) as the acceptor, thus eliminating the need for an excitation light source (reviewed in Pfleger, K, an Eidne, K., Nature Methods, 3(3), 165-174, 2006).

Assays of the invention may detect acceptor emission, donor quenching (decreased emission from the RET donor), and/or an alteration in the fluorescence lifetime of the donor. Assays of the invention can make use of increases in acceptor emission, decreases in acceptor emission, donor quenching, reduction in donor quenching, and/or increase or decrease in fluorescence lifetime of the donor to detect cleavage of a PLA2G16 substrate. Nonfluorescent acceptors, also referred to as quenchers are of use and include dabcyl and QSY dyes. Such molecules are capable of absorbing the energy of an excited fluorescent label when located in close proximity and of dissipating that energy without the emission of visible light. Numerous suitable donor/acceptor pairs are known in the art. See, e.g., The Handbook—A Guide to Fluorescent Probes and Labeling Technologies, 10th edition (Invitrogen Corp.).

In some embodiments of a FRET-based assay, a first acyl chain of the PLA2G16 substrate has an attached fluorescence quencher and the second acyl chain has an attached fluorophore. Intramolecular FRET from the fluorophore to the quencher quenches fluorescence until PLA2-mediated substrate cleavage, when at least one fatty acid moiety becomes separated from the remainder of the molecule, and the intermolecular distance exceeds that required for efficient energy transfer. An increase in fluorescence signal indicates substrate cleavage. The presence of an inhibitor will cause a reduction in the fluorescence signal relative to that which would be observed in the absence of the inhibitor. In some embodiments the phospholipids sn-1-acyl chain contains an attached fluorescence quencher (e.g., Dabcyl, also known as p-methyl red), and the sn-2 acyl chain contains an appended BODIPY fluorophore, Intramolecular FRET (fluorescence resonance energy transfer) to the Dabcyl group quenches BODIPY fluorescence until PLA-mediated substrate cleavage. See, e.g., Rose, T M & Prestwich, G D, ACS Chemical Biology, 1(2): 83-89, 2006, for description of Dabcyl- and BODIPY-containing phospholipids DBPA, DBPC, DBPE, and DBPG (abbreviations: DB: Dabcyl-BODIPY; PG: phosphatidylglycerol).

Another assay format that can be used to measure PLA2 activity is a fluorescence based assay in which cationic conjugated polyelectrolytes are supported on silica microspheres. (See, e.g., Chemburu S, et al. Conjugated polyelectrolyte supported bead based assays for phospholipase A2 activity, Phys Chem B., 112(46):14492-9, 2008, which describes such an assay for human serum-derived PLA2. This assay can be modified for use to detect compounds that inhibit activity of a PLA2G16 polypeptide). The polymer-coated beads are overcoated with an anionic phospholipid to provide "lipobeads" that serve as a sensor for PLA2. The lipid serves a dual role as a substrate for PLA2 and an agent to attenuate quenching of the polymer fluorescence by the external electron transfer quencher 9,10-anthraquinone-2,6-disulfonic acid (AQS). Quenching of the polymer fluorescence by AQS increases as the PLA2 digests the lipid. The lipid can also be used itself as a quencher and substrate by employing a small amount of energy transfer quencher substituted lipid in the anionic phospholipid coating the beads. In this case the fluorescence of the polymer is quenched when the lipid layer is intact; as the enzyme digests the lipid, the fluorescence of the polymer is restored. The sensing of PLA2 activity can be performed by monitoring fluorescence changes in a multiwell plate reader and/or by flow cytometry.

A "cell-based assay" is an assay in which viable cells that express or contain a PLA2G16 polypeptide are contacted with a test compound and a parameter of interest such as PLA2G16 activity is assessed. Typically, the cells are maintained in cell culture and the test compound is added to the culture medium. In some embodiments, the effect of the test compound on the ability of the PLA2G16 polypeptide to act on a PLA2G16 substrate is assessed. For example, a PLA2G16 substrate, e.g., a detectably labeled substrate, can be added to the culture medium or synthesized by the cell from a labeled precursor. Cleavage of the substrate may be detected by detecting a free fatty acid or by detecting a downstream product produced from a free fatty acid. For example, arachidonic acid is modified by cyclooxygenases to form eicosanoids (e.g., prostaglandins, leukotrienes). In some embodiments, a cell that substantially lacks other PLA2 enzymes that could act on the PLA2G16 substrate can be used. In some embodiments, such cells are identified by screening a variety of cell lines for expression of known PLA2 enzymes. In other embodiments, a cell line is generated by targeted deletion or insertion into the genes encoding one or more PLA2 enzyme(s) or by causing the cell to express shRNA that inhibit expression of such other PLA2 enzyme(s). In other embodiments, the assay is performed in cells that have been contacted with siRNA specific for such other PLA2 enzyme(s) to knock down their expression.

A compound identified as an inhibitor of a PLA2G16 polypeptide can be tested in cell culture or in animal models ("in vivo") to determine its ability to inhibit viral infection. In some embodiments, host cells are contacted with a virus and a PLA2G16 inhibitor under conditions suitable for infection of the cells. The ability of the test compound to inhibit viral infection is assessed. If the compound detectably reduces viral infection, the compound is identified as an antiviral compound. The virus can be, e.g., any virus that utilizes PLA2G16 polypeptide, or a PLA2G16-like polypeptide, in its life cycle.

A wide variety of cell types can be used in embodiments of the inventive methods. Typically, the cell expresses or contains a PLA2G16 polypeptide, either naturally or as a result of modification by the hand of man, although cells that do not express a PLA2G16 may be useful, e.g., for control purposes. A cell could originate from any organism of interest, e.g., a vertebrate, e.g., a mammal. In some embodiments, a cell is a primate cell, e.g., a monkey cell or a human cell. A cell could be a primary cell, immortalized cell, cancer cell, etc. Often, a cell is a member of a population of cells which is composed of cells that are substantially genetically identical, e.g., a cell line. A cell line can be descended from a single cell or from multiple cells isolated from a single individual. A cell can originate from a tissue or organ of interest or can have a property of interest. In some embodiments, a cell is an epithelial cell, fibroblast, kidney cell, rhabdosarcoma or rhabdomyosarcoma, lung, or bronchial cell, pre-adipocyte, or adipocyte. In some embodiments a cell originates from breast, bladder, bone, brain, bronchus, cervix, colon, endometrium, esophagus, larynx, liver, lung, nerve, muscle, ovary, pancreas, prostate, stomach, kidney, skin, testis, or thyroid gland. Numerous cell lines are known in the art, many of which can be obtained from repositories such as the American Type Culture Collection, Coriell Cell Repositories, European Collection of Cell Cultures, Japanese Collection of Research Bioresources, or from a variety of commercial suppliers. In some embodiments, a pre-adipocyte is a 3T3-L1 cell. In some embodiment, a cell is a COS cell, e.g., a COS-1 or COS-7 cell. In some embodiments, a cell is a HeLa cell. In some embodiments, a cell is a Vero, RD, CHO, HEK-293, HMEC, MDCK, NIH-3T3, HEp-2, A549, or BEAS-2B cell. In some embodiments, a cell is a tumor cell. In some embodiments a tumor cell originates from a carcinoma. In some embodiments a tumor cell originates from a sarcoma. In some embodiments a tumor cell originates from a hematologic malignancy, e.g., a lymphoma or leukemia or myeloma. In some embodiments a tumor cell originates from a breast, bladder, bone, brain, cervical, colon, endometrial, esophageal, head and neck, laryngeal, liver, lung (small cell or non-small cell), ovarian, pancreatic, prostate, stomach, renal, skin (e.g., basal cell, melanoma, squamous cell), testicular, or thyroid cancer. The tumor cell may be a cell of an established tumor cell line (e.g., one of the NCI-60 tumor cell lines) or another tumor cell line known in the art or newly established.

In some embodiments, a cell is a hematopoietic cell. In some embodiments, a cell is a KBM-7 cell or derivative thereof, such as a HAP1 cell. In some embodiments, a cell is a KBM-7 cell or other cell that has been partially reprogrammed by expressing at least one "reprogramming factor" therein or exposing the cell to at least one "reprogramming agent" (e.g., an agent that induces expression of an endogenous reprogramming factor or substitutes for a reprogramming factor). Reprogramming cells, e.g., near-haploid mammalian cells may facilitate their use in identifying PLA2G16 inhibitors and/or antiviral compounds. Such reprogramming may convert the KBM-7 cell (which normally grows in suspension) into an adherent cell, such as a HAP1 cell. As known in the art, mouse and human fibroblasts and various other normal somatic cell types can be reprogrammed in vitro to a pluripotent state through retroviral-mediated introduction of combinations of transcription factors, e.g., the four transcription factors Oct4, Sox2, Klf4, and c-Myc (with c-Myc being dispensable, although omitting c-Myc reduced reprogramming efficiency), or the four transcription factors Oct4, Nanog, Sox2, and Lin28 (see, e.g., Meissner, A., et al., Nat Biotechnol., 25(10):1177-81 (2007); Yu, J., et al, Science, 318(5858):1917-20 (2007); and Nakagawa, M., et al., Nat Biotechnol., 26(1):101-6 (2008). Such transcription factors are often referred to as "reprogramming factors").

In some embodiments, a cell naturally expresses PLA2G16. In some embodiments a cell is modified so that it expresses a PLA2G16 polypeptide at a higher level than would be the case in the absence of the modification. In some embodiments, a cell expresses PLA2G16 at a level at least 25%, 50%, 75%, 90%, 95%, or approximately 100% as high as the expression level present in a HAP1 cell, HeLa cell, or other cell capable of serving as a host cell for a virus of interest. The expression level can be normalized, e.g., based on expression of a "housekeeping" gene. Commonly used housekeeping genes include, e.g., beta-actin, GAPDH, phosphoglycerate kinase, etc. Standard methods of transiently or stably expressing polypeptides in cells can be used.

In some embodiments, a cell is of a type that is known in the art to be naturally susceptible to infection by a virus, e.g., a picornavirus. For example, the cell can be of a type that is normally a target cell of the virus in vivo or a cell line that has been used in the art as a host for a virus in culture. A compound can be tested in cells of multiple different types. For example, a compound can be initially identified as a PLA2G16 inhibitor or antiviral compound in a cell that has convenient properties for screening or performing tests for virus inhibition and then subsequently tested in one or more cells that are natural targets of a virus of interest.

In some embodiments, a cell used in a method described herein is genetically modified or selected to have a property that facilitates its use to test compounds. For example, the cell can be genetically modified or selected to have reduced or absent expression of one or more molecular pumps that may otherwise transport a test compound out of the cell. In some embodiments, the cell is modified to facilitate detection of viral infection. For example, the cell could comprise a reporter gene in which a promoter or other expression control element(s) active only in the presence of viral protein(s) are operably linked to an open reading frame that encodes a readily detectable polypeptide such as a fluorescent protein or enzyme. In another embodiment, a cell expresses a protein that comprises a cleavage site for a viral protease, wherein cleavage of the protein is detectable. For example, the protein may contain a FRET pair (e.g., polypeptides that are a FRET donor and acceptor pair) separated by a domain containing a protease cleavage site. Cleavage by the protease results in separation of the members of the FRET pair, resulting in a disruption of FRET, which can be detected and serve as an indicator of viral infection. In another embodiment, a cell-permeable substrate for a viral protease is introduced into the cells. A candidate antiviral compound, e.g., a compound that inhibits PLA2G16 activity, can be tested in such cells to confirm that it inhibits viral infection.

Cells can be contacted with test compound(s) and/or virus for various periods of time. In certain embodiments cells are contacted with test compound(s) and/or virus for between 1 hour and 20 days, e.g., for between 12 and 48 hours, between 48 hours and 5 days, e.g., about 3 days, between 5 days and 10 days, or any intervening range or particular value. In some embodiments, cells are contacted with a virus for at least a time sufficient for completion of one or more rounds of viral replication and production of progeny virus. In some embodiments, cells are contacted with a virus for at least a time sufficient for production of plaques that are detectable under a light microscope. Cells can be contacted with a test compound during all or part of a culture period. If desired, the test compound can be removed prior to assessing PLA2G16 activity or viral infection. In some embodiments, cells are contacted with a virus prior to contacting the cells with the test compound. In other embodiments, cells are contacted with the test compound prior to contacting them with a virus. The absolute number of virus and the multiplicity of infection (MOI) can vary. "Multiplicity of infection" refers to the ratio of infectious agents (e.g., viruses) to infection targets (e.g., In some embodiments an MOI of between $10^{-4}$ and $10^{2}$ is used.

For example, an MOI of between 0.001 and 10, e.g., between 0.01 and 1, can be used. In some embodiments, an amount of virus suitable to produce a pathologic change in between 10% and 100% of cells is used. One of skill in the art will be able to determine a suitable amount of virus to use so as to be able to detect an effect on viral infection. A range of dilutions of a virus stock can be tested to identify an appropriate amount. Cells are maintained in culture for a suitable time period after contacting them with the virus. Typically, the time period will be sufficient for the virus to enter cells and for at least one event indicative of viral infection to occur. Such event may be a detectable effect of a viral gene product(s) on the cell and/or the synthesis or partial synthesis of at least one viral gene product. In general, the time period will be sufficient to detect a difference between the effect of the virus on the cells in the absence of a PLA2G16 inhibitor versus in the presence of a PLA2G16 inhibitor. A detectable effect of a virus on a cell could be an alteration (e.g., a decrease) in synthesis of some or most cellular RNA(s) or protein(s), induction of an antiviral response (e.g., induction of interferon target gene(s) such as the gene encoding 2'5'-oligoadenylate synthetase), a morphological effect such as chromatin condensation, nuclear blebbing, proliferation of membranous vesicles; leakage of intracellular contents; cytotoxicity; cleavage of a substrate by a virus-specific enzyme (e.g., a protease), etc. Cytotoxicity can be assessed e.g., by detecting cell lysis (which may be evident as clear areas or "plaques" in a cell monolayer) or using any of a variety of assays for cell viability and/or proliferation such as a cell membrane integrity assay, a cellular ATP-based viability assay, a mitochondrial reductase activity assay, a BrdU, EdU, or H3-Thymidine incorporation assay, a DNA content assay using a nucleic acid dye, such as Hoechst Dye, DAPI, Actinomycin D, 7-aminoactinomycin D or propidium iodide, a cellular metabolism assay such as AlamarBlue, MTT, XTT, and CellTitre Glo, etc. Plaque assays are a well established means of assessing viral titer and detecting the effect of compounds on viral infectivity. In some embodiments, a plaque assay involves inoculating a standard viral stock into multiple identical cell cultures, e.g., grown in wells of a multiwell plate. A solidifying agent, e.g., agarose, may be added to minimize spread of the virus through the culture medium. The viral titer of the stock is usually predetermined and is selected to yield a countable number of plaques in each well. Different concentrations of the test compound are introduced into a series of wells. The effect of the compound may be expressed as the 50% inhibitory concentration ($IC_{50}$), defined as the lowest concentration of compound that results in a 50% decrease in the number of viral plaques compared with a control well that does not contain the compound. If desired, an $IC_{90}$ can be assessed in a similar manner. A compound that significantly decreases an effect of the virus is an inhibitor of infection by the virus. For example, a compound that significantly decreases the number and/or size of viral plaques caused by a given amount of virus is an inhibitor of viral infection. Optionally, an IC50 or IC90 is determined. In some embodiments, one or more compound(s) with a desired C50 or IC90 is selected. In some embodiments, an IC50 and/or IC90 is no greater than 100 mg/ml, e.g., no greater than 10 mg/ml, e.g., no greater than 1.0 mg/ml, e.g., no greater than 100 µg/ml, e.g., no greater than 10 e.g., no greater than 5 µg/ml or no greater than 1 µg/ml. In some embodiments, an IC50 and/or IC90 is less than or equal to 500 µM. In some embodiments, an IC50 and/or IC90 less than or equal to 100 µM. In some embodiments, an IC50 and/or IC90 less than or equal to 10 µM. In some embodiments, an IC50 and/or IC90 is in the nanomolar range, i.e., less than or equal to 1 µM.

In some embodiments, a high throughput screen (HTS) is performed. A high throughput screen can utilize cell-free or cell-based assays. High throughput screens often involve testing large numbers of compounds with high efficiency, e.g., in parallel. For example, tens or hundreds of thousands of compounds can be routinely screened in short periods of time, e.g, hours to days. Often such screening is performed in multiwell plates containing, e.g., 96, 384, 1536, 3456, or more wells (sometimes referred to as microwell or microtiter plates or dishes) or other vessels in which multiple physically separated cavities are present in a substrate. High throughput screens can involve use of automation, e.g., for liquid handling, imaging, data acquisition and processing, etc. Without limiting the invention in any way, certain general principles and techniques that may be applied in embodiments of a HTS of the present invention are described in Macarrón R & Hertzberg R P. Design and implementation of high-throughput screening assays. Methods Mol Biol., 565:1-32, 2009 and/or An W F & Tolliday N J., Introduction: cell-based assays for high-throughput screening. Methods Mol Biol. 486:1-12, 2009, and/or references in either of these. Exemplary methods are also disclosed in High Throughput Screening: Methods and Protocols (Methods in Molecular Biology) by William P. Janzen (2002) and High-Throughput Screening in Drug Discovery (Methods and Principles in Medicinal Chemistry) (2006) by Jorg Hüser.

In some embodiments, a first screen is performed to identify compounds that bind to and/or inhibit PLA2G16 polypeptide, and the ability of such compounds to inhibit viral infection is then assessed. In some embodiments, test compounds are first tested in a cell-based assay to identify compound(s) that inhibit viral infection and are then tested to determine whether they inhibit PLA2G16.

The invention provides compositions comprising components appropriate to perform any of the inventive methods, e.g., any of the methods of identifying a candidate antiviral compound. In some embodiments, an assay system comprises components suitable for identifying a PLA2G16 inhibitor. In some embodiments, a composition comprises components appropriate to perform any of the inventive methods of validating a candidate antiviral compound. In some embodiments, the composition comprises components appropriate to confirm that a candidate antiviral compound inhibits viral infection in cultured cells or in vivo. In one aspect, an inventive composition comprises (i) isolated cells that express a PLA2G16 polypeptide; (ii) a virus capable of infecting the cells; and (iii) a test compound. In some embodiments, the virus is a Picornavirus, e.g., a pathogenic Picornavirus. The virus is typically present in the composition in amounts suitable for detecting virus infection by the cells. Such amounts are typically greater than might happen by chance if cultured cells happen to be exposed to an environment where there is an individual infected by the virus. In some embodiments, the ratio of viral particles (e.g., infectious viral particles) to cells is at least $1:10^6$, at least $1:10^5$, e.g., at least $1:10^4$, at least $1:10^3$, at least $1:10^2$, at least $1:10$, or at least 1:1. In some embodiments, there are more viral particles (e.g., infectious viral particles) than cells. The test compound can be, e.g, any of the compounds discussed above. In some embodiments, the test compound is a phospholipase A2 inhibitor, e.g, a PLA2G16 inhibitor. In some embodiments, the test compound is a small molecule. In some embodiments, the test compound has been determined to bind to and/or inhibit PLA2G16 in at least one cell-free or cell-based assay.

Compounds identified in cell-free and/or cell-based assays can be tested in subjects (e.g., non-human vertebrates) to assess their ability to inhibit viral infection in vivo. Animal models for viral infection are known in the art. An animal can be, e.g., a rodent, non-human primate, dog, cat, etc. In one embodiment, an animal model is a murine model of coxsackievirus B3 (CVB3)-induced myocarditis. See, e.g., Szalay G, Ongoing coxsackievirus myocarditis is associated with increased formation and activity of myocardial immunoproteasomes, Am J Pathol., 168(5):1542-52, 2006, and references therein. In one embodiment, an animal model is a mouse model for EV71 infection. See, e.g. Wang, Y. F., et al., A mouse-adapted enterovirus 71 strain causes neurological disease in mice after oral infection. J. Virol. 78:7916-7924, 2004, which describe an animal model in which mice are orally inoculated with EV71. Mice may be monitored daily for signs of disease and survival. In another embodiment, an attenuated mengovirus is used in a rodent model for rhinovirus infection. See, e.g., Rosenthal L A, A rat model of picornavirus-induced airway infection and inflammation. Virol J., 6:122, 2009. Tissues or body fluids can be collected after infection to determine viral titers and/or to evaluate other signs of viral infection. For example, viral RNA or protein can be detected using standard methods such as RT-PCR (for RNA) or immunological methods for proteins. See, e.g., Li, Z. H., et al., Ribavirin reduces mortality in enterovirus 71-infected mice by decreasing viral replication. J. Infect. Dis. 197:854-857, 2008).

The invention further provides a non-human subject e.g., a vertebrate, wherein the non-human subject has been inoculated with or exposed to a virus to which it is normally susceptible, or that is suffering from a viral infection, and wherein a PLA2G16 inhibitor has been administered to the subject. "Inoculation" with a virus means that the virus has been introduced into the subject's body. Exposure can involve inoculating a subject or placing the virus and subject in reasonably close proximity so as to increase the likelihood that the subject will encounter the virus. Inoculation can be by any appropriate route. Inoculation or exposure will typically involve sufficient amount of virus to produce evident disease in at least 25% of a population of that species in the absence of an antiviral compound. The PLA2G16 inhibitor can be, e.g, any of the compounds discussed above or identified according to an inventive method. In some embodiments, the test compound is a small molecule. In some embodiments, the test compound has been determined to bind to and/or inhibit PLA2G16 in at least one cell-free or cell-based assay. The non-human subject can be monitored, e.g., to assess the safety, tolerability, and/or efficacy of the compound as an antiviral agent. Assessing the effect of a PLA2G16 inhibitor in a subject infected with a virus is an aspect of the invention.

In some embodiments, the invention provides a near-haploid cell that has an insertion into the PLA2G16 locus or otherwise lacks expression of PLA2G16. The near-haploid cell is of a species, e.g., a mammal, whose somatic cells are normally diploid. In some embodiments, the invention provides a near-haploid cell that expresses a catalytically inactive mutant PLA2G16 polypeptide, wherein optionally the near-haploid mutant cell line has an insertion in the endogenous PLA2G16 gene. In some embodiments, the invention provides a near-haploid cell that expresses a tagged functional PLA2G16 polypeptide, wherein optionally the near-haploid mutant cell line has an insertion in the endogenous PLA2G16 gene. A near-haploid mammalian cell, as used herein, refers to a mammalian cell in which no more than 5 chromosomes are present in two or more copies. In some embodiments a near-haploid mammalian cell has no more than 1, 2, 3, or 4 chromosomes present in two or more copies. The "near-haploid" cell should be understood to include haploid cells.

Further provided are cell lines derived from cells that lack expression of functional PLA2G16, e.g., cell lines composed of cells that have an insertion into the PLA2G16 gene. In some embodiments, a cell line expresses a catalytically inactive mutant PLA2G16 polypeptide, which is tagged in some embodiments. In some embodiments, a near-haploid cell line eventually gains chromosomes during culture so that it is no longer near-haploid. In some embodiments the cell line may become near diploid or diploid.

The invention further provides kits comprising one or more components of any of the inventive compositions and/or components suitable for performing any of the inventive methods. The components can be packaged individually, e.g., in individual containers, which may be provided within a larger container. A kit can contain instructions for using the contents to perform any of the methods, e.g., to identify or characterize an antiviral compound.

In some embodiments, computational approaches are employed to identify and/or characterize compounds that inhibit PLA2G16. For example, a three-dimensional structure of a PLA2G16 polypeptide can be determined or an approximate structure generated using, e.g., nuclear magnetic resonance, homology modeling, and/or X-ray crystallography. Optionally the structure of the polypeptide with a ligand (e.g., an inhibitor) bound thereto is determined. In some embodiments, a computational approach is used in the initial identification of candidate PLA2G16 inhibitors (sometimes termed "virtual screening"). Structures of candidate compounds can be screened for ability to bind to the PLA2G16 polypeptide, e.g., to a region (e.g., a "pocket") accessible to the compound. The region could be a known or potential active site or any region accessible to the compound, e.g., a concave region on the surface or a cleft. A variety of docking and pharmacophore-based algorithms have been developed, and computer programs implementing such algorithms are available. Commonly used programs include Gold, Dock, Glide, FlexX, Fred, and LigandFit (including the most recent releases thereof). See, e.g., Ghosh, S., et al., Current Opinion in Chemical Biology, 10(3): 194-2-2, 2006; McInnes C., Current Opinion in Chemical Biology; 11(5): 494-502, 2007, and references in either of the foregoing articles, which are incorporated herein by reference. In some embodiments, a virtual screening algorithm involves two major phases: searching (also called "docking") and scoring. During the first phase, the program automatically generates a set of candidate complexes of two molecules (test compound and target molecule) and determines the energy of interaction of the candidate complexes. The scoring phase assigns scores to the candidate complexes and selects a structure that displays favorable interactions based at least in part on the energy. To perform virtual screening, this process is repeated with a large number of test compounds to identify those that display the most favorable interactions with the target. In some embodiments, low-energy binding modes of a small molecule within an active site or possible active site are identified. Variations can include the use of rigid or flexible docking algorithms and/or including the potential binding of water molecules.

Numerous small molecule structures are available and can be used for virtual screening. For example, ZINC is a publicly available database containing structures of millions of commercially available compounds that can be used for virtual screening on the World Wide Web (Shoichet, J. Chem. Inf. Model., 45(1):177-82, 2005). A database containing about 250,000 small molecule structures is available on the National Cancer Institute (U.S.) website. In some embodiments, multiple small molecules are screened, e.g., up to 50,000; 100,000; 250,000; 500,000, or up to 1 million, 2 million, 5 million, 10 million, or more. Compounds can be scored and, optionally, ranked by their potential to bind to the target. Compounds identified in virtual screens can be tested in cell-free or cell-based assays or in animal models to confirm their ability to inhibit PLA2G16 activity and/or viral infection.

Computational approaches can be used to predict one or more physico-chemical, pharmacokinetic and/or pharmacodynamic properties of compounds identified in actual or virtual screens. For example, absorption, distribution, metabolism, and excretion (ADME) parameters can be predicted. Such information can be used, e.g., to select hits for further testing or modification. For example, small molecules having characteristics typical of "drug-like" molecules can be selected and/or small molecules having one or more undesired characteristics can be avoided. In one embodiment, compounds that satisfy at least some of the Lipinski "rule of five" criteria are selected.

In one aspect, the invention provides a computer-readable medium on which are stored results of a screen to identify compounds that inhibit PLA2G16. The results may be stored in a database and can include any screening protocols, results obtained from the screen or from additional screens, and/or protocols of or results obtained from tests performed on compounds identified in the screen (e.g., tests in animal models of viral infection).

Additional compounds that inhibit PLA2G16 can be identified or designed based on initial compounds ("hits") identified in an actual or virtual screen such as those described above. Such additional compounds and methods of designing or synthesizing them are an aspect of the invention. In some embodiments, structures of hit compounds are examined to identify a pharmacophore, which can be used to design additional compounds ("derivatives").

An additional compound may, for example, have one or more improved (i.e., more desirable) pharmacokinetic and/or pharmacodynamic properties as compared with an initial hit or may simply have a different structure. For example, a compound may have higher affinity for the molecular target of interest (e.g., PLA2G16), lower affinity for a non-target molecule, greater solubility (e.g., increased aqueous solubility), increased stability, increased bioavailability, and/or reduced side effect(s), etc. Optimization can be accomplished through empirical modification of the hit structure (e.g., synthesizing compounds with related structures and testing them in cell-free or cell-based assays or in non-human animals) and/or using computational approaches. Such modification can make use of established principles of medicinal chemistry to predictably alter one or more properties.

In some embodiments, a PLA2G16 inhibitor is modified or incorporates a moiety that enhances cell uptake, stability (e.g., in serum), increases half-life, reduces toxicity or immunogenicity, or otherwise confers a desirable property on the compound. In some embodiments, a PLA2G16 inhibitor comprises a protein transduction domain (PTD). A PTD or cell penetrating peptide (CPP) is a peptide or peptoid that can traverse the plasma membrane of many, if not all, mammalian cells. A PTD can enhance uptake of a moiety to which it is attached or in which it is present. Often such peptides are rich in arginine. For example, the PTD of the Tat protein of human immunodeficiency viruses types 1 and 2 (HIV-1 and HIV-2) has been widely studied and used to transport cargoes into mammalian cells. See, e.g., Fonseca S B, et al., Adv Drug Deliv Rev., 61(11):953-64, 2009; Heitz F, et al., Br J Pharmacol., 157(2):195-206, 2009, and references in either of the foregoing, which are incorporated herein by reference. In some embodiments, a PTD is used to enhance cell uptake of a small molecule, siRNA, aptamer, or polypeptide that inhibits PLA2G16.

In some embodiments, a compound causes a decrease in PLA2G16 level or catalytic activity of at least 50% when used in a cell-free or cell-based assay at a concentration equal to or less than approximately 1 mM, 500 µM, 100 µM, 50 µM, 10 µM, 5 µM, or 1 µM. In some embodiments, a compound causes a decrease in PLA2G16 activity of at least 50% (i.e., a decrease to 50% or less of the activity that would be expected in the absence of the compound) when used in a cell-free or cell-based assay at lower concentrations, e.g., equal to or less than approximately 500 nM, 100 nM, 50 nM, or 10 nM or less. In some embodiments, a compound causes a decrease in PLA2G16 activity of at least 50% when used at a concentration between 0.1-10 nM. Various methods suitable for assessing PLA2G16 level or activity are mentioned above. In some embodiments, a compound causes a decrease in production or progeny virus of at least 50% (i.e., a decrease to 50% or less of the number of progeny viruses that would be expected in the absence of the compound) or a decrease in cytopathic effect of at least 50% when used in a suitable cell culture system at a concentration equal to or less than approximately 1 mM, 500 µM, 100 µM, 50 µM, 10 µM, 5 µM, or 1 µM. In some embodiments, a compound causes a decrease in production or progeny virus or cytopathic effect of at least 50% when used in a suitable cell culture system at lower concentrations, e.g., equal to or less than approximately 500 nM, 100 nM, 50 nM, or 10 nM or less. In some embodiments, a compound causes a decrease in production or progeny virus of at least 50% when used in a suitable cell culture system when used at a concentration between 0.1-10 nM. Various methods suitable for assessing virus production or cytopathic effect are mentioned above. In other aspects, a compound causes a decrease of at least 25%, or at least 75%, or at least 90%, in PLA2G16 level, catalytic activity, and/or production of progeny virus or cytopathic effect.

It is noted that, in general, the PLA2G16 inhibitors and methods of use thereof do not depend on, and are not limited by, the way in which an inhibitor was identified or generated or the components used to identify or generate the PLA2G16 inhibitor. For example, in certain embodiments of the invention a PLA216 inhibitor identified using a human PLA2G16 polypeptide and/or using human cells is used to treat humans. In certain embodiments of the invention a PLA216 inhibitor identified using a human PLA2G16 polypeptide and/or using human cells is used to treat non-human animals, e.g., non-human vertebrate animals. In some embodiments, a PLA216 inhibitor identified using a PLA2G16 polypeptide of a non-human animal and/or using cells derived from a non-human animal is used to treat non-human animals of that species, different non-human animal species, and/or humans. A PLA216 inhibitor that inhibits infection by a virus that infects human cells could be used to treat humans, non-human animals, or both, in various embodiments of the invention. For example, in certain embodiments a PLA216 inhibitor that inhibits infection by a virus that infects human cells is used to inhibit infection by a virus that mainly or only infects cells of a non-human animal.

VII. Pharmaceutical Compositions, Methods of Treatment, and Other Applications A compound identified, selected, or designed according to a method described herein can have a variety of uses. In some embodiments, a compound is useful for therapeutic purposes, e.g., as a therapeutic agent for a subject in need of treatment for a viral infection.

In some embodiments, a subject is "suffering from" a viral infection when excessive numbers of a viral population are present in or on the organism's body and/or when the effects of the presence of a virus population(s) is damaging the cells or other tissue of an organism. A subject can be "in need of treatment for" a viral infection if, for example, the subject is suffering from a viral infection or is at increased risk of developing a viral infection as compared with (i) most members of the general population; and/or (ii) the level of risk that the subject typically experiences.

The invention contemplates treatment of a wide variety of viral infections in human and/or animal subjects, e.g., infection due to any of the viruses discussed herein. In some embodiments, the virus is a picornavirus, e.g., a cardiovirus, echovirus, enterovirus (e.g., a coxsackievirus, rhinovirus, or echovirus), or hepatovirus, or rhinovirus. In some embodiments, the virus clusters phylogenetically within the enterovirus genus. In some embodiments, the picornavirus is classified with a species selected from the group consisting of: Human enterovirus A, Human enterovirus B, Human enterovirus C, Human enterovirus D, Simian enterovirus A, Bovine enterovirus, Porcine enterovirus B, Human rhinovirus A, Human rhinovirus B and Human rhinovirus C. In some embodiments, the picornavirus is classified with a species selected from the group consisting of: Human enterovirus A, Human enterovirus B, Human enterovirus C, Human enterovirus D, Human rhinovirus A, Human rhinovirus B and Human rhinovirus C. In some embodiments, the virus is of a serotype that has been deposited at the American Type Culture Collection (ATCC) or National Collection of Pathogenic Viruses (NCPV) of the Health Protection Agency of the UK and, optionally, is available for distribution.

The invention provides methods of treating diseases and medical conditions resulting from viral infection, e.g., by a picornavirus. Exemplary diseases and conditions include, e.g., asthma exacerbation, bronchiolitis, colitis, common cold, COPD exacerbation, encephalitis, encephalomyelitis, enterocolitis, foot-and-mouth disease, hand-foot-and-mouth disease, gastroenteritis, herpangina, hepatitis, meningitis, meningoencephalitis, myocarditis, pancreatitis, polio, and pneumonia. In some aspects, the invention contemplates ex vivo uses of the PLA2G16 inhibitors. For example, organs, tissues, or cells intended for use in transplantation (e.g., xenotransplantation or transplantation into an individual of the same species) can be contacted ex vivo with a PLA2G16 inhibitor, e.g., to reduce the likelihood of transmitting a viral infection to the recipient. In another embodiment, recipients of an organ, tissue, or cell transplant can be treated with a PLA2G16 inhibitor, e.g., to reduce the likelihood of contracting a viral infection from the transplanted cells, tissues, or organ(s). Such treatment could commence prior to, during, or after the transplant procedure.

In some embodiments, the virus is one for which an effective vaccine does not exist, is not in commercial use, or is not widely used. For example, coxsackievirus B3 is widespread in the human population and causes serious diseases such as myocarditis or pancreatitis. Coxsackievirus B4 can cause a broad range of diseases such as aseptic meningitis, meningoencephalitis, myocarditis, hepatitis, pancreatitis, gastroenteritis, necrotizing enterocolitis, and pneumonia. However, despite the clinical significance of these viruses, there is no commercially available and clinically applicable prophylactic vaccine. Enterovirus 71 is another virus of significant medical importance for which a vaccine is not available.

In some embodiments, the virus is one for which an effective vaccine is in commercial use and/or available. Without limitation, the inventive methods may find use to treat subjects who are unvaccinated or otherwise non-immune, to treat subjects infected with a strain of virus against which a vaccine may not afford sufficient immunity, etc. In some embodiments, the individual is infected by a vaccine strain, e.g., an attenuated strain. In some embodiments, the invention provides methods of treating human subjects who may have been exposed to or infected by a poliovirus, e.g., unvaccinated or otherwise non-immune individuals (e.g., immunocompromised individuals), in the setting of a polio outbreak, individuals who travel to or from a region where polio has not been eradicated, etc. In some embodiments, the invention contemplates treating livestock in need of treatment for foot-and-mouth disease virus, e.g., in the setting of a foot-and-mouth disease outbreak.

In some embodiments, a PLA2G16 inhibitor, e.g., a PLA2G16 inhibitor identified according to the instant invention, can have one or more therapeutic uses in addition to, or instead of, for treating a viral infection. In some embodiments, a PLA2G16 inhibitor is useful as a therapeutic agent for a subject in need of treatment for excess body fat, a disease associated with excess body fat, or a metabolic disorder. Excess body fat can be a condition of having more body fat than desired by the subject or having an amount of body fat that is considered within sound medical judgement to contribute to a disease or to confer an increased risk of disease. In some embodiments, a compound is useful to treat as atherosclerosis or vascular disease (e.g., cardiovascular or cerebrovascular disease). In some embodiments, the compound is useful for treating obesity, e.g., in a subject having a body mass index (BMI) greater than or equal to 30. In some embodiments, a compound is useful to treat a metabolic disorder, e.g., diabetes (e.g., type II diabetes, also called diabetes mellitus), glucose intolerance, insulin resistance, metabolic syndrome, leptin deficiency, or hypertriglyceridemia.

Inventive methods of treatment can include a step of identifying a subject suffering from or at risk of a viral infection, a step of identifying a virus suspected of causing an infection, a step of selecting a therapeutic agent or combination of agents based at least in part on the identity or suspected identity of the virus and/or the location or characteristics of the infection, and/or a step of prescribing, providing, or administering a selected agent to the subject. In certain embodiments of the invention, the method includes determining that a subject has a significant likelihood (e.g., at least 5%) of suffering from or being at risk of infection by a virus, e.g., a picornavirus. A subject can be "at risk of an infection" in any of a variety of circumstances. "At risk of" implies at increased risk of, relative to the risk such subject would have in the absence of one or more circumstances, conditions, or attributes of that subject, and/or relative to the risk that an average, healthy member of the population would have and/or relative to the risk that the subject had at a previous time. The population is typically a group of subjects of the same species. Examples of conditions that place a subject "at risk" include, but are not limited to, immunodeficiencies (e.g., genetic immunodeficiencies); prior treatment with antibiotic agent(s) that may have reduced or eliminated normal microbial flora; treatment with agent(s) that suppress the immune system (e.g., cancer chemotherapy, immunosuppressive agents); exposure to agents that damage the immune system; chronic diseases such as diabetes, COPD, or cystic fibrosis; coexisting or preceding bacterial or fungal infection; surgery or other trauma; infancy or old age; occupations, events, or living conditions that entail exposure to pathogenic viruses, etc., or any other condition that within the judgement and skill of the subject's health care provider place the subject at increased risk. In some embodiments, subject can be at increased risk of developing a viral infection if the subject has been recently exposed to a pathogenic virus, e.g., the subject has had contact with an individual known or believed to be suffering from a viral infection (e.g., exposure within the preceding 1, 2, 3, or 4 weeks or within the "incubation period" of the virus). In one embodiment, an incubation period refers to the range of times following exposure to a virus during which 10%-90% of individuals who develop symptomatic infection would do so.

Any of a variety of methods may be employed to identify a subject in need of treatment (e.g., a subject at risk of or suffering from a viral infection) according to the present invention. For example, such methods include clinical diagnosis based at least in part on symptoms, medical history (if available), physical examination, laboratory tests, imaging studies, immunodiagnostic assays, nucleic acid based diagnostics, and/or isolation and culture of potentially causative viruses from samples, such as blood, urine, sputum, saliva, nasal secretions, stool, synovial fluid, cerebrospinal fluid, bronchealveolar lavage, pus, or any sample of body fluid, cells, or tissue. In some embodiments, diagnosis can at least in part be based on serology (e.g., detection of an antibody that specifically reacts with the virus). In some embodiments, diagnosis can be based at least in part on isolating the virus and/or a viral genome or gene product from the subject. In some embodiment, the sample is tested for a viral genome or gene product. For example, PCR or other nucleic acid amplification methods can be used to amplify viral DNA or RNA, which can be detected in a variety of ways such as hybridization-based methods. Multiplexed PCR or other amplification methods are useful. Signal amplification assays include branched chain DNA assays and hybrid capture assays. Transcription based amplification and nucleic acid sequence based amplification (NASBA) may be used. Microarrays, e.g., oligonucleotide microarrays, can be used. A microarray can be a solid phase or suspension array (e.g., a microsphere-based approach such as the Luminex platform). Immunological methods (e.g., ELISA or particle agglutination) can be used to detect viral antigens, e.g., polypeptides. Labelled compounds that specifically bind to a viral component can be used. In some embodiments, a virus is grown in cell culture and identified. Identification can be based on morphology, effect on cultured cells, and/or detection of virus specific nucleic acids and/or polypeptides. In some embodiments, a specific virus is not identified, while in other embodiments a specific virus is identified.

The compounds and compositions disclosed herein and/or identified or validated using a method described herein may be administered by any suitable means such as orally, intranasally, subcutaneously, intramuscularly, intravenously, intra-arterially, parenterally, intraperitoneally, intrathecally, intratracheally, ocularly, sublingually, vaginally, rectally, dermally, or by inhalation, e.g., as an aerosol. Depending upon the type of condition (e.g., viral infection) to be treated, compounds of the invention may, for example, be inhaled, ingested or administered by systemic routes. Thus, a variety of administration modes, or routes, are available. The particular mode selected will depend, of course, upon the particular compound selected, the particular condition being treated and the dosage required for therapeutic efficacy. The methods of this invention, generally speaking, may be practiced using any mode of administration that is medically or veterinarily acceptable, meaning any mode that produces acceptable levels of efficacy without causing clinically unacceptable (e.g., medically or veterinarily unacceptable) adverse effects. The term "parenteral" includes intravenous, intramuscular, intraperitoneal, subcutaneous, intraosseus, and intrasternal injection, or infusion techniques. In some embodiments, a route of administration is parenteral or oral. Optionally, a route or location of administration is selected based at least in part on the particular viral infection and/or location of infected tissue. For example, a compound may be delivered to or near an infected tissue. In some embodiments, inhaled medications are of use. Such administration allows direct delivery to the lung, for example in subjects with a respiratory infection, although it could also be used to achieve systemic delivery. Several types of metered dose inhalers are regularly used for administration by inhalation. These types of devices include metered dose inhalers (MDI), breath-actuated MDI, dry powder inhaler (DPI), spacer/holding chambers in combination with MDI, and nebulizers. In other embodiments, intrathecal administration may be of use, e.g., in a subject with a viral infection of the central nervous system. Other appropriate routes and devices for administering therapeutic agents will be apparent to one of ordinary skill in the art.

Suitable preparations, e.g., substantially pure preparations, of a PLA2G16 inhibitor may be combined with one or more pharmaceutically acceptable carriers or excipients, etc., to produce an appropriate pharmaceutical composition. The invention provides a variety of pharmaceutically acceptable compositions for administration to a subject comprising (i) a PLA2G16 inhibitor; and (ii) a pharmaceutically acceptable carrier or excipient. The term "pharmaceutically acceptable carrier or excipient" refers to a carrier (which term encompasses carriers, media, diluents, solvents, vehicles, etc.) or excipient which does not significantly interfere with the biological activity or effectiveness of the active ingredient(s) of a composition and which is not excessively toxic to the host at the concentrations at which it is used or administered. Other pharmaceutically acceptable ingredients can be present in the composition as well. Suitable substances and their use for the formulation of pharmaceutically active compounds is well-known in the art (see, for example, "Remington's Pharmaceutical Sciences", E. W. Martin, 19th Ed., 1995, Mack Publishing Co.: Easton, Pa., and more recent editions or versions thereof, such as Remington: The Science and Practice of Pharmacy. 21st Edition. Philadelphia, Pa. Lippincott Williams & Wilkins, 2005, for additional discussion of pharmaceutically acceptable substances and methods of preparing pharmaceutical compositions of various types, which are incorporated herein by reference in their entirety).

A pharmaceutical composition is typically formulated to be compatible with its intended route of administration. For example, preparations for parenteral administration include sterile aqueous or non-aqueous solutions, suspensions, and emulsions. Aqueous carriers include water, alcoholic/aqueous solutions, emulsions or suspensions, including saline and buffered media, e.g., sodium chloride solution, Ringer's dextrose, dextrose and sodium chloride, lactated Ringer's. Examples of non-aqueous solvents are propylene glycol, polyethylene glycol, vegetable oils such as olive oil, and injectable organic esters such as ethyl oleate, fixed oils, polyethylene glycols, glycerine, propylene glycol or other synthetic solvents; preservatives, e.g., antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. pH can be adjusted with acids or bases, such as hydrochloric acid or sodium hydroxide. Such parenteral preparations can be enclosed in ampoules, disposable syringes or multiple dose vials made of glass or plastic. Pharmaceutical compositions and compounds for use in such compositions may be manufactured under conditions that meet standards or criteria prescribed by a regulatory agency. For example, such compositions and compounds may be manufactured according to Good Manufacturing Practices (GMP) and/or subjected to quality control procedures appropriate for pharmaceutical agents to be administered to humans.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Suitable excipients for oral dosage forms are, e.g., fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP). If desired, disintegrating agents may be added, such as the cross linked polyvinyl pyrrolidone, agar, or alginic acid or a salt thereof such as sodium alginate. Optionally the oral formulations may also be formulated in saline or buffers for neutralizing internal acid conditions or may be administered without any carriers. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art.

Formulations for oral delivery may incorporate agents to improve stability in the gastrointestinal tract and/or to enhance absorption.

For administration by inhalation, inventive compositions may be delivered in the form of an aerosol spray from a pressured container or dispenser which contains a suitable propellant, e.g., a gas such as carbon dioxide, a fluorocarbon, or a nebulizer. Liquid or dry aerosol (e.g., dry powders, large porous particles, etc.) can be used. The present invention also contemplates delivery of compositions using a nasal spray or other forms of nasal administration.

For topical applications, pharmaceutical compositions may be formulated in a suitable ointment, lotion, gel, or cream containing the active components suspended or dissolved in one or more pharmaceutically acceptable carriers suitable for use in such composition.

For local delivery to the eye, the pharmaceutically acceptable compositions may be formulated as solutions or micronized suspensions in isotonic, pH adjusted sterile saline, e.g., for use in eye drops, or in an ointment.

Pharmaceutical compositions may be formulated for transmucosal or transdermal delivery. For transmucosal or transdermal administration, penetrants appropriate to the barrier to be permeated may be used in the formulation. Such penetrants are generally known in the art. Inventive pharmaceutical compositions may be formulated as suppositories (e.g., with conventional suppository bases such as cocoa butter and other glycerides) or as retention enemas for rectal delivery.

In some embodiments, a pharmaceutical composition includes one or more agents intended to protect the active agent(s) against rapid elimination from the body, such as a controlled release formulation, implants, microencapsulated delivery system, etc. Compounds may be encapsulated or incorporated into particles, e.g., microparticles or nanoparticles. Biodegradable, biocompatible polymers can be used, such as ethylene vinyl acetate, polyanhydrides, polyglycolic acid, PLGA, collagen, polyorthoesters, polyethers, and polylactic acid. Methods for preparation of such formulations will be apparent to those skilled in the art. For example, and without limitation, a number of particle-based delivery systems are known in the art for delivery of siRNA. The invention contemplates use of such compositions. Liposomes or other lipid-based particles can also be used as pharmaceutically acceptable carriers.

In some embodiments, the invention provides a pharmaceutically acceptable derivative of a PLA2G16 inhibitor, e.g., a PLA2G16 inhibitor described herein or identified or validated according to an inventive method. According to the present invention, a pharmaceutically acceptable derivative of a particular compound includes, but is not limited to, pharmaceutically acceptable salts, esters, salts of such esters, or any other adduct or derivative which upon administration to a subject in need thereof is capable of providing the compound, directly or indirectly. Thus, pharmaceutically acceptable derivatives can include salts, prodrugs, and/or active metabolites. The term "pharmaceutically acceptable salt" refers to those salts which are, within the scope of sound medical judgment, suitable for use in contact with the tissues of humans and/or lower animals without undue toxicity, irritation, allergic response and the like, and which are commensurate with a reasonable benefit/risk ratio. A wide variety of appropriate pharmaceutically acceptable salts are well known in the art. Pharmaceutically acceptable salts include, but are not limited to, those derived from suitable inorganic and organic acids and bases. A pharmaceutically acceptable derivative of a PLA2G16 inhibitor may be formulated and, in general, used for the same purpose(s).

Pharmaceutical compositions of the invention, when administered to a subject, are preferably administered for a time and in an amount sufficient to treat the disease or condition for which they are administered, e.g., a viral infection. Therapeutic efficacy and toxicity of active agents can be assessed by standard pharmaceutical procedures in cell cultures or experimental animals. The data obtained from cell culture assays and animal studies can be used in formulating a range of dosages suitable for use in humans or other subjects. Different doses for human administration can be further tested in clinical trials in humans as known in the art. The dose used may be the maximum tolerated dose or a lower dose. A therapeutically effective dose of an active agent in a pharmaceutical composition may be within a range of about 0.001 to about 100 mg/kg body weight, about 0.01 to about 25 mg/kg body weight, about 0.1 to about 20 mg/kg body weight, about 1 to about 10 mg/kg. Other exemplary doses include, for example, about 1 µg/kg to about 500 mg/kg, about 100 µg/kg to about 5 mg/kg). In some embodiments a single dose is administered while in other embodiments multiple doses are administered. Those of ordinary skill in the art will appreciate that appropriate doses in any particular circumstance depend upon the potency of the agent(s) utilized, and may optionally be tailored to the particular recipient. The specific dose level for a subject may depend upon a variety of factors including the activity of the specific agent(s) employed, severity of the disease or disorder, the age, body weight, general health of the subject, etc.

It may be desirable to formulate pharmaceutical compositions, particularly those for oral or parenteral compositions, in unit dosage form for ease of administration and uniformity of dosage. Unit dosage form, as that term is used herein, refers to physically discrete units suited as unitary dosages for the subject to be treated; each unit containing a predetermined quantity of active agent(s) calculated to produce the desired therapeutic effect in association with an appropriate pharmaceutically acceptable carrier. The invention provides a pharmaceutically acceptable unit dosage form containing, a predetermined amount of a PLA2G16 inhibitor, such amount being appropriate to treat a subject in need of treatment for a viral infection.

It will be understood that a therapeutic regimen may include administration of multiple unit dosage forms over a period of time. In some embodiments, a subject is treated for between 1-7 days. In some embodiments a subject is treated for between 7-14 days. In some embodiments a subject is treated for between 14-28 days. In other embodiments, a longer course of therapy is administered, e.g., over between about 4 and about 10 weeks. In some embodiments a subject is treated at least until at least one symptom or sign of viral infection has started to decrease in severity or has significantly decreased in severity or until a subject is no longer at risk of viral infection. In some embodiments, treatment may be continued indefinitely, e.g., in order to achieve prophylaxis. For example, a subject at risk of recurrent viral infection or wanting to avoid viral infection may be treated for any period during which such risk exists or the subject desires to avoid viral infection. A subject may receive one or more doses a day, or may receive doses every other day or less frequently, within a treatment period.

In some embodiments, two or more different PLA2G16 inhibitors are administered. In some embodiments, a PLA2G16 inhibitor is administered in combination with a second compound useful for treating a viral infection. The phrase "in combination, as used herein, with regard to combination treatment means with respect to administration of first and second compounds, administration performed such that (i) a dose of the second compound is administered before more than 90% of the most recently administered dose of the first agent has been metabolized to an inactive form or excreted from the body; or (ii) doses of the first and second compound are administered within 48 hours of each other, or (iii) the agents are administered during overlapping time periods (e.g., by continuous or intermittent infusion); or (iv) any combination of the foregoing. The compounds may, but need not be, administered together as components of a single composition. In some embodiments, they may be administered individually at substantially the same time (by which is meant within less than 10 minutes of one another). In some embodiments they may be administered individually within a short time of one another (by which is meant less than 3 hours, sometimes less than 1 hour, apart). The compounds may, but need not, be administered by the same route of administration. When administered in combination with a second compound, the effective amount of a first compound needed to elicit a particular biological response may be less or more than the effective amount of the first compound when administered in the absence of the second compound (or vice versa), thereby allowing an adjustment of the amount dose of the either or both agent(s) relative to the amount that would be needed if one compound were administered in the absence of the other. For example, when the compounds of the invention are administered in combination (e.g., a PLA2G16 inhibitor and a second antiviral compound), a sub-therapeutic dosage of either of the compounds, or a sub-therapeutic dosage of both, may be used in the treatment of a subject in need of treatment for a viral infection. In some embodiments, the two compounds are used in combination, the second antiviral compound may in some embodiments be administered at a sub-therapeutic amount to produce a desirable therapeutic result. A "sub-therapeutic amount" as used herein refers to an amount which is less than that amount which would be expected to produce a therapeutic result in the subject if administered in the absence of the other compound, e.g., less than a recommended amount. The effects of multiple compounds may, but need not be, additive or synergistic. One or more of the compounds may be administered multiple times.

In some embodiments, an antiviral agent known in the art as being useful for treating a subject infected with a particular virus, e.g., a Picornavirus, is used as a second compound in combination with a PLA2G16 inhibitor. In some embodiments, an antibody that neutralizes or inhibits the virus is used. In some embodiments, a compound that inhibits viral fusion is used. In some embodiments a protease inhibitor or kinase inhibitor is used. In some embodiments an RNAi agent is used, e.g., an siRNA, e.g., targeting a viral gene. In some embodiments a capsid binding agent is used. In some embodiments, the second compound is, e.g., ruprintrivir, pleconaril, a pyridazinyl oxime ether, or arbidol. See, e.g., Barnard D L., Current status of anti-picornavirus therapies Curr Pharm Des. 12(11):1379-90, 2006; DePalma, A M, et al., Medicinal Research Reviews, 28(6): 823-884, 2008.

In some embodiments, a compound that is not sufficiently active to be therapeutically useful is rendered therapeutically useful when administered in combination with a PLA2G16 inhibitor. In some embodiments, a lower dose of such compound can be used when administered in combination with a PLA2G16 inhibitor.

In some embodiments, the invention provides a composition comprising a PLA2G16 inhibitor and a second compound useful for inhibiting a viral infection, e.g., an infection by a picornavirus. In some embodiments, a unit dosage form comprising the two (or more) agents is provided.

The present invention also provides pharmaceutical packs or kits comprising one or more containers (e.g., vials, ampoules, bottles) containing a pharmaceutically acceptable PLA2G16 inhibitor and, optionally, one or more other pharmaceutically acceptable ingredients. Optionally associated with such container(s) can be a notice in the form prescribed by a governmental agency regulating the manufacture, use or sale of pharmaceutical products, which notice reflects approval by the agency of manufacture, use or sale for human administration. The notice may describe, e.g., doses, routes and/or methods of administration, approved indications (e.g., viral infections that the pharmaceutical composition has been approved for use in treating), mechanism of action, or other information of use to a medical practitioner and/or patient. Different ingredients may be supplied in solid (e.g., lyophilized) or liquid form. Each ingredient will generally be suitable as aliquoted in its respective container or provided in a concentrated form. Kits may also include media for the reconstitution of lyophilized ingredients. The individual containers of the kit are preferably maintained in close confinement for commercial sale.

A virus to be inhibited according to the instant invention may infect a cell type, organ or organ system of interest. For example, in some embodiments the virus infects cells of the gastrointestinal tract. In some embodiments the virus infects the liver, e.g., hepatocytes. In some embodiments the virus infects the respiratory system, e.g., cells of the upper and/or lower respiratory tract. In some embodiments the virus infects muscle cells, e.g., cardiac muscle cells. In some embodiments the virus infects the nervous system (e.g., neurons). In some embodiments the virus infects the central nervous system. In some embodiments the virus infects skin cells (e.g., keratinocytes). In some embodiments the virus infects mucosal cells. In some embodiments the virus infects immune system cells, e.g., lymphocytes or macrophages. In some embodiments, a virus infection is associated with damage to a cell type, organ, or organ system of interest. Such damage could arise due to infection of cells by the virus and/or due to immune-mediated mechanisms.

In some embodiments, a compound is useful for research purposes, e.g., to further study the role of PLA2G16 in normal physiologic processes or pathologic processes. For example, a compound can be used to further study the role of PLA2G16 in metabolism and/or in viral infection.

In another aspect, the invention provides a method of generating a non-human multicellular organism, e.g., a non-human animal, e.g., a non-human vertebrate, that has increased resistance to viral infection, e.g., by a picornavirus. In one aspect, the non-human multicellular organism has reduced endogenous PLA2G16 activity as compared with a normal, non-transgenic organism of the same species. In some embodiments, the organism is a transgenic, non-human vertebrate that has a targeted insertion into, or deletion of at least part of the PLA2G16 gene, so that the animal has reduced expression of functional PLA2G16. In other embodiments, the transgenic non-human animal expresses an RNAi agent, e.g., a shRNA, that reduces PLA2G16 expression. In some embodiments, the organism is not a rodent. In some embodiments the organism is not a mouse. In some embodiments, the vertebrate is an animal of commercial importance. For example, the organism may contribute at least $10,000 to the gross national product of at least one country and/or be an object of interstate or international commerce. Exemplary animals of commercial importance are, e.g., cows, horses, sheep, goats, pigs, chickens, turkeys, fish. In some embodiments, an animal is a domesticated animal, e.g., a farm animal, e.g., livestock such as a cow, pig, sheep, goat, or horse. In some embodiments, a virus-resistant animal is of a non-domesticated species. Optionally the species is endangered. The method can be used to identify individuals that are resistant to viral infection and have improved likelihood of surviving in the wild or in captivity. Animal resistance to viral infection may reduce the spread of viruses that can infect both animal and human hosts. Mutations or deletions can be engineered using, e.g., homologous recombination, zinc finger nuclease-mediated recombination, oligonucleotide-mediated gene modification, etc. The transgenic organism can be generated using standard methods known in the art for generating such organisms. For example, somatic cell nuclear transfer (SCNT) can be used.

In another aspect, the invention provides a method comprising identifying a non-human multicellular organism, e.g., a non-human vertebrate, e.g., a non-human animal, with reduced or absent functional PLA2G16. In some embodiments, the organism is not a rodent. In some embodiments the animal is not a mouse. In some embodiments, the organism has reduced expression of PLA2G16. In some embodiments the organism expresses a functionally inactive variant or fragment of PLA2G16. For example, the organism could have a frameshift mutation or a deletion or alteration of at least some residues needed for activity. The organism can be identified using, e.g., genotyping (e.g., to identify animals that have mutations or polymorphisms that result in decreased or altered PLA2G16) and/or examining expression level in tissues and identifying animals with low or absent PLA2G16 expression or activity. In some embodiments, polymorphisms, e.g., single nucleotide polymorphisms (SNPs) that are known in the art are examined. For example, genome projects and other sequencing efforts have identified numerous SNPs in animal genomes. SNPs, e.g., SNPs located in or near the PLA2G16 gene can be assessed to identify those that are associated with altered, e.g., reduced or absent, functional PLA2G16. Animals carrying such SNPs can be identified. In some embodiments, the reduced or absent PLA2G16 occurs in at least some tissues and/or cells that are targets for infection by a virus. In some embodiments, the reduced or absent PLA2G16 occurs in most or all tissues. Organisms with a desirable trait (e.g., reduced or absent PLA2G16) can be selected. Standard breeding techniques can be applied to produce animals with particularly low PLA2G16 expression and/or activity. For example, standard methods of livestock breeding could be used. Traditional breeding schemes and/or marker-assisted selection may be employed. In some embodiments, a mutation or polymorphism is a spontaneously arising mutation, i.e., it is not generated by man. In some embodiments, a mutation is generated by man, e.g., using radiation or chemical mutagenesis. Thus the invention provides a method of producing a non-genetically modified non-human organism, e.g., non-human animal, with reduced or absent functional PLA2G16. In some embodiments, the method comprising identifying or selecting an organism with reduced or absent functional PLA2G16. In some embodiments, the non-human organism, is produced using selective breeding techniques. The invention further provides such organisms and methods of use thereof.

In some embodiments, a method comprises providing or using an organism with reduced or absent functional PLA2G16 in agriculture and/or animal husbandry. The organism can be a genetically modified organism or a non-genetically modified organism. The organism may have reduced likelihood of infection with a virus and/or may have reduced severity of infection. For example, in some embodiments the animal has reduced likelihood of infection and/or reduced severity of infection by a foot-and-mouth disease virus. In some embodiments the animal has reduced likelihood of infection and/or reduced severity of infection by a bovine or porcine enterovirus. In some embodiments, the invention provides a method comprising (a) providing an animal that has reduced or absent functional PLA2G16; and (b) engaging in animal husbandry using the animal. Animal husbandry encompasses the breeding and raising of animals for meat or to harvest animal products (such as milk, eggs, or wool) as well as the breeding and care of species for work and/or companionship. Agriculture refers to the production of food and/or goods through farming.

One skilled in the art readily appreciates that the present invention is well adapted to carry out the objects and obtain the ends and advantages mentioned, as well as those inherent therein. The details of the description and the examples herein are representative of certain embodiments, are exemplary, and are not intended as limitations on the scope of the invention. Modifications therein and other uses will occur to those skilled in the art. These modifications are encompassed within the spirit of the invention. It will be readily apparent to a person skilled in the art that varying substitutions and modifications may be made to the invention disclosed herein without departing from the scope and spirit of the invention.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. It is contemplated that all embodiments described herein are applicable to all different aspects of the invention where appropriate. It is also contemplated that any of the embodiments or aspects can be freely combined with one or more other such embodiments or aspects whenever appropriate. Where elements are presented as lists, e.g., in Markush group or similar format, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. For example, any one or more viral genera, viral species, viruses, assays, compounds, diseases, subjects, or combinations thereof, can be excluded.

Where the claims or description relate to a composition of matter, e.g., a compound it is to be understood that methods of making or using the composition of matter according to any of the methods disclosed herein, and methods of using the composition of matter for any of the purposes disclosed herein are aspects of the invention, unless otherwise indicated or unless it would be evident to one of ordinary skill in the art that a contradiction or inconsistency would arise. Where the claims or description relate to a method, e.g., a method of identifying a compound, it is to be understood that methods of using the compound, or formulating a composition comprising the compound, as described herein, are aspects of the invention, unless otherwise indicated or unless it would be evident to one of ordinary skill in the art that a contradiction or inconsistency would arise.

Where ranges are given herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. It is also understood that where a series of numerical values is stated herein, the invention includes embodiments that relate analogously to any intervening value or range defined by any two values in the series, and that the lowest value may be taken as a minimum and the greatest value may be taken as a maximum. Numerical values, as used herein, include values expressed as percentages. For any embodiment of the invention in which a numerical value is prefaced by "about" or "approximately", the invention includes an embodiment in which the exact value is recited. For any embodiment of the invention in which a numerical value is not prefaced by "about" or "approximately", the invention includes an embodiment in which the value is prefaced by "about" or "approximately". "Approximately" or "about" generally includes numbers that fall within a range of 1% or in some embodiments within a range of 5% of a number or in some embodiments within a range of 10% of a number in either direction (greater than or less than the number) unless otherwise stated or otherwise evident from the context (except where such number would impermissibly exceed 100% of a possible value). It should be understood that, unless clearly indicated to the contrary, in any methods claimed herein that include more than one act, the order of the acts of the method is not necessarily limited to the order in which the acts of the method are recited, but the invention includes embodiments in which the order is so limited. It should also be understood that unless otherwise indicated or evident from the context, any product or composition described herein may be considered "isolated".

EXAMPLES

Example 1

Characterization and Retroviral Infection of KBM7 Subclones

We first characterized a haploid genome setting in human cells that we believed would be permissive for efficient forward genetic approaches. A subclone of the CML cell line KBM7 has been described to carry a near haploid chromosome set (Kotecki, M., Reddy, P. S., and Cochran, B. H. Isolation and characterization of a near-haploid human cell line. Exp Cell Res 252, 273-280, 1999). First we examined if this cell line (generously provided by Dr. B. H. Cochran, Tufts University School of Medicine, Boston, Mass.) could be easily propagated, was tolerant to viral infection and could be efficiently subcloned. The term "KBM7 cell line" is used herein to refer to this near-haploid cell line or to a subclone thereof. Cells of the KBM7 cell line or a subclone thereof may be referred to as "KBM7 cells". KBM7 cells had a high subcloning efficiency (of around ~80%), and several of the subclones were examined further. The KBM7 subclones proliferated readily with a generation time of approximately 24 hrs and could be maintained at sparse and very high cell densities (e.g., ~1×10$^7$ cells/ml). Importantly, flow cytometric analysis indicated that KBM7 subclones had a hypodiploid karyotype as compared to diploid HCT116 colorectal carcinoma cells. One subclone was examined further by 24-color FISH spectral karyotyping and shown to be haploid for all chromosomes except chromosome 8 and to contain a Philadelphia chromosome (t(9; 22)) characteristic of BCR-ABL transformed chronic myelogenous leukemia cells. See also, PCT Publication No. WO 2011/006145 and Carette J E, et al., Haploid genetic screens in human cells identify host factors used by pathogens, Science. 2009 Nov. 27; 326(5957):1231-5.

Example 2

Retroviral Infection of KBM7 Cells

We next showed that KBM-7 cells could be infected with retroviruses. Virus was produced by transfection of a GFP expressing retroviral vector with packaging vectors in 293T cells (obtained from ATCC). The retroviral vector was pLIB-GFP (Clontech) but it will be understood that many different retroviral vectors could be used. Supernatant containing virus was used to infect KBM7 cells. To improve the infection efficiency of KBM7 cells with retroviruses, different conditions were tested. Centrifugation of the cells in a 24-well tissue culture dish for 45 minutes at 2,000 pm at room temperature resulted in a 2-fold increase in infection efficiency compared to no centrifugation. Next the effect of retronectin, polybrene and protamine sulphate addition was tested, yielding efficiencies of 25%, 33% and 44%, respectively. Eight microgram per milliliter culture medium of protamine sulphate is the preferred addition. Concentration of virus by ultracentrifugation for 1.5 h at 25,000 r.p.m. in a Beckman SW28 rotor dramatically improved infection rates compared to undiluted virus and was preferred over concentration by Amicon filters. In conclusion, KBM-7 cells are optimally infected when concentrated virus is used for a spin-infection in the presence of protamine sulphate. These subclones could be efficiently (~70-90%) infected with GFP expressing retroviral or lentiviral viruses that were VSV-G pseudotyped and maintained high levels of GFP expression for several months.

Example 3

Construction of Gene Trap Vectors Containing Vectors Containing Puromycin and GFP Selectable Markers Retroviral gene trap vectors that contain an inactivated LTR, a strong splice-acceptor site derived from the long fiber gene of Adenovirus serotype 40 (Carette et al. 2005 The Journal of Gene Medicine 7(8) 1053-1062), and either GFP or the puromycin resistance gene (PURO) followed by a SV40 polyadenylation signal were constructed as follows. The coding sequence of the PURO or GFP was obtained by PCR amplification with primers containing overhanging ClaI and NheI restriction sites as well as partial splice acceptor sites: (GFP:5'-GATCGCTAGCCGCATTTCTTTTTTCCA-GATGGTGAGCAAGGGCGAGG-3' (SEQ ID NO: 5) and 5'-GATCGGATCCTTACTTGTACAGCTCGTCCATGC-3' (SEQ ID NO: 6) PURO: 5'-GATCGCTAGCCG-CATTTCTTTTTTCCAGATGACCGAGTACAAGCCCAC-3' (SEQ ID NO: 7) and 5'-GATCGGATCCTCAGGCAC-CGGGCTTGCGGGTC-3' (SEQ ID NO: 8)). These PCR products were inserted in pEGFPC 1 (Clontech) replacing EGFP. Subsequently PCR was performed to introduce the complete splice acceptor site and to obtain either GFP or PURO followed by the poladenylation signal using primers containing overhanging ClaI and BamHI sites as well as the 5' end of the splice acceptor signal (GFP: 5'-GATCATC-GATCGCAGGCGCAATCTTCG-CATTTCTTTTTTCCAGATGG-3' (SEQ ID NO: 9). and 5'-GATCGGATCCTTACTTGTACAGCTCGTCCATGC-3'

(SEQ ID NO: 10) PURO: 5'-GATCATCGATCGCAGGCG-CAATCTTCGCATTTCTTTTTTCCAGATGAC-3' (SEQ ID NO: 11) and 5'-GATCGGATCCTTACTTGTA-CAGCTCGTCCATGC-3') (SEQ ID NO: 12). These PCR products were inserted in pRETRO-SUPER (Brummelkamp et al. 2002 Cancer Cell. 2(3):243-7) replacing the polIII promoter. The resulting plasmids were named pGT-GFP and pGT-PURO, Gene trap constructs containing a GFP or a puromycin reporter gene in all three reading frames were generated.

The viral vectors contain an adenoviral splice acceptor site immediately upstream of a promoterless reporter and polyadenylation signal so that vector insertion into an intron of an active gene inactivates the native locus, and transcription driven by the gene's promoter results in a fusion transcript in which the upstream exon(s) are spliced to the GFP or PURO gene. Since transcription terminates at the inserted polyA site, the resulting fusion transcript encodes a truncated and nonfunctional version of the cellular protein and either GFP or PURO, as shown schematically in FIG. 1C for a gene trap vector in which the gene encoding GFP gene serves as a reporter gene.

Example 4

Generation of Mutant Cell Library

To generate a cell library with knock-out alleles in nearly all genes, the near-haploid KBM7-cells were infected with the gene traps generated as described in Example 3, Gene trap virus was made by transfection of 293T cells in T175 dishes with either pGT-GFP or pGT-PURO combined with retroviral packaging plasmids. The virus-containing supernatant was concentrated using ultracentrifugation for 1.5 h at 25,000 r.p.m. in a Beckman SW28 rotor. Batches of mutant KBM7 cells are typically made by infection of one 24-well tissue culture dish containing 1.5 million cells per well using the method described in Example 2. Cells infected with the gene trap containing the puromycin resistance gene were selected 2 days after infection using 500 ng puromycin per milliliter. After selection by limiting dilution, cells were expanded and frozen down for further screens. The GFP gene trap infected cells were either used for screens unselected to negate the gene trap introduced bias for actively expressed genes or were selected using FACS sorting for GFP-expressing cells. In some cases further stratification based on GFP expression was performed to obtain batches of cells with different levels of GFP. To increase the likelihood of identifying genes encoding gene products with a relatively longer half-life, the screens were performed on or after day 6 after gene trap infection, thereby allowing the gene products to dilute during cell proliferation.

Example 5

Generation of a New Cell Type Useful for Haploid Genetics

We generated an additional cell type suitable for haploid genetics using somatic cell reprogramming, a method that has recently been described that allows reprogramming of the differentiated cell state by, e.g., introduction of pluripotency-inducing transcription factors such as OCT4, SOX2, KLF4 and c-Myc (Zaehres, H., and Scholer, H. R. (2007). Induction of pluripotency: from mouse to human. Cell 131, 834-835). Introduction of these four transcription factors into KBM-7 cells by retroviral infection (as described in Takahashi, K., et al., Cell, 131(5):861-72, 2007) resulted in the formation of adherent cell clones. Some or most of these clones lost the hematopoietic cell surface markers CD43 and CD45. The majority of these cells were not pluripotent. A subclone was isolated and named "HAP1". HAP1 cells could be cultured in medium containing 10% FCS and could be expanded using trypsin. These cells were not hematopoietic and the majority of these cells had a single copy of each chromosome including chromosome 8

Figure 1:
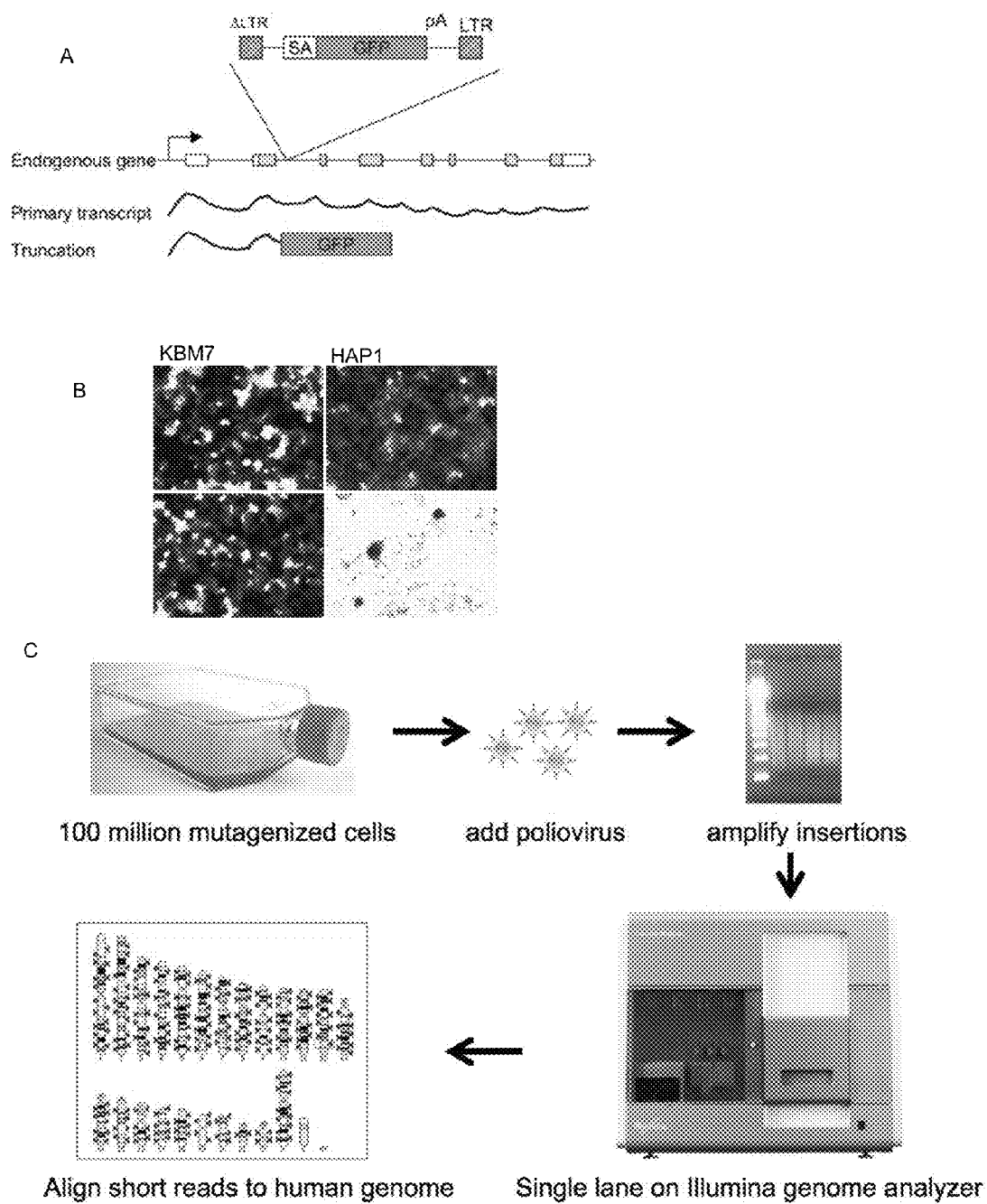
FIG. 1. A. Schematic outline of gene-trap vector integration in an endogenous gene. B. Images demonstrating that KBM7 cells cannot be productively infected with poliovirus (FIG. 1B, left panels), however, HAP1 cells are very susceptible to poliovirus infection and undergo massive cell death within a few days (FIG. 1B, compare upper right and lower right panels). Schematic overview of haploid genetic screen for genes critical for poliovirus replication.

In contrast to influenza virus, KBM7 cells cannot be productively infected with poliovirus (FIG. 1B, left panels). HAP1 cells however, are very susceptible to poliovirus infection and undergo massive cell death within a few days (FIG. 1B, compare upper right and lower right panels). Subsequently, fresh HAP1 cells were infected with our gene trap retroviral construct and exposed to poliovirus. Two resistant colonies were expanded and the integrations were mapped. Both mutants contained independent integrations in the known poliovirus entry receptor, PVR, thus explaining their resistance. These results indicated that factors essential for poliovirus infection can be found through haploid genetic screens in reprogrammed, non-hematopoietic cell lines derived from KBM7 cells, such as HAP1 cells.

Example 6

Identification of PLA2G16 as a Host Factor for Poliovirus

In order to identify new host factors for poliovirus, a larger screen was undertaken using HAP1 cells (FIG. 1C). Retrovirus was prepared and a mutant HAP1 cell library was generated as described in Example 4. One hundred million mutagenized haploid HAP1 cells were contacted with poliovirus and resistant colonies were allowed to grow out. To identify gene trap insertion sites, an inverse PCR protocol was adapted for use with massively parallel sequencing techniques. In order to do so, genomic DNA was isolated from 30 million cells that had been infected with a gene trap vector. Four digestion reactions were performed per sample, two using NlaIII and two using MseI. Subsequently the digested DNA was column-purified (Qiagen) and 1 microgram DNA was ligated in a volume of 300 microliter using T4 DNA ligase (NEB) at room temperature overnight. After another round of column purification the DNA was used as template for an inverse PCR with outward facing primers. The oligonucleotides were designed to contain adaptor sequences required for use with the "Illumina Genome Analyzer", a massively parallel sequencing platform. Oligonucleotides used were: 5'-AATGATACGGCGACCACCGAGATCT-GATGGTTCTCTAGCTTGCC-3' (SEQ ID NO: 13) 5'-CAAGCAGAAGACGGCATACGACCCAGGT-TAAGATCAAGGTC-3' (SEQ ID NO: 14) for templates digested with NlaIII. Oligonucleotides used were: 5'-AAT-GATACGGCGACCACCGAGATCTGATGGTTCTCTAG CTTGCC-3' (SEQ ID NO: 15) 5'-CAAGCAGAAGACG-GCATACGACGTTCTGTGTTGTCTCTGTCTG-3' (SEQ ID NO: 16) for templates digested with MseI. The four PCR reactions were pooled and used for analysis on an Illumina Genome Analyzer according to manufacturer's protocol and mapped against the human genome. Typically ~20,000 insertions sites mapping to different positions on the human genome are obtained from this analysis. To facilitate identification of genomic loci that are enriched for gene trap insertions "insertion density" was plotted in a graph. Insertion density was determined for every insertion by calculating 1/(average distance to three following insertions sites).

Figure 2:
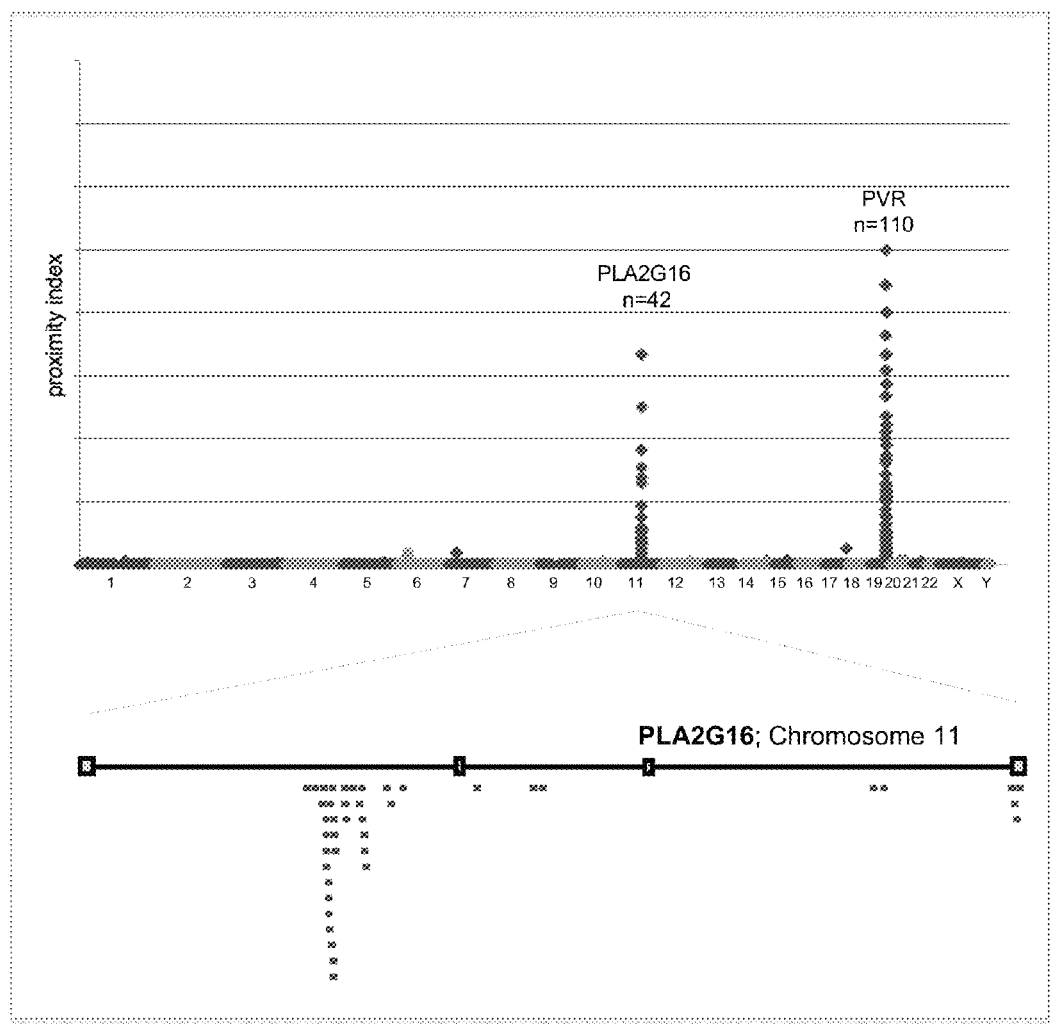
FIG. 2. Haploid genetic screen identifies PLA2G16 as critical for poliovirus infection. Mutagenized haploid cells were contacted with poliovirus and resistant colonies were allowed to grow out. Gene trap insertion sites were determined using inverse PCR and massively parallel sequencing. The plot shows the positions on the human chromosome to which individual gene trap mutations were mapped on the x-axis and the inverse of the distance of a particular mutation to its neighbors on the y-axis. Mutations are highly enriched in chromosome 19 in the known poliovirus receptor (PVR) and on chromosome 11 in the phospholipase PLA2G16 that contained 42 independent gene trap insertions.

The plot in FIG. 2 shows the positions on the human chromosome to which individual gene trap mutations were mapped on the x-axis and the inverse of the distance of a particular mutation to its neighbors on the y-axis. Mutations were found to be highly enriched in chromosome 19 in the known poliovirus receptor (PVR) and on chromosome 11 in a region that we identified as the gene encoding the phospholipase PLA2G16. This gene contained 42 independent gene trap insertions.

Example 7

Confirmation that Gene Trap Insertion Ablates PLA2G16 Expression

Figure 3:
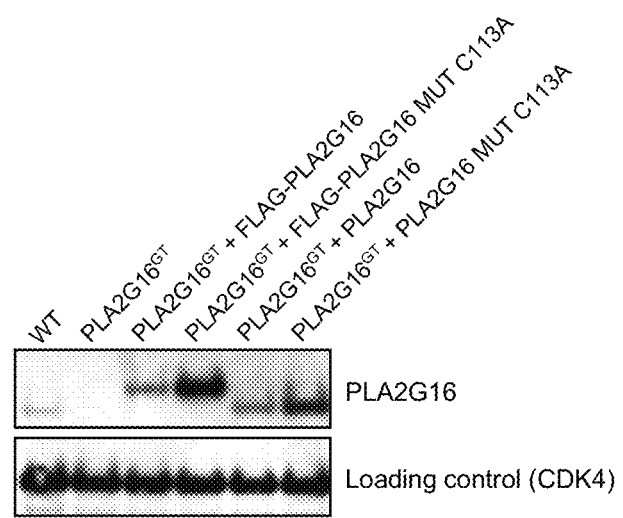
FIG. 3. Western blot analysis for expression of PLA2G16 in wild type haploid cells (WT; lane 1), cells containing a gene trap insertion in PLA2G16 gene (PLA2G16$^{GT}$; lane 2) cells containing a gene trap in PLA2G16 and expressing FLAG-tagged PLA2G16 (lane 3); cells containing a gene trap in PLA2G16 expressing FLAG-tagged mutant PLA2G16 (lane 4); cells containing a gene trap in PLA2G16 and expressing untagged PLA2G16 (lane 5); cells containing a gene trap in PLA2G16 and expressing untagged mutant PLA2G16 (lane 6).
Figure 4:
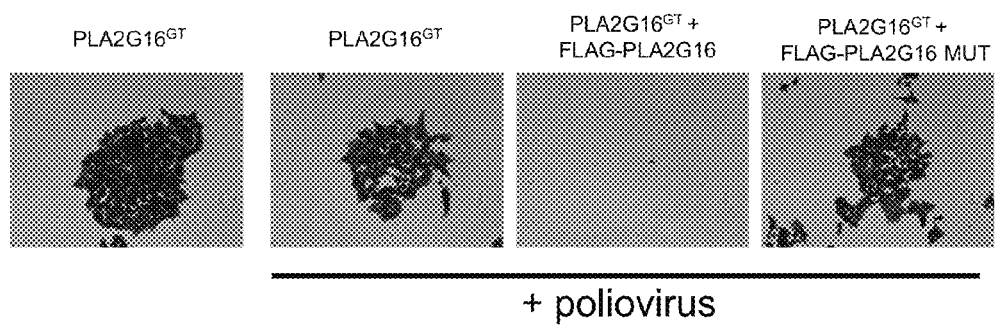
FIG. 4. Haploid cells containing a PLA2G16 gene trap insertion are resistant to poliovirus infection. Complementation of PLA2G16 by retroviral overexpression restores sensitivity of these cells to poliovirus. This requires the catalytic activity of PLA2G16 because complementation with a catalytic site mutant (C113A) does not restore sensitivity.
Figure 6:
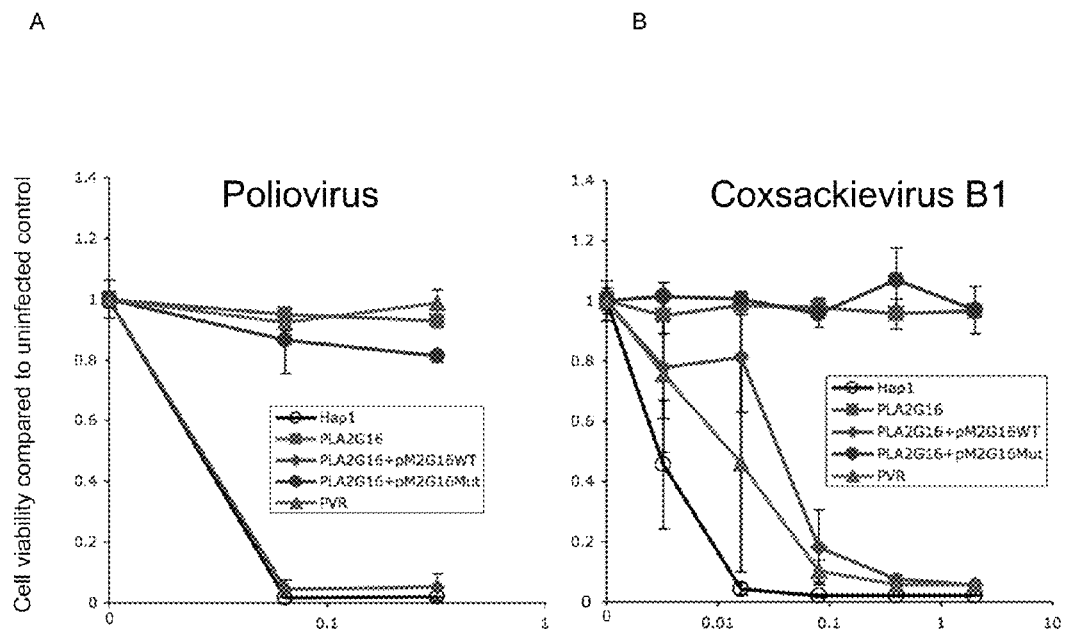
FIG. 6. (A) Sensitivity of wild type and gene trap mutant cells to poliovirus. (B) Sensitivity of wild type gene trap mutant cells to coxsackievirus B1. Poliovirus was added to cells at the indicated MOIs (X-axis) and viability was measured three days later using an MTT assay. HAP1: Wild type HAP1 cells (without gene trap)

Changing amino acid 113 from C to A (C113A mutation) renders PLA2G16 catalytically inactive (Duncan, supra). Retroviral constructs suitable for expressing wild type or mutant human PLA2G16 in HAP1 cells with or without a FLAG tag were generated using standard methods and introduced into HAP1 cells that contained a gene trap insertion in the PLA2G16 locus (PLA2G16$^{GT}$) The pMX retroviral vector was used expressing Flag-tagged human PLA2G16 and a IRES-Blasticidin selectable marker gene or. For the non-tagged version of PLA2G16 human PLA2G16 cDNA was cloned into the pBABEpuro retroviral vector). A Western blot was performed using a polyclonal antibody to PLA2G16 to examine PLA2G16 expression (FIG. 3). PLA2G16 was detected in wild type (WT) HAP1 cells (i.e., HAP 1 cells that had not been exposed to the gene trap vector) (lane 1). As expected, PLA2G16$^{GT}$ cells lacked detectable PLA2G16 (lane 2). As seen in lanes 3-6, PLA2G16 was readily detected in PLA2G16$^{GT}$ cells that had received a construct encoding PLA2G16 (wild type or C113A mutant). As expected FLAG-tagged PLA2G16 was slightly larger in size than untagged PLA2G16 (compare lanes 3 and 4 versus 5 and 6). This experiment demonstrated that the gene trap had indeed effectively abrogated PLA2G16 expression and that the constructs restored PLA2G16 expression when introduced into HAP1 PLA2G16$^{GT}$ cells.

Example 8

Confirmation that Lack of PLA2G16 Renders Cells Resistant to Poliovirus

To confirm that ablating PLA2G16 expression inhibits infection by poliovirus, haploid PLA2G16$^{GT}$ cells were infected with retrovirus encoding PLA2G16 or a catalytically inactive mutant (containing a C113A alteration). PLA2G16$^{GT}$ grow robustly in the absence of poliovirus (FIG. 4, left panel). As shown in FIG. 4 (second panel from left), PLA2G16$^{GT}$ cells (containing a PLA2G16 gene trap insertion) also grow in the presence of poliovirus. Complementation of PLA2G16 by retroviral overexpression of wild type PLA2G16 in PLA2G16$^{GT}$ cells restores sensitivity of these cells to poliovirus (second panel from right). This requires the catalytic activity of PLA2G16 because complementation with a catalytic site mutant (C113A) does not restore sensitivity (right panel).

FIG. 6A shows the sensitivity of gene trap mutant cells to poliovirus in graphical form. Cells were infected with indicated MOIs and three days after infection viability was measured using an MTT assay. Gene trap insertion into PLA2G16 renders cells sensitive to infection by poliovirus, and sensitivity can be restored by expressing wild type but not catalytically inactive mutant PLA2G16 in the cells. As expected, gene trap insertion into poliovirus receptor renders haploid cells resistant to poliovirus infection. Gene trap insertion into PLA2G16 has an essentially equivalent effect to gene trap insertion into poliovirus receptor.

Example 9

PLA2G16 Insertion Renders Haploid Cells Resistant to Coxsackievirus

FIG. 5 shows effect of coxsackievirus B1 on wild type haploid cells and cells lacking functional PLA2G16. Cells were plated in 24-well wells and monolayers were treated with coxsackievirus B1 at the indicated MOIs. Four days after infection viable, adherent cells were stained using crystal violet. Wild type cells were highly sensitive to the virus at all MOIs tested (top row). Cells mutant for PLA2G16 due to the gene trap insertion were essentially unaffected by of coxsackievirus B1, even at high concentrations of virus (second row from top). Complementation of PLA2G16 by retroviral overexpression restores sensitivity of these cells to coxsackievirus B1 (third row from top). This requires the catalytic activity of PLA2G16 because complementation with a catalytic site mutant (C113A) does not restore sensitivity (bottom row). Thus, cells containing a PLA2G16 gene trap insertion are resistant to coxsackievirus B1, and sensitivity can be restored by expressing wild type but not catalytically inactive mutant PLA2G16.

FIG. 6B shows the sensitivity of gene trap mutant cells to coxsackievirus B1 in graphical form. Cells were contacted with virus at the indicated MOIs and three days later viability was measured using an MTT assay. Gene trap insertion into PLA2G16 renders cells sensitive to infection by coxsackievirus B1, and sensitivity can be restored by expressing wild type but not catalytically inactive mutant PLA2G16 in the cells. As expected, gene trap insertion into the poliovirus receptor does not significantly affect sensitivity to coxsackievirus B1.

Example 10

PLA2G16 Knockdown Increases Resistance to Rhinovirus

Ability of RNAi-mediated knockdown of PLA2G16 to inhibit rhinovirus infection was studied in HeLa cells. PLA2G16 expression was inhibited in HeLa cells using two different siRNAs targeted to PLA2G16, and the ability of the cells to survive and proliferate after exposure to human rhinoviruses HRV-2 and HRV-14 was examined. The siRNAs were Ambion siRNA 223200, sequence 5'-CAAGAAACAAGCGACAAAtt-3' (SEQ ID NO: 17) and siRNA 21977 sequence 5'-GUACCAGGUCAACAACAAAtt-3' (SEQ ID NO: 18). HeLa cells that had not been transfected with siRNA or were transfected with a control siRNA were highly susceptible to infection by human rhinoviruses HRV-2 and HRV-14 (FIG. 7, two left columns). Knock down of PLA2G16 in Hela cells resulted in significantly increased resistance to both HRV-2 and HRV-14 (FIG. 7, right two columns). Cells transfected with siRNA targeted to PLA2G16 were able to survive and proliferate well following exposure to HRV-2 and HRV-14.

We claim:

1. A method of identifying a candidate antiviral compound comprising steps of: (a) providing a composition comprising a PLA2G16 polypeptide and a test compound; (b) determining whether the test compound inhibits the PLA2G16 polypeptide, wherein if the compound inhibits the PLA2G16 polypeptide, the compound is identified as a candidate antiviral compound; and (c) assessing the ability of the candidate antiviral compound to inhibit viral infection of a cell or subject.

2. The method of claim 1, wherein step (b) comprises determining whether the test compound inhibits (i) expression of the PLA2G16 polypeptide, or (ii) an enzymatic activity of the PLA2G16 polypeptide.

3. The method of claim 2, the enzymatic activity is phospholipase A2 activity.

4. The method of claim 1, wherein the composition of step (a) is:
   (i) a cell-free composition comprising purified PLA2G16, and wherein step (b) comprises determining whether the test compound inhibits enzymatic activity of PLA2G16; or
   (ii) a cell that expresses a PLA2G16 polypeptide, and wherein step (b) comprises determining whether the test compound inhibits expression or enzymatic activity of PLA2G16.

5. The method of claim 1, wherein if the compounds inhibits the PLA2G16 polypeptide, the compound is identified as a candidate antiviral compound useful for inhibiting viral infection by a Picornavirus.

6. The method of claim 1, further comprising a step selected from the group consisting of:
   (i) contacting a cell with the compound and a virus, wherein the cell would be susceptible to the virus in the absence of the compound;
   (ii) administering the compound to a subject, wherein the subject would be susceptible to infection by the virus in the absence of the compound;
   (iii) contacting a cell that is infected by the virus with the compound; and
   (iv) administering the compound to a subject, wherein the subject is infected by a virus.

7. A method of validating a candidate antiviral compound comprising steps of: (a) providing a candidate antiviral compound identified according to the method of claim 1; and (b) determining whether the compound inhibits infection of a cell or organism by a virus, wherein if the compound inhibits infection of a cell or organism by the virus, the compound is validated as an antiviral compound.

8. The method of claim 7, wherein the virus is a Picornavirus.

9. A composition comprising: (a) a PLA2G16 inhibitor; (b) a virus; and (c) a population of cells.

10. The composition of claim 9, wherein the virus is present at a multiplicity of infection (MOI) of at least 0.01.

11. The composition of claim 9, wherein the virus is a Picornavirus.

12. The composition of claim 9, wherein the cells are selected from the group consisting of cells in culture, vertebrate cells, mammalian cells, and human cells.

13. The composition of claim 9, wherein at least some of the cells are infected by the virus.

* * * * *

SEQUENCE LISTING

<160> NUMBER OF SEQ ID NOS: 18

<210> SEQ ID NO 1
<211> LENGTH: 162
<212> TYPE: PRT
<213> ORGANISM: Homo sapiens

<400> SEQUENCE: 1

Met Arg Ala Pro Ile Pro Glu Pro Lys Pro Gly Asp Leu Ile Glu Ile
1               5                   10                  15

Phe Arg Pro Phe Tyr Arg His Trp Ala Ile Tyr Val Gly Asp Gly Tyr
            20                  25                  30

Val Val His Leu Ala Pro Pro Ser Glu Val Ala Gly Ala Gly Ala Ala
        35                  40                  45

Ser Val Met Ser Ala Leu Thr Asp Lys Ala Ile Val Lys Lys Glu Leu
    50                  55                  60

Leu Tyr Asp Val Ala Gly Ser Asp Lys Tyr Gln Val Asn Asn Lys His
65                  70                  75                  80

Asp Asp Lys Tyr Ser Pro Leu Pro Cys Ser Lys Ile Ile Gln Arg Ala
                85                  90                  95

Glu Leu Val Gly Gln Glu Val Leu Tyr Lys Leu Thr Ser Glu Asn
            100                 105                 110

Cys Glu His Phe Val Asn Glu Leu Arg Tyr Gly Val Ala Arg Ser Asp
        115                 120                 125

Gln Val Arg Asp Val Ile Ile Ala Ala Ser Val Ala Gly Met Gly Leu
    130                 135                 140

Ala Ala Met Ser Leu Ile Gly Val Met Phe Ser Arg Asn Lys Arg Gln
145                 150                 155                 160

Lys Gln

<210> SEQ ID NO 2
<211> LENGTH: 162
<212> TYPE: PRT
<213> ORGANISM: Mus musculus

<400> SEQUENCE: 2

Met Leu Ala Pro Ile Pro Glu Pro Lys Pro Gly Asp Leu Ile Glu Ile
1               5                   10                  15

Phe Arg Pro Met Tyr Arg His Trp Ala Ile Tyr Val Gly Asp Gly Tyr
            20                  25                  30

Val Ile His Leu Ala Pro Pro Ser Glu Ile Ala Gly Ala Gly Ala Ala
        35                  40                  45

Ser Ile Met Ser Ala Leu Thr Asp Lys Ala Ile Val Lys Lys Glu Leu
    50                  55                  60

Leu Cys His Val Ala Gly Lys Asp Lys Tyr Gln Val Asn Asn Lys His
65                  70                  75                  80

Asp Glu Glu Tyr Thr Pro Leu Pro Leu Ser Lys Ile Ile Gln Arg Ala
                85                  90                  95

Glu Arg Leu Val Gly Gln Glu Val Leu Tyr Arg Leu Thr Ser Glu Asn
            100                 105                 110

Cys Glu His Phe Val Asn Glu Leu Arg Tyr Gly Val Pro Arg Ser Asp
        115                 120                 125

Gln Val Arg Asp Ala Val Lys Ala Val Gly Ile Ala Gly Val Gly Leu
    130                 135                 140

Ala Ala Leu Gly Leu Val Gly Val Met Leu Ser Arg Asn Lys Lys Gln
145                 150                 155                 160

Lys Gln

<210> SEQ ID NO 3
<211> LENGTH: 160
<212> TYPE: PRT
<213> ORGANISM: Rattus norvegicus

<400> SEQUENCE: 3

Met Pro Ile Pro Glu Pro Lys Pro Gly Asp Leu Ile Glu Ile Phe Arg
1               5                   10                  15

Pro Met Tyr Ser His Trp Ala Ile Tyr Val Gly Asp Gly Tyr Val Ile
            20                  25                  30

His Leu Ala Pro Pro Ser Glu Ile Pro Gly Ala Gly Ala Ala Ser Ile
        35                  40                  45

Met Ser Ala Leu Thr Asp Lys Ala Ile Val Lys Lys Glu Leu Leu Arg
50                  55                  60

Asp Val Ala Gly Lys Asp Lys Tyr Gln Val Asn Asn Lys His Asp Lys
65                  70                  75                  80

Glu Tyr Thr Pro Leu Pro Leu Asn Lys Ile Ile Gln Arg Ala Glu Glu
                85                  90                  95

Leu Val Gly Gln Glu Val Leu Tyr Arg Leu Thr Ser Glu Asn Cys Glu
            100                 105                 110

His Phe Val Asn Glu Leu Arg Tyr Gly Val Pro Arg Ser Asp Gln Val
        115                 120                 125

Arg Asp Ala Val Lys Val Ala Thr Val Thr Gly Val Gly Leu Ala Ala
130                 135                 140

Leu Gly Leu Ile Gly Val Met Leu Ser Arg Asn Lys Lys Gln Lys Gln
145                 150                 155                 160

<210> SEQ ID NO 4
<211> LENGTH: 8
<212> TYPE: PRT
<213> ORGANISM: Artificial
<220> FEATURE:
<223> OTHER INFORMATION: motif
<220> FEATURE:
<221> NAME/KEY: misc_feature
<222> LOCATION: (3)..(4)
<223> OTHER INFORMATION: Xaa = any amino acid
<220> FEATURE:
<221> NAME/KEY: misc_feature
<222> LOCATION: (7)..(7)
<223> OTHER INFORMATION: Xaa = any amino acid

<400> SEQUENCE: 4

Cys Cys Xaa Xaa His Asp Xaa Cys
1               5

<210> SEQ ID NO 5
<211> LENGTH: 47
<212> TYPE: DNA
<213> ORGANISM: Artificial
<220> FEATURE:
<223> OTHER INFORMATION: PCR primer

<400> SEQUENCE: 5
gatcgctagc cgcatttctt ttttccagat ggtgagcaag ggcgagg        47

<210> SEQ ID NO 6
<211> LENGTH: 33
<212> TYPE: DNA
<213> ORGANISM: Artificial

```
<220> FEATURE:
<223> OTHER INFORMATION: PCR primer

<400> SEQUENCE: 6
gatcggatcc ttacttgtac agctcgtcca tgc                             33

<210> SEQ ID NO 7
<211> LENGTH: 48
<212> TYPE: DNA
<213> ORGANISM: Artificial
<220> FEATURE:
<223> OTHER INFORMATION: PCR primer

<400> SEQUENCE: 7
gatcgctagc cgcatttctt ttttccagat gaccgagtac aagcccac              48

<210> SEQ ID NO 8
<211> LENGTH: 32
<212> TYPE: DNA
<213> ORGANISM: Artificial
<220> FEATURE:
<223> OTHER INFORMATION: PCR primer

<400> SEQUENCE: 8
gatcggatcc tcaggcaccg ggcttgcggg tc                              32

<210> SEQ ID NO 9
<211> LENGTH: 47
<212> TYPE: DNA
<213> ORGANISM: Artificial
<220> FEATURE:
<223> OTHER INFORMATION: PCR primer

<400> SEQUENCE: 9
gatcatcgat cgcaggcgca atcttcgcat ttcttttttc cagatgg              47

<210> SEQ ID NO 10
<211> LENGTH: 33
<212> TYPE: DNA
<213> ORGANISM: Artificial
<220> FEATURE:
<223> OTHER INFORMATION: PCR primer

<400> SEQUENCE: 10
gatcggatcc ttacttgtac agctcgtcca tgc                             33

<210> SEQ ID NO 11
<211> LENGTH: 48
<212> TYPE: DNA
<213> ORGANISM: Artificial
<220> FEATURE:
<223> OTHER INFORMATION: PCR primer

<400> SEQUENCE: 11
gatcatcgat cgcaggcgca atcttcgcat ttcttttttc cagatgac              48

<210> SEQ ID NO 12
<211> LENGTH: 33
<212> TYPE: DNA
<213> ORGANISM: Artificial
<220> FEATURE:
<223> OTHER INFORMATION: PCR primer

<400> SEQUENCE: 12
gatcggatcc ttacttgtac agctcgtcca tgc                             33
```

```
<210> SEQ ID NO 13
<211> LENGTH: 44
<212> TYPE: DNA
<213> ORGANISM: Artificial
<220> FEATURE:
<223> OTHER INFORMATION: Oligonucleotide template

<400> SEQUENCE: 13
aatgatacgg cgaccaccga gatctgatgg ttctctagct tgcc                    44

<210> SEQ ID NO 14
<211> LENGTH: 41
<212> TYPE: DNA
<213> ORGANISM: Artificial
<220> FEATURE:
<223> OTHER INFORMATION: Oligonucleotide template

<400> SEQUENCE: 14
caagcagaag acggcatacg acccaggtta agatcaaggt c                       41

<210> SEQ ID NO 15
<211> LENGTH: 44
<212> TYPE: DNA
<213> ORGANISM: Artificial
<220> FEATURE:
<223> OTHER INFORMATION: Oligonucleotide template

<400> SEQUENCE: 15
aatgatacgg cgaccaccga gatctgatgg ttctctagct tgcc                    44

<210> SEQ ID NO 16
<211> LENGTH: 43
<212> TYPE: DNA
<213> ORGANISM: Artificial
<220> FEATURE:
<223> OTHER INFORMATION: Oligonucleotide template

<400> SEQUENCE: 16
caagcagaag acggcatacg acgttctgtg ttgtctctgt ctg                     43

<210> SEQ ID NO 17
<211> LENGTH: 20
<212> TYPE: DNA
<213> ORGANISM: Artificial
<220> FEATURE:
<223> OTHER INFORMATION: siRNA 223200

<400> SEQUENCE: 17
caagaaacaa gcgacaaatt                                               20

<210> SEQ ID NO 18
<211> LENGTH: 21
<212> TYPE: DNA
<213> ORGANISM: Artificial
<220> FEATURE:
<223> OTHER INFORMATION: siRNA 21977

<400> SEQUENCE: 18
guaccagguc aacaacaaat t                                             21
```